United States Patent
Chilkoti et al.

(10) Patent No.: US 7,163,712 B2
(45) Date of Patent: Jan. 16, 2007

(54) MICROSTAMPING ACTIVATED POLYMER SURFACES

(75) Inventors: Ashutosh Chilkoti, Durham, NC (US); Zhongping Yang, Woodbury, MN (US); Jinho Hyun, Durham, NC (US)

(73) Assignee: Duke University, Durham, NC (US)

( * ) Notice: Subject to any disclaimer, the term of this patent is extended or adjusted under 35 U.S.C. 154(b) by 466 days.

(21) Appl. No.: 10/176,366

(22) Filed: Jun. 20, 2002

(65) Prior Publication Data

US 2003/0059537 A1    Mar. 27, 2003

Related U.S. Application Data

(63) Continuation-in-part of application No. 09/519,038, filed on Mar. 3, 2000, now Pat. No. 6,444,254.

(51) Int. Cl.
*B05D 5/00* (2006.01)
(52) U.S. Cl. ................ 427/2.13; 427/265; 427/282; 427/414
(58) Field of Classification Search ............ 427/2.13, 427/256, 258, 259, 261, 265, 282, 402, 414; 118/204, 212, 264
See application file for complete search history.

(56) References Cited

U.S. PATENT DOCUMENTS

| | | | | |
|---|---|---|---|---|
| 4,282,287 | A | 8/1981 | Giese | 428/407 |
| 4,737,544 | A | 4/1988 | McCain et al. | 525/54.1 |
| 5,055,316 | A | 10/1991 | Hoffman et al. | 427/2 |
| 5,512,131 | A | 4/1996 | Kumar et al. | 156/655.1 |
| 5,607,475 | A | 3/1997 | Cahalan et al. | 623/11 |
| 5,609,907 | A | 3/1997 | Natan | 427/2.12 |
| 5,620,850 | A | 4/1997 | Bamdad et al. | 530/300 |
| 5,645,883 | A | 7/1997 | Russell et al. | 427/2.25 |
| 5,725,788 | A | 3/1998 | Maracas et al. | 216/41 |
| 5,776,748 | A | 7/1998 | Singhvi et al. | 435/180 |
| 5,817,242 | A | 10/1998 | Biebuyck et al. | 216/41 |
| 5,866,113 | A | 2/1999 | Hendriks et al. | 424/78.17 |
| 5,891,506 | A | 4/1999 | Keogh | 427/2.13 |
| 5,900,160 | A | 5/1999 | Whitesides et al. | 216/41 |
| 5,925,259 | A | 7/1999 | Biebuyck et al. | 216/2 |
| 5,962,136 | A | 10/1999 | Dewez et al. | 428/410 |

(Continued)

FOREIGN PATENT DOCUMENTS

WO    WO 98/58967    12/1998

(Continued)

OTHER PUBLICATIONS

Yang et al, Langmuir, 16, pp. 7482-7492, 2000.*

(Continued)

*Primary Examiner*—Erma Cameron
(74) *Attorney, Agent, or Firm*—Myers Bigel Sibley & Sajovec P.A.

(57) ABSTRACT

Methods of attaching a ligand to a surface are described that include contacting a surface with a substrate containing an amphiphilic comb polymer. The substrate is configured to provide a pattern of the amphiphilic comb polymer on a selected region of the surface. The substrate can be separated from the surface leaving the amphiphilic comb polymer on the selected region of the surface, thus providing a selected region of the surface having amphiphilic comb polymer on it. A ligand can then be deposited on the surface such that the selected region of the surface having the amphiphilic comb polymer is substantially free of the ligand.

30 Claims, 24 Drawing Sheets

U.S. PATENT DOCUMENTS

| | | | |
|---|---|---|---|
| 5,976,826 A | 11/1999 | Singhvi et al. | 435/29 |
| 5,998,588 A | 12/1999 | Hoffman et al. | 530/402 |
| 6,027,890 A | 2/2000 | Ness et al. | 435/6 |
| 6,033,719 A | 3/2000 | Keogh | 427/2.12 |
| 6,048,735 A | 4/2000 | Hessel et al. | 436/518 |
| 6,060,121 A | 5/2000 | Hidber et al. | 427/261 |
| 6,089,853 A | 7/2000 | Biebuyck et al. | 425/447 |
| 6,096,386 A | 8/2000 | Biebuyck et al. | 427/510 |
| 6,165,566 A | 12/2000 | Tropsha | |
| 6,207,749 B1 | 3/2001 | Mayes et al. | 524/731 |
| 6,368,877 B1 | 4/2002 | Zhang et al. | 436/527 |
| 6,521,285 B1* | 2/2003 | Biebuyck et al. | 216/13 |
| 6,569,706 B1* | 5/2003 | Pakbaz et al. | 438/99 |
| 6,692,914 B1* | 2/2004 | Klaerner et al. | 435/6 |
| 6,884,628 B1* | 4/2005 | Hubbell et al. | 436/518 |
| 2002/0004216 A1 | 1/2002 | Abbott et al. | 435/7.92 |
| 2002/0071943 A1* | 6/2002 | Hawker et al. | 428/195 |
| 2003/0132121 A1 | 7/2003 | Breen et al. | 205/231 |

FOREIGN PATENT DOCUMENTS

| | | | |
|---|---|---|---|
| WO | WO 99/21233 A1 * | 4/1999 | |

OTHER PUBLICATIONS

Hyun et al., "Micropatterns of a Cell-Adhesive Peptide on an Amphiphilic Comb Polymer Film," *Langmuir*, vol. 18, 2002, pp. 2975-2979.

Hyun et al., "Micropatterning Biological Molecules on a Polymer Surface Using Elastomeric Microwells," *J. Am. Chem. Soc.*, vol. 123, 2001, pp. 6943-6944.

Amiji et al.; "Surface modification of polymeric biomaterials with poly(ethylene oxide), albumin, and heparin for reduced thrombogenicity" J. Biomater. Sci. Polymer Edn. 4:3 217-234 (1993).

Andrade et al.; Chapter 3—"Poly(ethylene oxide) and Protein Resistance" *Hydrophilic Polymers Performance with Environmental Acceptance* 51-59 (1996).

Hammarback et al.; "Guidance of Neurite Outgrowth by Pathways of Substratum-Adsorbed Laminin" *Journal of Neuroscience Research* 13 213-220 (1985).

Healy et al.; "Spatial Distribution of Mammalian Cells Dictated by Material Surface Chemistry" *Biotechnology and Bioengineering* 43 792-800 (1994).

Horbett et al.; "Chapter 1: Proteins at Interfaces: Current Issues and Future Prospects" *American Chemical Society* 0097-6156/87/0343-0001 pp. 1-33 (1987).

Lee et al.; "Surface properties of copolymers of alkyl methacrylates with methoxy (polyethylene oxide) methacrylates and their application as protein-resistant coatings" *Biomaterials* (1990).

López et al.; "Glow discharge plasma deposition of tetraethylene glycol dimethyl ether for fouling-resistant biomaterial surfaces" *Journal of Biomedical Materials Research* 26 415-439 (1992).

Matsuda et al "Application of Titanium Alloy Wires for the Reattachment of the Greater Trochanter in Total Hip Arthroplasty" *Clinical Materials* 12 41-47 (1993).

Park et al.; "Blood compatibility of SPUU-PEO-heparin graft copolymers" *Journal of Biomedical Materials Research* 26 739-756 (1992).

Prime et al.; "Adsorption of Proteins onto Surfaces Containing End-Attached Oligo(ethylene oxide): A Model System Using Self-Assembled Monolayers" *J. Am. Chem. Soc.* 115 10714-10721 (1993).

Prime et al.; "Self-Assembled Organic Monolayers: Model Systems for Studying Adsorption of Proteins at Surfaces" *Science* 252:5009 1164-1167 (1991).

Singhvi et al.; "Review: Effects of Substratum Morphology on Cell Physiology" *Biotechnology and Bioengineering* 43 764-771 (1994).

Tseng et al.; "Synthesis of photoreactive poly(ethylene glycol) and its application to the prevention of surface-induced platelet activation" *Journal of Biomedical Materials Research* 26 373-391 (1992).

International Search Report, PCT/US03/18487, Aug. 28, 2003.

Adameczyk et al. "An Easy Preparation of Hapten Active Esters via Solid Suported EDAC" *Tetrahedron Letters* 36(46): 8345-8346 (1995).

Arenholz et al. "Laser-Induced Surface Modification and Structure Formation of Polymers" *Applied Surface Science* 69: 16-19 (1993).

Avny et al. "Chemical Modification of Polyester Fiber Surfaces by Amination Reactions with Multifunctional Amines" *J Applied Polymer Science* 32: 4009-4025 (1986).

Bernard et al. "Printing Patterns of Proteins" *Langmuir* 14(9): 2225-2229 (1998).

Bertrand et al. "Modification of Polymer (PET) Surface Reactivity by Low Energy Ion Bombardment" *Nuclear Instruments & Methods in Physical Research Section B* (19-20): 887-890 (1987).

Blawas et al. "Protein Patterning" *Biomaterials* 19: 595-609 (1998).

Brandley et al. "Covalent Attachment of an Arg-Gly-Asp Sequence Peptide to Derivatizable Polyacrylamide Surfaces: Support of Fibroblast Adhesion and Long-Term Growth" *Analytical Biochemistry* 172: 270-278 (1988).

Bui et al. "Surface Modification of the Biochemical Polymer Poly(ethylene terephthalate)" *Analyst* 118: 463-474 (1993).

Chen et al. "Geometric Control of Cell Life and Death" *Science* 276: 1425-1428 (1997).

Chen et al. "Micropatterned Surfaces for Control of Cell Shape, Position and Function" *Biotechnol Prog* 14: 356-363 (1998).

Chilkoti et al. "Molecular Origins of the slow Streptavidin-Biotin Dissociation Kinetics" *J Am Chem Soc* 117: 10622-10628 (1995).

Chilkoti et al. "Site-Directed Mutagenesis Studies of the High-Affinity Streptavidin-Biotin Complex: Contributions of Tryptophan Residues 79, 108, and 120" *Proc Natl Acad Sci USA* 92: 1454-1758 (1995).

Cima "Polymer Substrates for Controlled Biological Interactions" *J Cellular Biochemistry* 56: 155-161 (1994).

Dave et al. "Studies on Modification of Polyester Fabrics I: Alkaline Hydrolysis" *Journal of Applied Polymer Science* 33:455-477 (1987).

Desai et al. "Surface Physical Interpenetrating Networks of poly-(ethylene terephthalate) and Poly(ethylene oxide) with Biomedical Applications" *Macromolecules* 25: 226-232 (1992).

Dewez et al. "Adhesion of mammalian Cells to Polymer Surfaces: from Physical Chemistry of Surfaces to Selective Adhesion on Defined Patterns" *Biomaterials* 19: 1441-1445 (1998).

Fadeev et al. "Surface Modification of Poly(ethylene trephthalate) to Prepare Surfaces with Silica-Like Reactivity" *Langmuir* 14: 5586-5593 (1998).

Ghosh et al. "Covalent Grafting of a Patterned, Hyperbranched polymer onto a Plastic Substrate using Microcontact Printing" *J Am Chem Soc* 121: 8395-8396 (1999).

Hengsakul et al. "Protein Patterning with a Photoactivatable Derivative of Biotin" *Bioconjugate Chem* 7: 249-254 (1996).

Hermanson *Bioconjugate Techniques* pp. 90-100, 152-154 Academic Press San Diego, CA (1996).

International Search Report for application No. PCT/US2001/06547 mailed on Jan. 2, 2002.

Kovacs et al. "Racemization of Amino Acid Derivatives. Rate of Racemization and Peptide Bond Formation of Cysteine Active Esters" *J Org Chem* 35(6): 1810-1815 (1970).

Kumar et al. "Patterned Self-Assembled Monolayers and Meso-Scale Phenomena" *Acc Chem Res* 28: 219-226 (1995).

Lahiri et al. "Patterning Ligands on Reactive SAMs by Microcontact Printing" *Langmuir* 15: 2055-2060 (1999).

Lofas et al. "A Novel Hydrogel Matrix on Gold Surfaces in Surface Plasmon Resonance Snsors for Fast and Efficient Covalent Immobilization of Ligands" *J Chem Soc, Chem Commun* pp. 1526-1528 (1990).

Massia et al. "Covalent Surface Imobilization of Arg-Gly-Asp- and Tyr-Iie-Gyl-Ser-Arg- Containing Peptides to Obtain Well-Defined Cell-Adhesive Substrates" *Analytical Biochemistry* 187: 292-301 (1990).

Massia et al. "Covalently Attached GRGD on Polymer Surfaces Promotes Biospecific Adhesion of mammalian Cells" *Biochemical Engineering VI* Annals of the New York Academy of Sciences 589: 261-270 (1990).

Massia et al. "Human Endothelial Cell Interactions with Surface-coupled Adhesion Peptides on a Nonadhesive Glass Substrate and two Polymeric Biomaterials" *J Biomedical Materials Research* 25: 223-242 (1991).

Mooney et al. "Patterning of Functional Antibodies and Other Proteins by P Hotolithography of Silane Monolayers" *Proc Natl Acad Sci USA* 93: 12287-12291 (1996).

Mougenot et al. "Reactivity Assays of Surface Hydroxyl Chain Ends of Poly(ethylene terephthalate) (PET) Film and Membranes Using Original $^3$H- and Flourine-Labeled Derivatization Reagents" *Macromolecules* 29: 3552-3559 (1996).

Mougenot et al. "Surface Functionalized of Polyethylene Terephthalate Film and Membranes by Controlled West Chemistry" *J of Colloid and Interface Science* 177: 162-170 (1996).

Mrksich et al. "Patterning Self-Assembled Monolayers Using Microcontact Printing: A New Technology for Biosensors?" *TIBTECH* 13: 228-235 (1995).

Mrksich et al. "Using Microcontact Printing to Pattern the Attachment of Mammalian Cells to Self-Assembled Monolayers of Alkanethiolates on Transparent Films of Gold and Silver" *Experimental Cell Research* 235: 305-313 (1997).

Ratner et al. "Plasma Deposition and Treatment for Biomaterial Applications" *Plasma Deposition, Treatment and Etching of Polymers*; Riccardo d'Agostino, editor; chapter 7: 463-516.

Schwarz et al. "Micropatterning of Biomolecules on Polymer Substrates" *Langmuir* 14: 5526-2231 (1998).

Shakesheff et al. "Creating Biomimetic Micro-Environments with Synthetic Polymer-Peptide Hybrid Molecules" *J Biomater Sci Polymer Edn* 9(5): 507-518 (1998).

Solbrig et al. "Wettability of CsOH- Treated Poly(ethylene Terephthalate) Film" *J Applied Polymer Science, Applied Polymer Symposia* 47: 437-444 (1990).

Wang et al. "An XPS Investigation of Polymer Surface Dynamics. I. A Study of Surfaces Modified by $CF_4$ and $CF_4/CH_4$ Plasmas" *J Applied Polymer Sciences* 50: 585-599 (1993).

Whitesides et al. "Wet Cehmical Approaches to the Characterization of Organic Surfaces: Self-Assebled Monolayers, Wetting, and the Physical-Organic Chemistry of the Solid-Liquid Interface" *Langmuir* 6: 87-96 (1990).

Wilbur et al. "Microfabrication by Microcontact printing of Self-Assembled Monolayers" *Advanced Materials* 6(7/8): 600-604 (1994).

Wybourne "Creation of Biomolecule Arrays by Electrostatic Immobilization on Electron-Beam-Irradiated Polystyrene Thin Films" *Nanotechnology* 7: 302-305 (1996).

Xia et al. "Soft Lithography" *Angew Chem Int Ed* 37: 550-575 (1998).

Yao et al. "Surface Modification by Continuous Graft Copolymerization. III. Photoinitiated Graft Copolymerization onto Poly(ethylene Terephthalate) Fiber Surface" *J Applied Polymer Sciences* 41: 1459-1467 (1990).

* cited by examiner

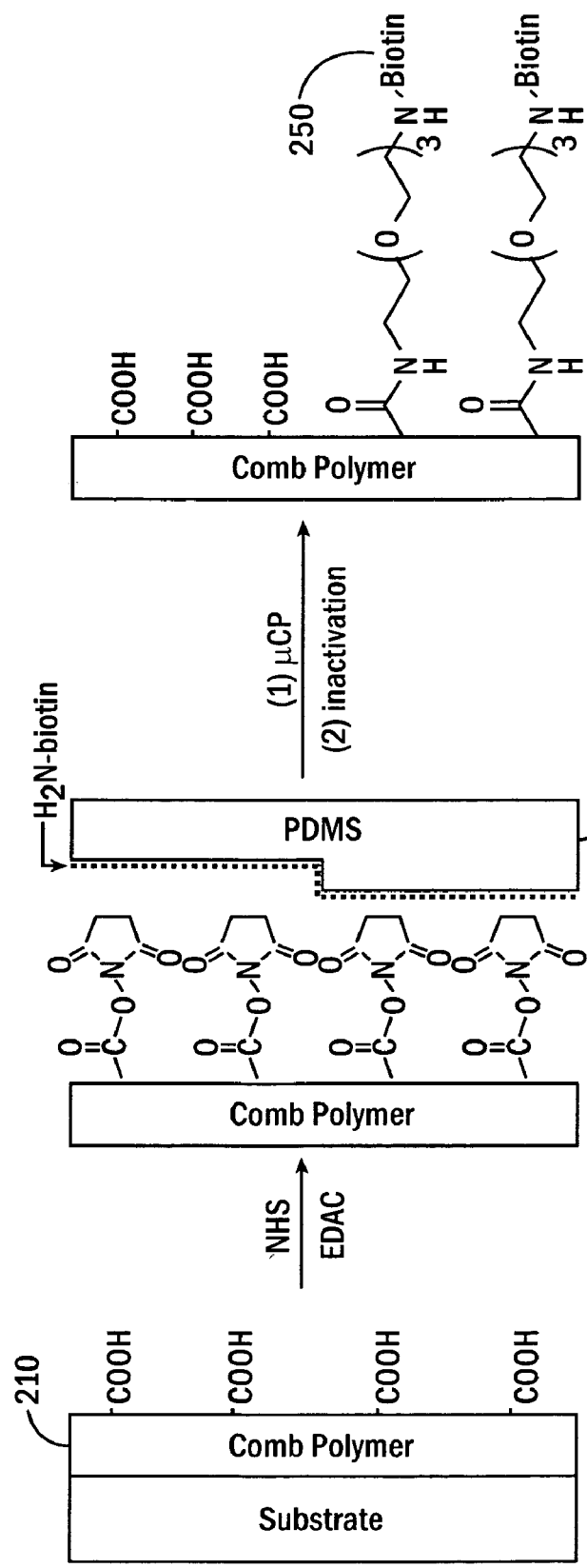

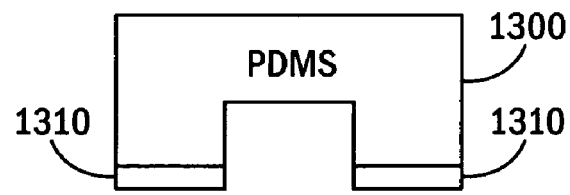
Inking Comb
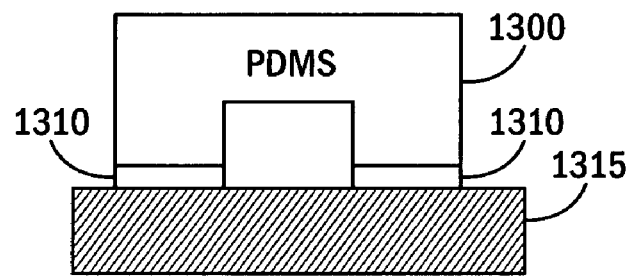
FIG. 18A
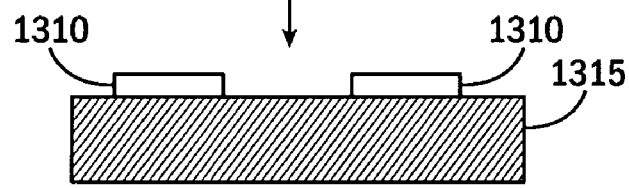
FIG. 18B
FN adsorption
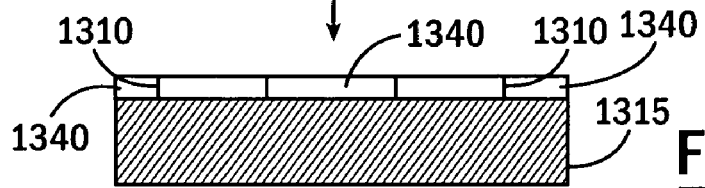
FIG. 18C
Cell Seeding

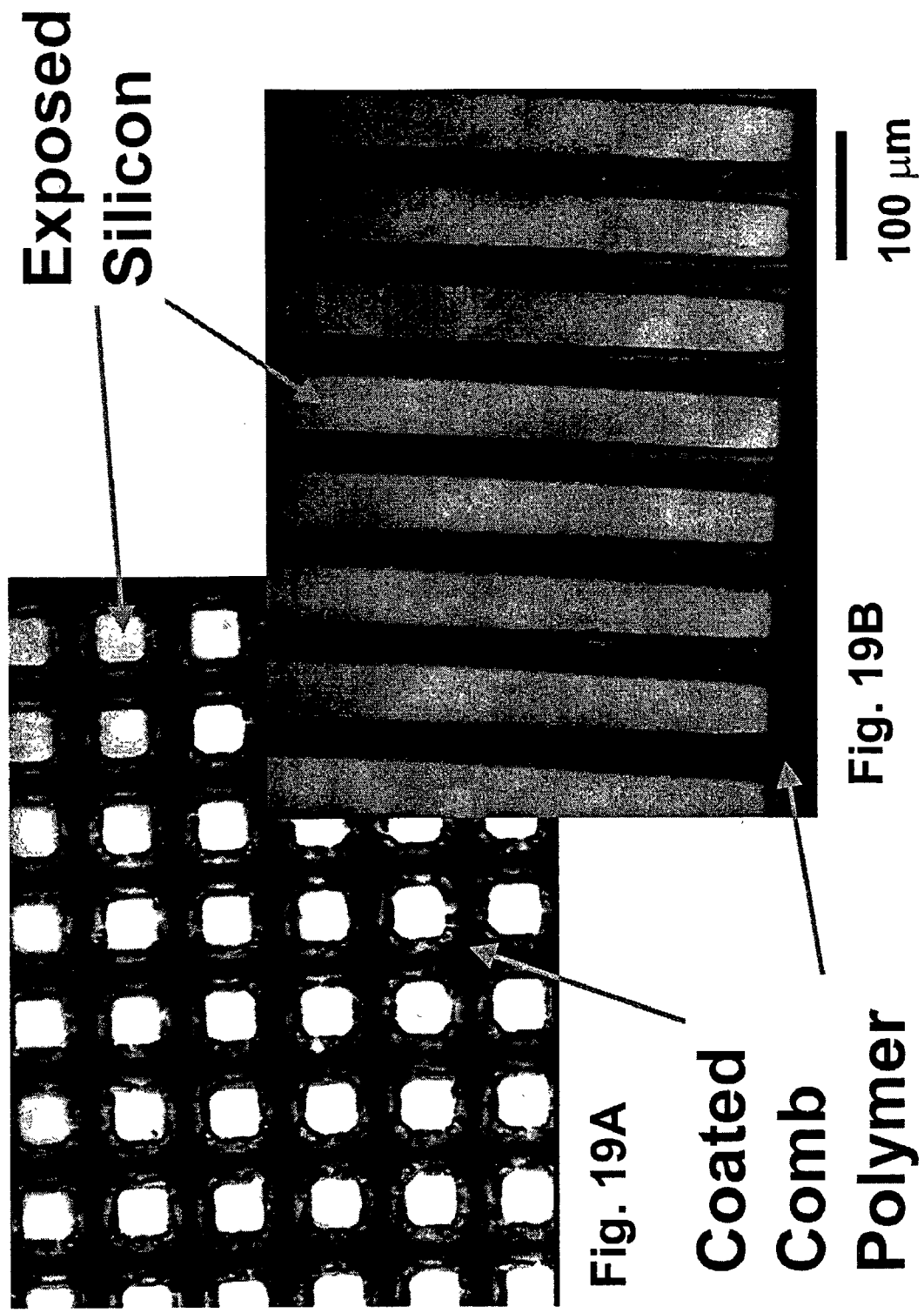

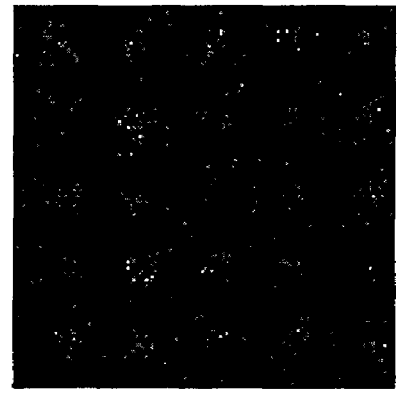
Fig. 20C  C₂H₆N⁺ — rendered as $C_2H_6N^+$
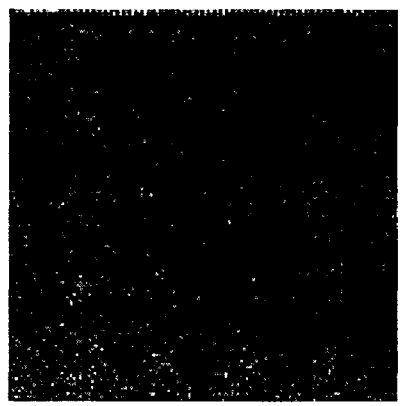
Fig. 20B  $CN^-$
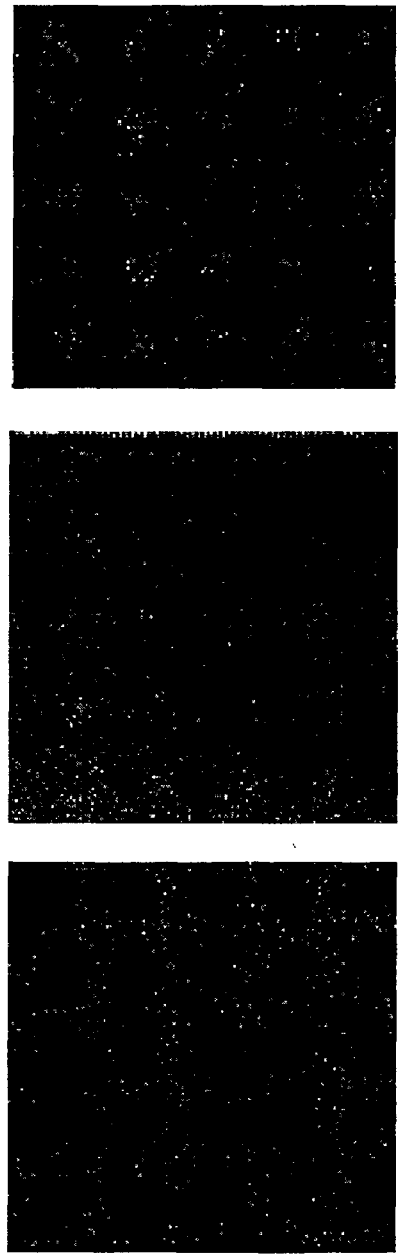
Fig. 20A  $CH_3O^+$
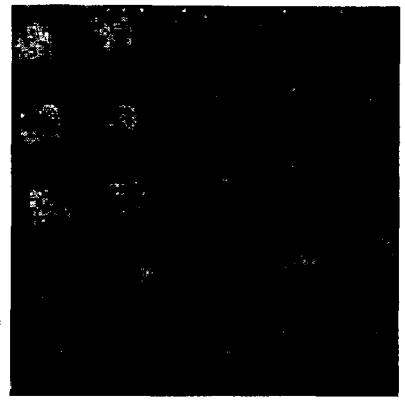
Fig. 21C  $CNO^-$
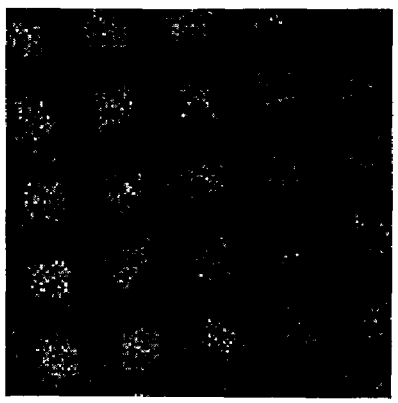
Fig. 21B  $CN^-$
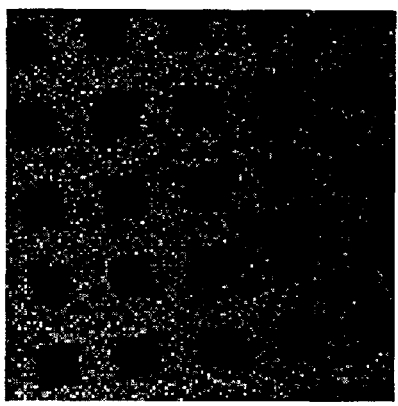
Fig. 21A  $CH_3O^-$

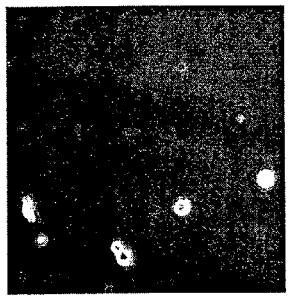
Fig. 22A
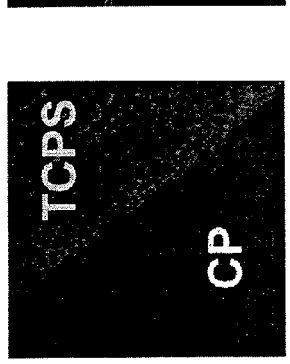
Fig. 22B
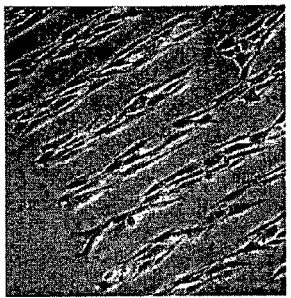
Fig. 22C PS
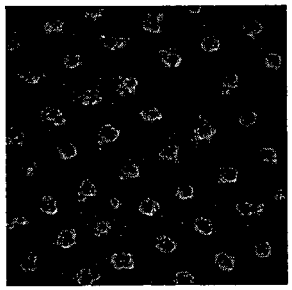
Fig. 22D PET
Fig. 22E PMMA
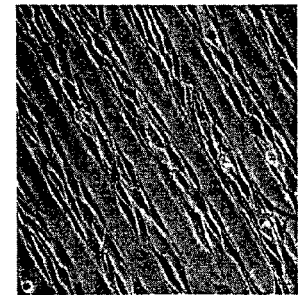
Fig. 22F
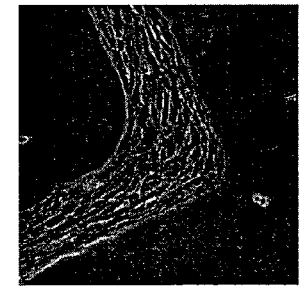
Fig. 22G
Fig. 22H
100 μm

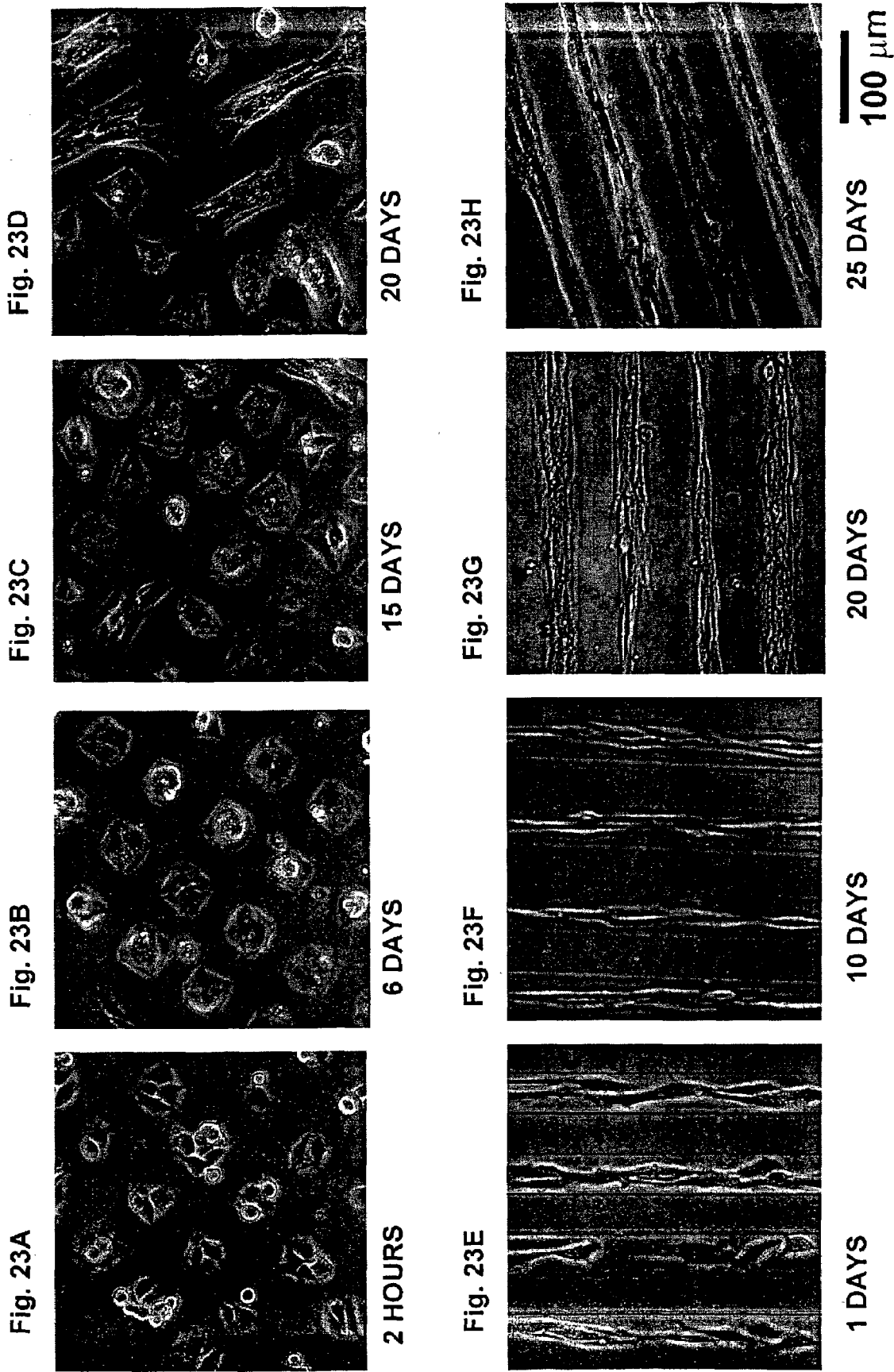

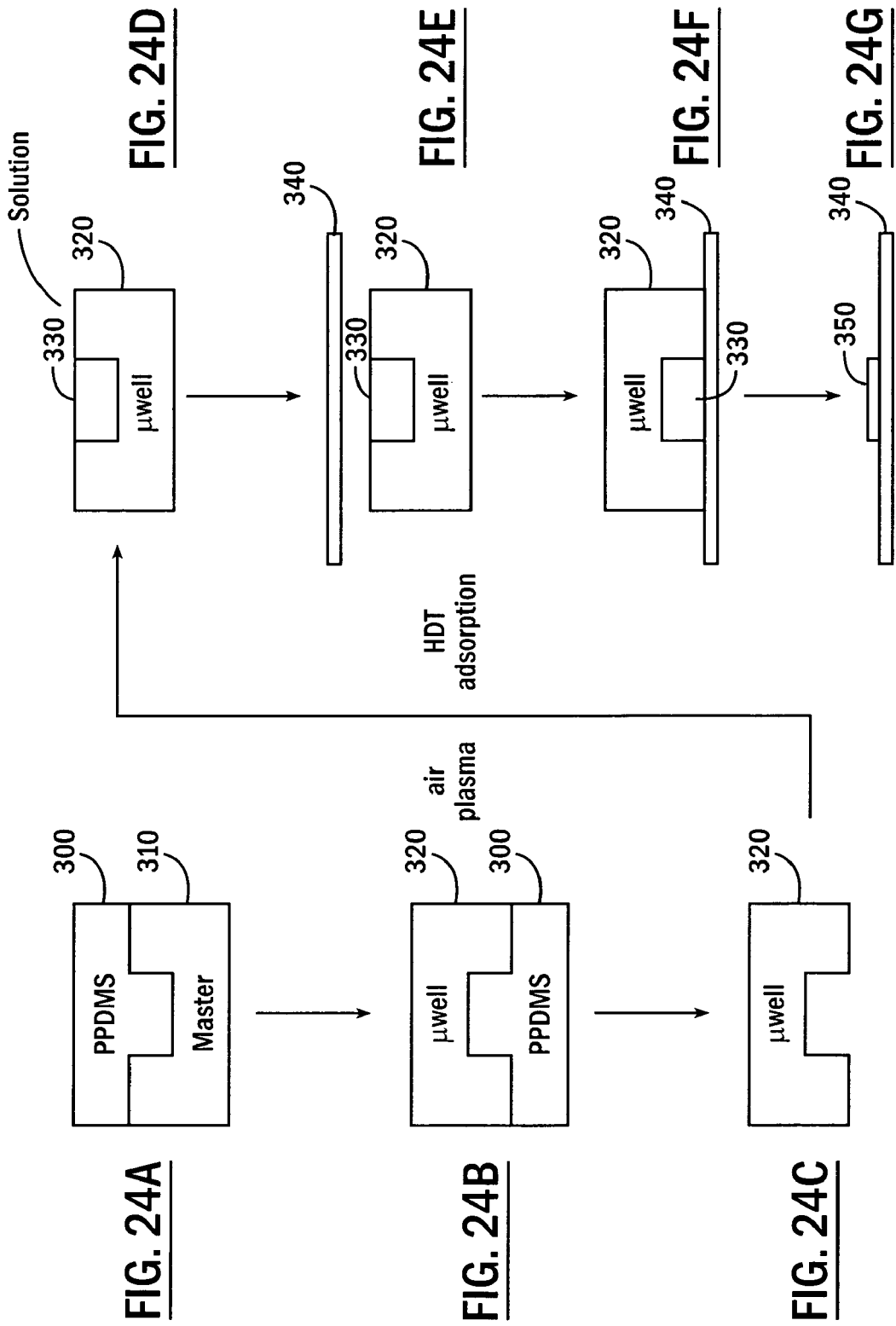

MICROSTAMPING ACTIVATED POLYMER SURFACES

CROSS-REFERENCE TO RELATED APPLICATIONS

The present application is a continuation-in-part application of Ser. No. 09/519,038, filed Mar. 3, 2000, now U.S. Pat. 6,444,254, the disclosure of which is incorporated herein by reference in its entirety.

FIELD OF THE INVENTION

This invention relates to methods of microcontact printing.

BACKGROUND OF THE INVENTION

Micropatterning of biomolecules on surfaces has a number of applications, including the modulation of cell-substrate interactions in biomaterials and tissue engineering and the fabrication of multi-analyte biosensors and genomic arrays. See Blawas, A. S. et al, *Biomaterials* (1998), 19, 595; Mrksich, M. and Whitesides, G. M., *TIBTECH* (1995) 13, 228. Microcontact printing (also referred to herein as "µCP") methods are attractive for micropatterning of biomolecules, because of their simplicity and ease of use. See Kumar, A. . et al., *Acc. Chem. Res.* 1995, 28, 219; Xia, Y. et al., *Angew. Chem. Int. Ed. Engl.* (1998), 37, 550. To date, however, methods of microcontact printing have generally been limited to the production of patterns on self assembling monolayers (SAMs), which in turn are bound to gold or silicon surfaces. For example, Whitesides and coworkers have used reactive µCP to pattern biological ligands onto reactive SAMs on gold. J. Lahiri,et al., *Langmuir* 1999, 15, 2055. Bernard et al. have similarly used µCP to pattern different proteins onto SAMs on gold by physical adsorption. See Bernard, A.; et al., *Langmuir* 1998, 14, 2225.

U.S. Pat. No. 5,512,131 to Kumar et al. proposes a method of patterning a surface in which an elastomeric stamp with a stamping substrate surface is coated with a self-assembled monolayer-forming species having a functional group selected to bind to a surface. The stamp is then placed against the surface to leave a self-assembled monolayer of the species originally coated onto the stamp. The description of the invention is, however, limited to the use of self-assembling monolayers. While SAMs are commonly used, the limitation of being required to use them is disadvantageous in that SAMs generally bind only to certain materials such as metals (usually gold), silicon dioxide, gallium arsenide, glass, and the like. The patent fails to provide any example of a non-SAM species being used to bind directly to a surface, nor does the patent recite any examples of microcontact printing onto a material other than gold.

While SAMs on gold are generally used for micropatterning, they have limited utility as biomaterials. In contrast, polymers are widely used as biomaterials. (Zdrahala, R. J., *J. Biomater. Appl.* (1996) 10, 309). Most previous studies on micropatterning on polymers have utilized photolithography. (Mooney, J. F.et al., *Proc. Natl. Acad. Sci.* (*USA*) 1996, 93, 12287. Wybourne, M. N. et al., *Nanotechnology* 1996, 7, 302. Hengsakul, M et al., *Bioconj. Chem.* 1996, 7, 249. Schwarz, A.et al., *Langmuir* 1998, 14, 552; Dewez, J.-L.et al., *Biomaterials* 1998, 19). Alternative methods have also been demonstrated by Ghosh and Crooks, who patterned hyperbranched poly(acrylic acid) on oxidized poly(ethylene) using reactive µCP. (Ghosh, P.; Crooks, R. M. *J. Am. Chem. Soc.*, 1999, 121, 8395).

The micropatterning of biological molecules onto surfaces is an important objective because such patterning enables, for example, control of cell-substrate interactions. (Chen, C. S.; et al., *Science* 1997, 276, 1425. Mrksich, M.et al., *Exp. Cell Res.* 1997, 235, 305. Chen, C. S;et al., Whitesides, G. M.et al., *Biotechnol. Prog.* 1998, 14, 356). In the last decade, biomolecules have been immobilized onto the surface of different polymers in order to modulate their interaction with cells. (Shakesheff, K.et al., *J. Biomater. Sci., Polym. Ed.* 1998, 9, 507; Cima, L. G., *J. Cell. Biochem.* 1994, 56, 155; Massia, S. P. et al., *J. Biomed. Mater. Res.* 1991, 25, 223; Brandley, B. K.; et al., *Anal. Biochem.* 1988, 172, 270. Massia, S. P. et al., *Anal. Biochem.* 1990, 187, 292). More recent studies have focused on patterning polymer surfaces with biological ligands. Mooney, J. F.; Hunt, et al., *Proc. Natl. Acad. Sci.* (*USA*) 1996, 93, 12287. Wybourne, M. N.et al., *Nanotechnology* 1996, 7, 302; Hengsakul, M.et al., *Bioconj. Chem.* 1996, 7, 249; Schwarz, A.; et al., *Langmuir* 1998, 14, 5526; Dewez, J.-L.et al., P. G. *Biomaterials* 1998, 19).

Despite the foregoing, current attempts to micropattern biological ligands onto polymer surfaces are severely limited. Most µCP methods are done and indeed are required to be performed on gold or similar metal surfaces. Typically, a SAM-molecule is stamped onto a gold surface to create a patterned SAM layer on the gold surface. See Kumar, A. .et al., supra. In a modification of this basic method, Lahiri et al., supra, have developed a method in which a homogeneous SAM is formed on gold by incubating the gold surface in a solution of the SAM-forming molecules. Next, a stamp is used to transfer a non-SAM reactive molecule to the SAM/gold surface. The reactive molecule reacts with a reactive molecule in the SAM to form a pattern of the reactive molecule on the SAM/gold surface. These methods are limiting because they are restricted to the use of gold or other SAM forming surfaces, and require the use of SAM-forming molecules. These approaches are not applicable to polymer surfaces because SAMs do not generally form on polymers. In yet another alternative approach (Bernard et al., supra), a stamp "inked" with protein is used to stamp a pattern of the protein onto a polymer. A significant limitation of this method is that the protein is not bound to the polymer surface via a stable, covalent linkage or bond. Rather, the protein is attached to the polymer surface by physical adsorption. This approach is limiting because many molecules of interest cannot be stably bound to polymer surfaces by non-specific physical adsorption, and the patterned molecule is easily removed from the polymer surface by water, buffers, biological fluids and the like.

In addition to the above, it has become increasingly important to attempt to control the placement of cells in an organized pattern on a substrate for the development of cellular biosensors, biomaterials, and high-throughput drug screening assays. See e.g., R. Singhvi, G. Stephanopoulos, D. I. C. Wang, *Biotechnology and Bioengineering* 1994, 43, 764, J. A. Hammarback, S. L. Palm, L. T. Furcht, P. C. Letourneau, *J. Neurosci. Res.* 1985, 13, 213, and K. E. Healy,B. Lom, P. E. Hockberger, *Biotechnology and Bioengineering* 1994, 43, 792. A potential problem in spatially directing cellular interactions at a biomaterial surface is the relatively rapid adsorption of a complex layer of proteins within a relatively short period of time of contact with serum in cell culture or upon implantation in vivo. See e.g., T. A. Horbett, J. L. Brash, *ACS Sym. Ser.* 1987, 343, 1.; J. D. Andrade, V. Hlady, S. I. Jeon, in *Hydrophilic polymers:*

*Advances in Chemistry Series,* Vol. 248 (Eds: J. E. Glass), ACS, Washington, D.C. 1996, p 51. The adsorbed layer of proteins may potentially physically obscure the micropatterned cell-adhesive ligand, or present a multitude of alternative cellular signals, which has the ability to prevent the formation of cellular patterns, mediated by the micropatterned cell-adhesive ligand.

One proposed approach to address this problem involves the presentation of a biochemical ligand of interest against a protein-resistant, nonfouling surface. A method to prevent nonspecific protein adsorption involves the incorporation of polyethylene glycol (PEG) at the surface. A number of methods have been proposed to incorporate PEG at surfaces, including physisorption (e.g., J. H. Lee, P. Kopeckova, J. Kopecek, J. D. Andrade, *Biomaterials,* 1990, 11, 455; J. A. Neff, K. D. Caldwell, P. A. Tresco, *J. Biomed. Mater. Res.* 1998, 40, 511), chemisorption (e.g., K. L. Prime, G. M. Whitesides, *Science* 1991, 25215, 1164.; K. L. Prime, G. M. Whitesides, *J. Am. Chem. Soc.* 1993, 115, 10714), chemical grafting (e.g., J. M Harris, in *Polyethyleneglycol Chmistry; bioechnicqal and Biomedical Applications:* Plenum Press, New York, 1992; K. D. Park, W. G. Kim, H. Jacobs, T. Okano, S. W. Kim, *J. Biomed. Mater. Res.,* 1992, 26, 739.; Y. C. Tseng, K. Park, *J. Biomed. Mater Res.* 1992, 26, 373.; M. Amiji, K. Park, *J. Biomater.Sci., Polym. Ed.* 1993, 4, 217), plasma-initiated grafting (e.g., M. S. Sheu, A. S. Hoffman, J. G. A. Terlingen, J. Feijen, *Clin. Mater.* 1993, 13, 41), and deposition (e.g., G. P. Lopez, B. D. Ratner, C. D. Tidwell, C. L. Haycox, R. J. Rapoza, T. A. Horbett, *J. Biomed. Mater. Res.* 1992, 26, 415). Most of these methods, however, typically require multiple processing steps that are often optimized for the surface of interest.

Thus, the successful patterning of biological ligands directly onto polymer surfaces using reactive microstamping techniques (e.g., in which reactions between the ligands and the polymer surfaces occur to create a stable covalent bond between the two) has heretofore remained elusive. Accordingly, a need exists for a reliable method of microstamping biological and other ligands directly and covalently onto polymer surfaces that may render the surface biologically nonfouling.

SUMMARY OF THE INVENTION

Embodiments of the present invention provide methods of reactive microcontact printing (μCP) that may overcome many of the shortcomings presented by the conventional methods described above. In a preferred embodiment, these methods enable biological ligands and proteins to be directly patterned onto polymers such that the resulting pattern has a spatial resolution of at least 5 μm and good reproducibility. In other embodiments of the methods according to the present invention may provide spatial control of ligand presentation on the surface of commonly used polymeric biomaterials.

According to embodiments of the present invention, methods of attaching a ligand to a surface include contacting a surface having an amphiphilic comb polymer present thereon, the amphiphilic comb polymer having a first reactive moiety attached thereto, with a substrate having at least one ligand thereon, the ligand comprising a second reactive moiety, wherein the second reactive moiety of the ligand and the first reactive moiety of the amphiphilic comb polymer form a covalent bond; and then separating the substrate from the surface, thereby leaving the ligand covalently bound to the amphiphilic comb polymer.

In other embodiments of the present invention, methods of attaching a ligand to a surface include contacting a surface with a substrate containing an amphiphilic comb polymer, wherein the substrate is configured to provide a pattern of the amphiphilic comb polymer on a selected region of the surface; separating the substrate from the surface, thereby leaving the amphiphilic comb polymer on the selected region of the surface; and then depositing a ligand on the surface such that the selected region of the surface having the amphiphilic comb polymer thereon is substantially free of the ligand.

In still further embodiments, methods of attaching a ligand to a surface include depositing at least one ligand on a surface; contacting the surface having the ligand present thereon with a substrate having an amphiphilic comb polymer thereon; and then separating the substrate from the surface, thereby leaving the amphiphilic comb polymer bound to the ligand. The bond can be physical or chemical.

The foregoing and other aspects of the present invention are explained in detail in the specification set forth below.

BRIEF DESCRIPTION OF THE DRAWINGS

FIG. 4A is a schematic of the patterned area, showing the location of regions from which the fluorescence images in panels 4B, 4C and 4D were taken.

In FIG. 7B, the map of the $C_6F_5O^-$, the PFP molecular anion (m/z 183$^-$), shows that PFP is preferentially located in the unstamped regions. The map of the molecular ion (m/z 227$^+$) corresponds well with the CN$^-$ map (FIG. 7C). In FIG. 7D, the map of the m/z 104 molecular ion of PET indicates that PET is preferentially exposed in the unstamped regions. Images shown in FIGS. 7A and 7B were acquired from the same area, and the images in FIGS. 7C and 7D were acquired from different areas.

FIG. 8A is the molecular map of m/z 104 ion ($C_7H_4O^+$) shows that PET is exposed in the unstamped regions. The characteristic streptavidin ion m/z 70 ion ($C_4H_8N^-$) in FIG. 8B shows that streptavidin binds preferentially to the stamped biotin pattern. FIG. 8C shows that residual Tween 20™ is preferentially adsorbed to the unstamped regions.

FIG. 9A and 9C m/z 104 ($C_7H_4O^+$ ion from PET surface); FIG. 9B and 9D m/z 26 (CN$^-$). The square 10 μm biotin pattern in images of FIG. 9A and 9B included Tween 20™ in the streptavidin binding buffer, and show that streptavidin binds preferentially to the biotinylated regions with low nonspecific adsorption of protein to the background. In contrast, the square 40 μm biotin pattern in images shown in FIGS. 9C and 9D did not include Tween 20™ in the streptavidin solution, and show significant nonspecific adsorption of streptavidin to the patterned surface.

FIG. 13A, 13B and 13C are schematic diagrams of embodiments of micropatterning techniques in accordance with the present invention.

FIG. 14A is Alexa488-labeled streptavidin on PET. FIG. 15A is biotin-GRGDSP-(K-TMR) peptide incubated with a streptavidin micropattern on PET.

FIGS. 17 and FIGS. 18A, 18B and 18C are schematic diagrams of embodiments of micropatterning techniques in accordance with the present invention.

FIGS. 19A and 19B illustrate the reflection image of a silicon surface micropatterned with an amphiphilic comb polymer as visualized by optical microscopy.

FIGS. 20A, 20B and 20C and FIGS. 21A, 21B, and 21C show TOF-SIMS images of comb polymer patterns combined with FN.

FIG. 22A illustrates the cell repellent, "nonfouling" effect of the comb polymer spincast on tissue culture polystyrene (TCPS).

FIG. 22B illustrates that cells did not attach on the normal hydrophobic PS surface with a serum-containing medium as on comb polymer surface.

FIGS. 22C illustrates aligned cell micropatterns of fibroblasts on a surface of PS adsorbed with FN, onto which a comb polymer was micropatterned.

FIGS. 22D illustrates aligned cell micropatterns of fibroblasts on a surface of PET adsorbed with FN, onto which a comb polymer was micropatterned.

FIGS. 22E illustrates aligned cell micropatterns of fibroblasts on a surface of PMMA adsorbed with FN, onto which a comb polymer was micropatterned.

FIG. 22F, 22G and 22H shows micropatterns of a comb polymer printed on an FN-adsorbed surface and the resulting attachment of cells.

FIGS. 23A, 23B, 23C, 23D, 23E, 23F, 23G and 23H show time dependent cell patterning using an amphiphilic comb polymer.

FIGS. 24A, 24B, 24C, 24D, 24E, 24F and 24G are a schematic illustrations of embodiments micropatterning techniques using elastomeric microwell reservoirs.

FIG. 25A illustrates square microwells and FIG. 25B illustrates microchannels.

DETAILED DESCRIPTION OF THE PREFERRED EMBODIMENTS

Figure 1:
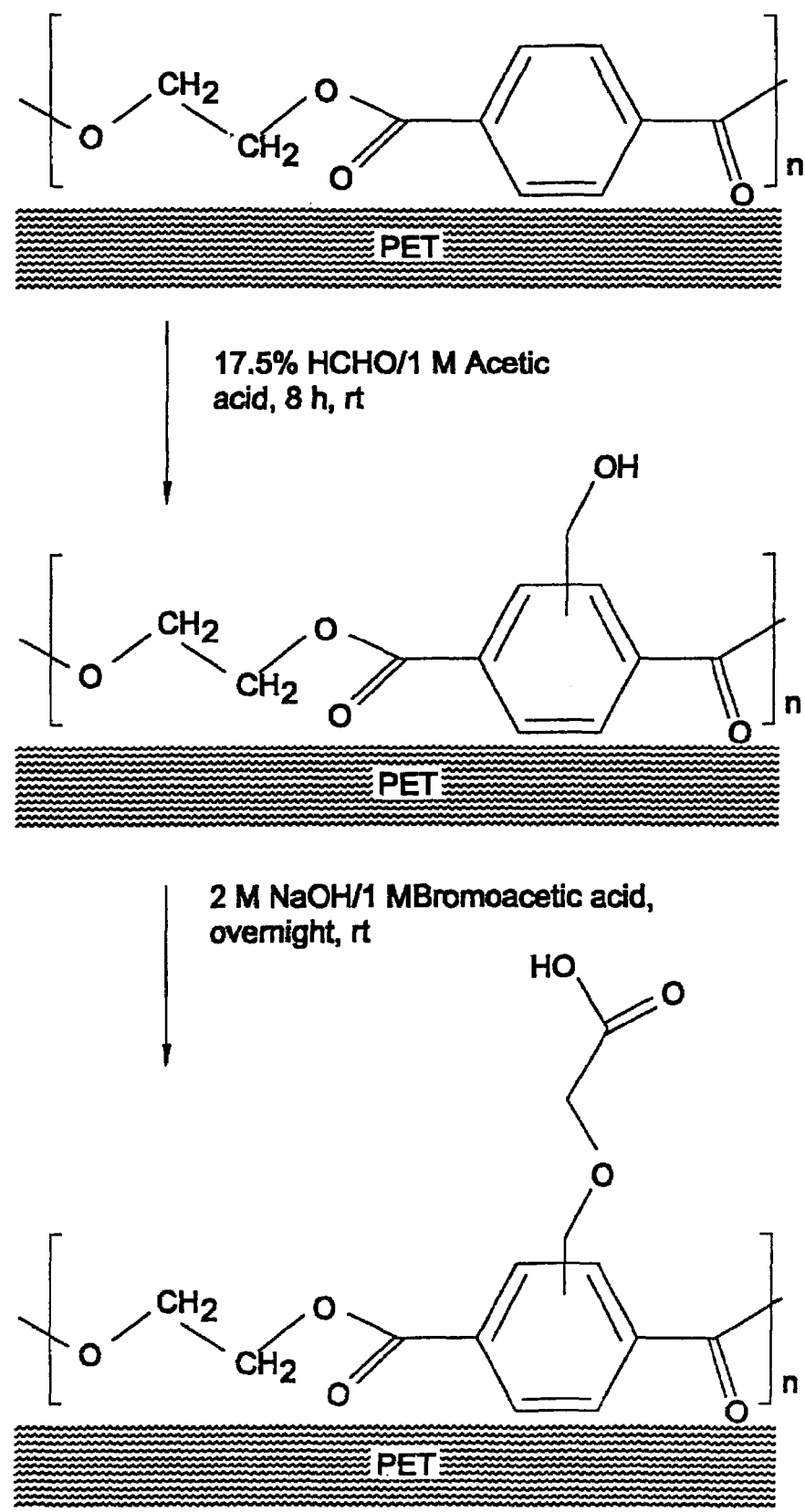
FIG. 1 is a schematic of surface chemical derivatization to introduce carboxylic acid groups in PET.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Polymers useful as the polymeric surfaces according to embodiments of the present invention may be natural polymers (e.g., biological polymers) or synthetic polymers. For ease of discussion, the surfaces described herein may be described as polymeric surfaces. However, other surfaces known to those of ordinary skill in the art onto which a comb polymer can form a stable coating may be used. For example, other surfaces that may also be used include metals, metal oxides, semiconductors, ceramics, and other composites, e.g., any material onto which a comb polymer can be shown to form a stable coating in water or other biologically relevant liquid, such as a cell culture medium, serum, plasma, or an exudate at an implant site. Synthetic polymers that may be used in the present invention include but are not limited to known synthetic polymers such as poly(ethylene terephthalate) (PET), polystyrene (PS), polycarbonate (PC), poly(epsilon-caprolactone) (PECL or PCL), poly(methyl methacrylate) (PMMA), poly(lactic acid) (PLA), polydimethylsiloxane (PDMS), polybutadiene (PB), polyvinylalcohol (PVA), fluorinated polyacrylate (PFOA), poly(ethylene-butylene) (PEB), and poly(styrene-acrylonitrile) (SAN). Polymers according to the present invention also encompass biological polymers, such as peptides, proteins, and repeating units of nucleic acid (i.e., DNA and RNA). In any event, the term "polymer" will be defined herein as a compound or molecule comprising at least two units of a monomer or repeating unit, as these terms are understood in the art. The term "polymer" as used herein is also intended to encompass a homopolymer, heteropolymer, co-polymer, ter-polymer, etc., and blends, combinations and mixtures thereof.

Ligands referred to herein are preferably biological ligands, although non-biological ligands such as synthetic polymers that are naturally reactive or functionalized to be reactive with other reactive groups or functional groups are also encompassed by this term. Biological ligands of the present invention include but are not limited to proteins, peptides, nucleic acids, carbohydrates, lipids, polysaccharides, and other biological molecules. Biological molecules may include, for example, biotin, vitamins, cofactors, coenzymes, receptor agonists or antagonists, etc. The biological ligand may selectively bind various biological or other chemical species such as proteins, antibodies, antigens, sugars and other carbohydrates, and the like. Moreover, the biological ligand may comprise a member of any specific or non-specific binding pair, such as either member of the following exemplary list: antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, repressor/inducer, or the like.

Non-biological ligands of the present invention include synthetic polymers and plastics which are known in the art.

Certain embodiments of methods described according to the present invention are sometimes referred to herein by the acronym "MAPS," an abbreviation for Microstamping onto an Activated Polymer Surface. The method involves functionalized polymer surfaces having reactive moieties (also referred to as "reactive groups" or "functional groups" herein) on the surface of the polymer. The functionalized polymer surface is contacted with a stamp having on its surface ligands comprising reactive moieties that react with the reactive moieties on the polymer surface to produce a covalent bond.

In one aspect, embodiments of the present invention provide methods of attaching a ligand to a polymer surface. The method comprises contacting a surface having an amphiphilic comb polymer present thereon, the amphiphilic comb polymer having a first reactive moiety attached thereto, with a substrate having at least one ligand thereon, the ligand comprising a second reactive moiety, wherein the second reactive moiety of the ligand and the first reactive moiety of the amphiphilic comb polymer form a covalent bond; and then separating the substrate from the surface, thereby leaving the ligand covalently bound to the amphiphilic comb polymer. The methods described herein may be particularly advantageous in that in certain embodiments, the presence of the amphiphilic comb polymer has the ability to minimize or prevent the non-specific adsorption of proteins onto a surface. Moreover, in a preferred embodiment, the polymeric surface can be modified in a one-step process in which the biological ligand is attached thereto.

Figure 10:
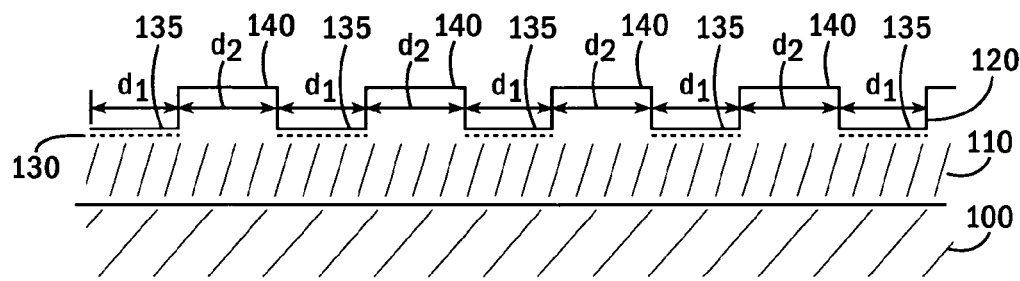
FIG. 10 illustrates embodiments of delivering biological ligand to a polymeric surface having a plurality of amphiphilic comb polymers attached thereto in accordance with the present invention.

In some embodiments, the contacting step comprises impressing a stamp having at least one biological ligand present thereon, which biological ligand comprises a second reactive moiety to the polymer surface such that the at least one biological ligand is covalently bound to the amphiphilic comb polymer. In these embodiments, the stamp is the substrate and the at least one biological ligand is attached to the surface of the stamp. This embodiment is illustrated in greater detail in FIG. 10 with a polymeric surface 100 having a plurality of amphiphilic comb polymers 110 attached thereto. A stamp 120 is configured such that it may be impressed upon the polymeric surface, and is made up of a series of protrusions 135 and wells 140. The dimension $d_1$ of a protrusion 135 preferably ranges from about 0.1, 0.2, 0.3, 0.4, 0.5, 0.6, 0.7, 0.8, 0.9, 1, 3, 5, 10, 15, 20, 25, 30, 35, 40, or 45 microns to about 50, 55, 60, 65, 70 75, 80, 85, 90, 95 or 100 microns, and the dimension of $d_2$ of a well 140 preferably ranges from about 0.1, 0.2, 0.3, 0.4, 0.5, 0.6, 0.7, 0.8, 0.9, 1, 3, 5, 10, 15, 20, 25, 30, 35, 40, or 45 microns to about 50, 55, 60, 65, 70 75, 80, 85, 90, 95 or 100 microns. Biological ligands 130 are present on the surface of protrusions 135 and are thereafter brought into contact with and covalently bonded to the comb polymers 110 in a manner described herein.

Figure 11:
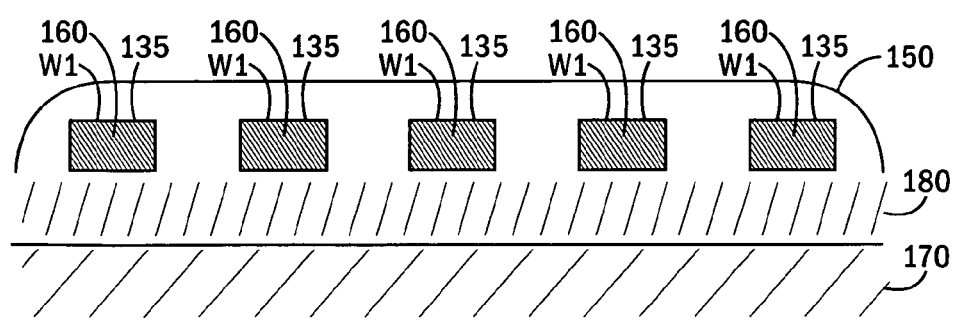
FIG. 11 illustrates embodiments of delivering biological ligand to a polymeric surface using a substrate that includes a plurality of wells in accordance with the present invention.

In different embodiments, the substrate comprises at least one well and an aqueous solution which comprises the at least one biological ligand is present in the at least one well. An illustration of such embodiments is provided in FIG. 11. As shown in FIG. 11, a substrate 150 includes a plurality of wells 155 formed therein. The width $w_1$ of such wells 155 preferably ranges from about 0.1, 0.2, 0.3, 0.4, 0.5, 0.6, 0.7, 0.8, 0.9, 1, 3, 5, 10, 15, 20, 25, 30, 35, 40, or 45 microns to about 50, 55, 60, 65, 70 75, 80, 85, 90, 95 or 100 microns. Each well 155 may contain aqueous solution 160 having biological ligand present therein. The substrate 150 is configured to impress upon or contact a polymeric surface 170 having a plurality of comb polymers 180 attached thereto, such that the aqueous solution 160 delivers biological ligand to surface 170. The biological ligand in the aqueous solution 160 is then bound to some of the plurality of comb polymers 180.

Preferably, the substrate is configured to provide a pattern of the at least one biological ligand on the polymer surface. In an embodiment, the pattern dimensions range from about 0.1, 0.5, 1, 5, 10, 50, 100, 150, or 200 μm to about 250, 300, 350, 400, 450, or 500 μm. The pattern dimensions can be the same as the dimensions for the width of the wells described above. The term "pattern dimensions" refers to the dimensions of a particular pattern formed or the spaces between the pattern. For example, the dimensions of a pattern of stripes are either the width of the stripes or the distance between the stripes and the dimensions of a pattern of rectangles are the length or width of the rectangles or the distance between the rectangles.

Figure 17:
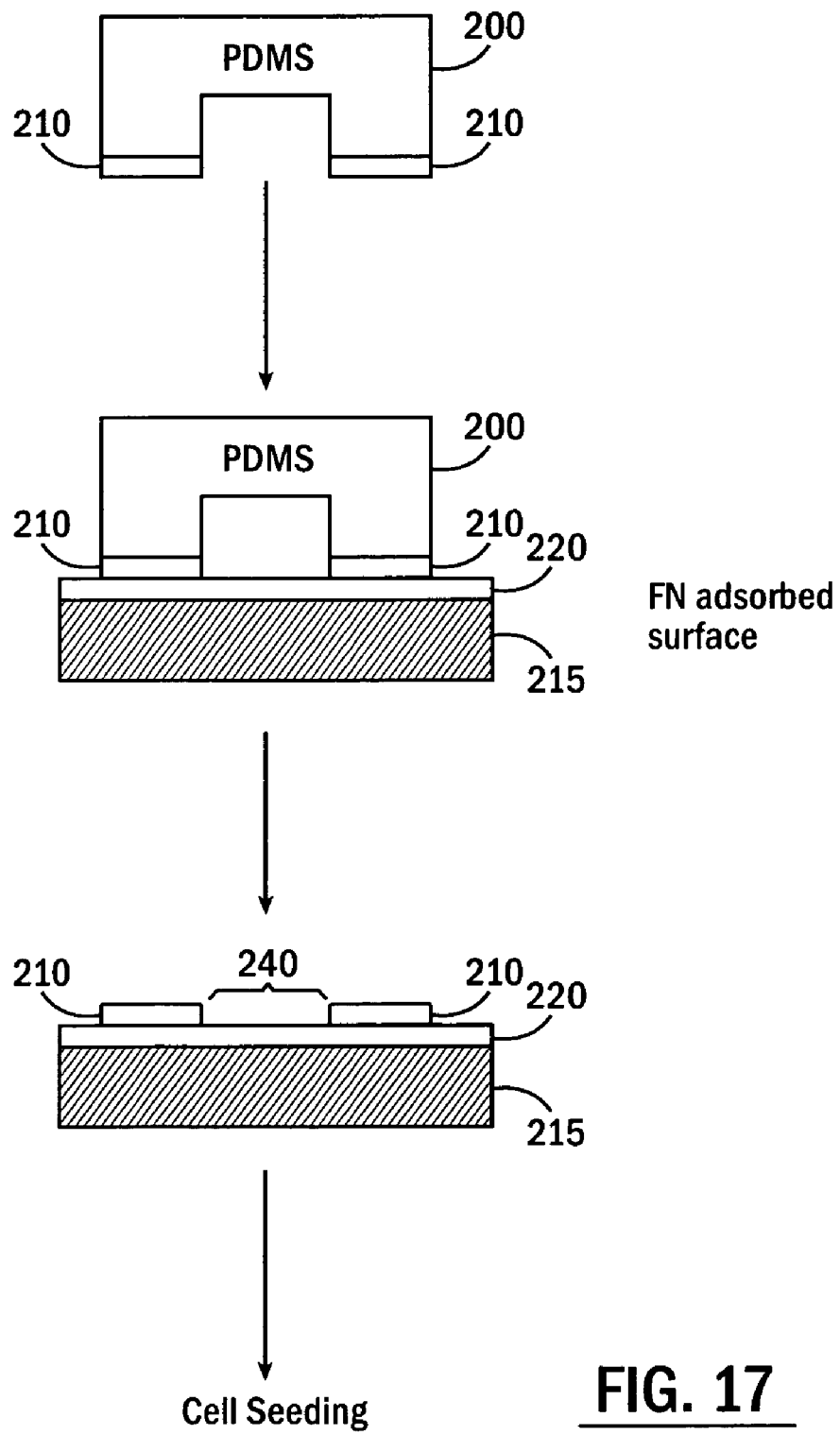

In other embodiments of the present invention, methods of attaching a ligand to a surface include contacting a surface with a substrate containing an amphiphilic comb polymer, wherein the substrate is configured to provide a pattern of the amphiphilic comb polymer on a selected region of the surface; separating the substrate from the surface, thereby leaving the amphiphilic comb polymer on the selected region of the surface; and then depositing a ligand on the surface such that the selected region of the surface having the amphiphilic comb polymer thereon is substantially free of the ligand. Certain embodiments are illustrated in FIG. 17. As shown in FIG. 17, a stamp such as a poly(dimethyl siloxane) (PDMS) stamp 200 includes a comb polymer 210. The stamp 200 is applied to a polymer surface 215 to which a biological ligand 220 has been applied. The stamp 200 is separated from the polymer surface 215 and the comb polymer 210 is deposited on the biological ligand 220 to form a patterned surface including exposed areas of the biological ligand 240 and comb polymer 210.

In still further embodiments, a method can include depositing at least one ligand on a surface; contacting the surface having the ligand present thereon with a substrate having an amphiphilic comb polymer thereon; and then separating the substrate from the surface, thereby leaving the amphiphilic comb polymer bound to the ligand. The bond can be physical or chemical. Certain embodiments are depicted in FIGS. 18A–18C. As shown in FIG. 18A a PDMS stamp 1300 includes a comb polymer 1310. The stamp 1300 can be similar to the stamp 200 in FIG. 17. The stamp 1300 is applied to a polymer surface 1315 to deposit the comb polymer 1310 onto the polymer surface 1315 when the stamp 1300 is separated from the polymer surface 1315 as shown in FIG. 18B. A biological ligand can then be applied to the remaining surfaces as shown in FIG. 18C to form biological ligand surfaces 1340 and surfaces having the comb polymer 1310 thereon.

The bond between the ligand and the comb polymer can be various bonds as will be understood by those skilled in the art. For example, the bond between the ligand and the comb polymer can be a reactive bond or a physical bond. As used herein, a reactive bond is a chemical bond such as an ionic, covalent, mixed ionic/covalent, molecular recognition, coordination bond, or chelation bond. A physical bond is a bond dominated by secondary interactions such as hydrogen bonds, van der Waal forces, hydrophobic forces, and the like.

In certain embodiments, the ligand can have a first reactive moiety attached thereto. The amphiphilic comb polymer can comprise a second reactive moiety. The second reactive moiety of the amphiphilic comb polymer and the first reactive moiety of the ligand can form a covalent bond.

In an alternative embodiment, a substrate 150 including a plurality of wells 155 formed therein as depicted in FIG. 11 may be substituted for the stamp 200 shown in FIG. 17 or the stamp 1300 shown in FIG. 18A to deposit the comb polymer. Each well 155 may contain aqueous solution having comb polymer present therein. The substrate 150 is configured to impress upon or contact the polymeric surface 215, such that the aqueous solution 160 delivers comb polymer to the biological ligand 220 on the surface 215. When the substrate 150 is substituted for the stamp 300 in the embodiments of FIGS. 18A–C, the substrate 150 is configured to impress upon or contact the polymeric surface 1315, such that the aqueous solution delivers comb polymer to surface 1315.

Amphiphilic comb polymers are known in the art and are described, for example, in U.S. Pat. No. 6,207,749 to Mayes et al. Preferably, the amphiphilic comb-type polymers, most preferably present in the form of copolymers, contain a backbone formed of a hydrophobic, water-insoluble polymer and side chains formed of short, hydrophilic non-cell binding polymers.

The hydrophilic side chain polymer typically possesses a molecular weight of between 200 and 5000 Daltons. The hydrophobic backbone can be biodegradable or non-biodegradable, depending on the desired application. In one embodiment, it is preferred that the overall molecular weight of the comb copolymer should be above about 10,000 Daltons, more preferably above 20,000 Daltons, and more preferably still above 30,000 Daltons.

The comb copolymers can be prepared using various techniques. In one embodiment, for example, the copolymer is prepared by copolymerizing a hydrophilic macromonomer which contains a polymerizable chain end with a second hydrophobic monomer. Alternatively, a hydrophobic monomer can be copolymerized with a second monomer that includes suitable reactive groups through which the hydrophilic side chains can be grafted to the backbone. Alternatively, a hydrophobic monomer with a suitable reactive side group can be polymerized and a fraction of those reactive side groups can be modified by grafting hydrophilic side chains. A defined percentage of the non-cell binding side chains can be end-capped with a suitable ligand to elicit a specific cellular response.

Hydrophobic polymers used to impart biodegradable properties to the backbones of the comb copolymers are preferably hydrolyzable under in vivo conditions. Suitable biodegradable polymeric units include hydroxy acids or other biologically degradable polymers that yield degradation products -that are non-toxic or present as normal metabolites in the body. Embodiments of such include, without limitation, poly(amino acids), poly(anhydrides), poly(orthoesters), and poly(phosphoesters). Polylactones such as poly(epsilon-caprolactone), poly(delta-valerolactone), poly(gamma-butyrolactone)and poly (beta-hydroxybutyrate), for example, are also useful. Preferred poly(hydroxy acid)s are poly(glycolic acid), poly(DL-lactic acid) and poly(L-lactic acid), poly (DL-sebacic acid) or copolymers of poly(glycolic acid) poly(lactic acid), and/or poly (sebacic acid).

If desired, biodegradable regions can be constructed from monomers, oligomers or polymers using linkages susceptible to biodegradation, such as, for example, ester, peptide, anhydride, orthoester, and phosphoester bonds. Exemplary non-biodegradable, hydrophobic polymers that can be incorporated into the backbone of the comb copolymers include, without limitation, polyalkylenes such as polyethylene and polypropylene, polychloroprene, polyvinyl ethers, polyvinyl esters such as poly(vinyl acetate), polyvinyl halides such as poly(vinyl chloride), polysiloxanes, polystyrene, polyurethanes and copolymers thereof, polyacrylates, such as poly (methyl (meth)acrylate), poly(ethyl (meth)acrylate), poly(n-butyl(meth)acrylate), poly(isobutyl (meth)acrylate), poly (tert-butyl (meth)acrylate), poly(hexyl(meth)acrylate), poly (isodecyl (meth)acrylate), poly(lauryl (meth)acrylate), poly (phenyl (meth)acrylate), poly(methyl acrylate), poly (isopropyl acrylate), poly(isobutyl acrylate), and poly (octadecyl acrylate) (jointly referred to herein as "polyacrylates"), polyacrylamides such as poly(acrylamide), poly(methacrylamide), poly(ethyl acrylamide), poly (ethyl methacrylamide), poly(N-isopropyl acrylamide), poly (n, iso, and tert-butyl acrylamide) and copolymers and mixtures thereof. For the purposes of the invention, these polymers include useful derivatives, including polymers having substitutions, additions of chemical groups, for example, alkyl groups, alkylene groups, hydroxylations, oxidations, and other modifications routinely made by those skilled in the art.

Preferred non-biodegradable polymers include ethylene vinyl acetate, polyacrylates, poly(chloroprene), and copolymers and mixtures thereof The non-cell binding side chains are preferably water-soluble when not attached to the backbone, and, more preferably, are non-ionic. Suitable polymeric side chains include those prepared from poly(ethylene glycol), poly(ethylene oxide), poly(propylene glycol), poly(propylene oxide), partially or fully hydrolyzed poly(vinyl alcohol), poly(vinylpyrrolidone), and dextran and copolymers thereof. It should be appreciated that other side chains can be employed as will be understood by one skilled in the art. Preferably, the side chains comprise poly(ethylene glycol), poly(ethylene oxide), poly(propylene glycol), poly(propylene oxide), or poly(acrylic acids). The hydrophilic side chains may be intrinsically biodegradable or may be poorly biodegradable or effectively non-biodegradable in the body. In the latter two cases, the side chains should be of sufficiently low molecular weight to allow excretion. The preferred molecular weight range is below about 5000 Daltons, more preferably below 2000 Daltons, and most preferably, below about 1000 Daltons. When the polymer is polyethylene glycol, it is preferred that the number of ethylene oxide monomeric units is between about 4 and 20, i.e., an oligoethylene glycol side-chain.

In embodiments wherein double-bond containing monomers are used to prepare the polymer backbone, a preferred method for incorporating the hydrophilic side chains is to use a hydrophilic macromonomer with a reactive double bond at one end which can be randomly incorporated during free radical or other addition polymerization. An example of such a macromonomer is PEG-methacrylate. The density of the non-cell binding, hydrophilic side chains along the polymer backbone is controlled by controlling the relative amounts of the PEG-methacrylate or other suitable macromonomeric unit used.

In those embodiments in which the side groups are end capped with cell-signaling ligands, appropriate functional groups, such as —NH$_2$, —OH, or —COOH are included on the ends of the macromonomers.

In certain embodiments described herein, monomers can be used to form a polymer backbone. The monomers can include two reactive groups, both of which are reacted in order to form the polymer. For example, lactic acid includes two reactive groups, a hydroxy group and a carboxy group. Hydroxy is the preferred reactive group. Although the ends of a polylactic acid polymer include a hydroxy group and a carboxy group, there are no reactive groups along the backbone in the final polymer chain that can be used to form a comb copolymer.

Monomers which contain one or more additional reactive groups need to be incorporated into the polymer backbone, preferably in a random fashion, in order to form the comb-type copolymers when monomers that do not include these reactive groups are used to prepare the polymer backbone. Examples of these types of monomers are well known to those of skill in the art. Preferably, a suitable reactive monomer can be incorporated in the growing polymer chain by participating in the same types of chemical reactions as the growing polymer chain. For example, when lactide is being polymerized using a Lewis acid catalyst, a depsipeptide (cyclic dimer of an amino acid) can be prepared from lysine, in which the epsilon amine group is protected, for example, with a t-boc protecting group. The lysine is incorporated into the polymer, and the protecting group can be removed. The resulting amine groups are reactive with hydrophilic polymers which include leaving groups such as tosylates, tresylates, mesylates, triflates and other leaving groups well known to those of skill in the art.

Alternatively, the reactive monomer can include a leaving group that can be displaced with a nucleophilic group on a hydrophilic polymer. For example, epichlorohydrin can be used during the polymerization step. The monomer is incorporated into the polymer backbone, and the chloride group is present on the backbone for subsequent reaction with nucleophiles. An example of a suitable hydrophilic polymer containing a nucleophilic group is a PEG with a terminal amine group. PEG-NH$_2$ can react with the chloride groups on the polymer backbone to provide a desired density of PEG-ylation on the polymer backbone. Using the chemistry described herein, along with the general knowledge of those of skill in the art, one can prepare polymer backbones which include suitable leaving groups or nucleophiles for subsequent coupling reactions with suitably functionalized hydrophilic polymers.

Polymer surfaces of the present invention are preferably flat or planar, but may be also be curved, cylindrical, or shaped according to the user's needs. For example, the polymer surface may also be corrugated, rugose, concave, convex or any combination of these conformations. The polymer surface may have various shapes such as, but not limited to, a film or sheet of polymer, a strand, a tubing, a sphere, a container, a capillary, a pad, a molded plastic device, or a plastic plate (e.g., a tissue culture plate). The polymer surface may be on prosthetic or implantable device on which it is desired to covalently bond certain ligands, and which ligands may be capable of binding or attracting other compounds or biological matter (e.g., cells, proteins, or other biological materials).

A functionalized polymer surface according to embodiments of the invention can have at least one reactive moiety on its surface. The polymer surface may be functionalized by means known in the art to produce reactive moieties on the surface of the polymer. Reactive moieties known to those of skill in the art include, but are not limited to, amine groups, sulfur-containing functional groups such as thiols, sulfides, disulfides, and the like; silanes and chlorosilanes; carboxylic acids; nitrites and isonitriles; and hydroxamic acids. Additional suitable reactive moieties include acid chlorides, anhydrides, sulfonyl groups, phosphoryl groups, azo, diazo and hydroxyl groups. Presently, —COOH or carboxylic acid groups are preferred. Exemplary reactive moieties may be hydrophobic, hydrophilic, amphipathic, ionic, nonionic, polar, nonpolar, halogenated, alkyl, or aryl. A non-limiting, exemplary list of such reactive moieties includes: —H, —CONH—, —CONHCO—, —NH$_2$, —NH—, —COOH, —COOR, —CSNH—, —NO$_2^-$, —SO$_2^-$, —RCOR—, —RCSR—, —RSR', —ROR—, —PO$_4^{-3}$, —SO$_3^{-2}$, —SO$_3^-$, —NH$_x$R$_{4-x+}$, —NH$_x$R$_{3-x+}$, —COO$^-$, —SOO$^-$, —RSOR—, —CONR'$_2$, —(OCH$_2$CH$_2$)$_n$ OH (where n=1–20, preferably 1–8), —CH$_3$, —PO$_3$H$^-$, -2-imidazole, —N(CH$_3$)$_2$, —NR$_2$, —PO$_3$H$_2$, —CN, —(CF$_2$)$_n$ CF$_3$ (where n=1–20, preferably 1–8), olefins, and the like. In this list, R' is hydrogen or an organic group such as a hydrocarbon or fluorinated hydrocarbon, and R is an organic group such as a hydrocarbon or fluorinated hydrocarbon. Where the reactive moiety contains more than one R, it is to be understood that each R is independently selected. As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups. Alternatively, R may be a biologically active species such as an antigen, antibody, hapten, etc. Additional reactive moieties suitable for use in the present invention may also be found in U.S. Pat. No. 5,079,600, issued Jan. 7, 1992.

Functionalization, as used herein, means a method comprising one or more steps in which a reactive moiety is introduced onto the surface of the polymer. Functionalization may occur in one, two, or even more steps, with each step generally being a chemical or thermal modification of a polymer surface, the end result of which is a surface onto which a reactive group is introduced. For example, when the polymer surface is PET, the PET surface may first be hydroxylated, and then reacted with one or more compounds as known in the art to introduce carboxylic acid moieties onto the surface. The carboxylic acid moities may then be activated (e.g., using pentaflurophenol) in order to make the carboxylic acid group moieties reactive with other reactive moieties. Several methods of introducing reactive groups onto the surface of polymers are known, including hydrolysis (Kumar, D. J.; Srivastava, H. C. *J. Appl. Polym. Sci.* 1987, 33, 455.; Solbrig, C. M. et al., *J. Appl. Polym. Sci.: Appl. Polym. Symp.* 1991, 47, 437; Búi, L. N., et al. *Analyst.* 1993, 118, 463) and reduction (Búi, L. N.et al., *Analyst.* 1993, 118, 463; Chen, W.et al., *Langmuir* 1998, 14, 5586). Other chemical approaches that can be used to introduce reactive groups onto the surface of the polymer are photo-initiated graft polymerization, (Yao, Z. P.; et al., *J. Appl. Polym. Sci.* 1990, 41, 1459) aminolysis, (Avny, Y.et al., *J. Appl. Polym. Sci.* 1986, 32, 4009), the formation of a surface interpenetrating network of poly(ethylene oxide), (Desai, N. P.et al., *Macromolecules* 1992, 25, 226), chemical reaction at hydroxyl end-groups (Mougenot, P.et al., *J. Macromolecules* 1996, 29, 3552; Mougenot, P.; et al., *J. Coll. Interfac. Anal.* 1996, 177, 162), corona discharge, (Strobel, M. et al., *J. Adhes. Sci. Technol.* 1992, 5, 429), reactive plasma etching, (Wang, J.et al., *J. Appl. Polym. Sci.*, 1993, 50, 585), laser treatment (Bertrand, P.et al., *Nucl. Meth. Phys. Res., Sect. B.* 1987, 19–20, 887) and ion beam modification. (Arenolz, E. et al., *Appl. Surf. Sci.* 1993, 69, 16; Ratner, B. D.et al., in *Plasma Deposition, Treatment, and Etching of polymers* (D'Agostino, Ed.; Academic Press, Inc.: New York, 1990).

In embodiments of the present invention, the functionalized surface of the polymer having a reactive moiety thereon is contacted with a stamp comprising on its surface a ligand comprising a reactive moiety. Reactive moieties of the ligand may be any of the reactive moieties set forth above, as long as they are able to covalently bind to the functionalized polymer surface.

Stamps useful in the present invention are known in the art and may be commercially available. Generally, these stamps are produced by casting a polymeric material onto a mold having the desired pattern. The particular material chosen for formation of the stamp is not critical to the present invention, but should be chosen so as to satisfy certain physical characteristics. In a preferred embodiment, the stamp is elastomeric. Polymeric materials suitable for use in the fabrication of the stamp may have linear or branched backbones, and may be crosslinked or non-crosslinked, depending upon the particular polymer and the degree of formability desired of the stamp. A variety of elastomeric polymeric materials are suitable for such fabrication, especially polymers of the general classes of silicone polymers and epoxy polymers, with silicone elastic polymers being preferred. Examples of silicone elastomers suitable for use as the stamp include those formed from precursors including the chlorosilanes such as methylchlorosilanes, ethylchlorosilanes, and phenylchlorosilanes, and the like. A particularly preferred silicone elastomer is polydimethylsiloxane (PDMS).

The stamp should also be formed such that the stamping surface comprises a material that ligands of the present invention may adsorb to. The invention may be carried out using stamps as described in U.S. Pat. No. 5,817,242 to Biebuyck et al. In a particularly preferred embodiment, the stamp is oxidized, and more preferably is plasma-oxidized, prior to contact with the polymer surface.

The term "ligand," as used herein, means any molecule or compound capable of forming a covalent bond with another reactive molecule or compound. Stated another way, a ligand is a molecule that will covalently bind to a complementary site on another structure or compound. The site of binding may be the reactive moiety of another compound, e.g., a polymer. The ligands of the present invention accordingly comprise at least one reactive moiety (also referred to herein as a "reactive group"). The reactive moiety of the ligand may be at the physical terminus of the ligand, or at any site on the ligand available for forming a covalent bond. Reactive moieties will vary according to the particular ligand being used and the reactive group on the functionalized surface of the polymer to which the ligand will covalently bind. Stated another way, a ligand will comprise a reactive moiety compatible with the ligand and capable of binding to the reactive moiety on the surface of the functionalized polymer surface, such that the reactive moiety of the ligand and the reactive moiety of the polymer surface form a covalent bond. Reactive moieties of the present invention may be any one of the reactive moieties listed above as possible reactive moieties for the functionalized polymer surface, with amine groups being presently preferred. Ligands may naturally comprise reactive moieties, or reactive moieties may be attached or bound to the ligand in some way.

In embodiments of the invention, the reactive moiety is connected to the ligand by means of a spacer molecule. The spacer may be polar; non-polar; halogenated or, in particular, fluorinated; positively charged; negatively charged; or uncharged. For example, a saturated or unsaturated, linear or branched alkyl, aryl, or other hydrocarbon spacer may be used. In some embodiments of the invention, the spacer is polyethylene glycol; in other embodiments, the spacer is an ethylene glycol oligomer.

The ligands of the present invention are generally attached to the stamp by adsorption, which adsorption techniques are known in the art.

Ligands, both biological and non-biological, may be cytophilic, that is, adapted to promote cell adhesion or cell attraction to the ligand. Cells that adhere to these ligands may be whole or fractionated cells. Such ligands may be extracellular matrix proteins, fibronectin, collagen, laminin, serum albumin, polygalactose, sialic acid, and various lectin binding sugars. Ligands may also be "biophilic," that is, may adhere or attract certain biological molecules or compounds.

These ligand include antibodies or fragments of antibodies and their antigens, cell surface receptors and their ligands, nucleic acid sequences and many others that are known to those of ordinary skill in the art.

In practicing the present invention, the stamp being used may be referred to as being "inked" by the ligands. In general, this "inking" means that the stamp comprises on its surface a plurality of ligands, by which is meant either more than one of a particular ligand (i.e., more than one molecule of a ligand), or a variety of different ligands (e.g., molecules of different species, such as a protein and a small biological molecule). In other words, the stamp surface may comprise a heterogenous mixture or a homogenous sample of ligand. The stamp may be inked with a solution comprising the ligands that will be adsorbed to the stamp. This solution may be referred to as "the ink." Accordingly, the inking may, for example, be accomplished by (1) contacting the stamp with a material (e.g., paper, sponge) moistened with the ink, (2) pouring the ink directly onto the stamp, (3) applying the ink to the stamp with a an appropriate application device (e.g., a cotton swab, brush, sprayer, syringe, etc.), or (4) dipping the stamp surface into the solution. The ink may be allowed to dry on the stamp or may be blown dry. The inked stamp is then placed into contact with the functionalized polymer surface for a length of time sufficient for the reactive moieties of the polymer surface and the ligand to bond covalently. The period of time for this will of course vary with the ligands, reactive moieties and polymers being used, but will be able to be determined by one skilled in the art. For example, contacting the stamping surface with the surface polymer for a period of time of approximately 10 minutes is generally adequate to effect sufficient transfer, but contact may be maintained for longer or shorter periods of time if necessary or appropriate.

Once the stamp inked with the ligand is contacted to the polymer surface for a time sufficient to allow the covalent bonding of the reactive moieties of the polymer surface to the reactive moieties of the ligand, the stamp is then separated or removed from the polymer surface, leaving the ligand covalently bound to the functionalized polymer surface. The ligands bound to the polymer surface may, if desired, be treated or modified further by chemical or thermal treatments known in the art. Additionally, if a reactive moiety located on the ligand remains exposed and available to binding by another ligand, such an additional ligand (a "second ligand") may be contacted to the ligand bound to the polymer surface. For example, if the ligand bound to the polymer surface is biotin or biotin-amine, then streptavidin, known to bind to biotin, may be contacted with the bound biotin to form a binding pair. If the ligand is a receptor, a putative receptor agonist or antagonist may be contacted to the polymer surface to determine if the agonist or antagonist compound binds to the receptor. If the ligand is an antibody bound to the polymer surface, the second ligand may be an antigen or hapten.

A polymer surface of the present invention may be stamped more than one time according to methods of the invention. Stamps subsequent to the first stamp may be the first stamp "re-inked," different stamps, stamps with different patterns thereon, and stamps comprising different ligands on the stamp surface.

Although useful in patterning methods (i.e., wherein the stamp contains one or more indentations to produce a pattern of bound ligands on the polymer surface), it is to be understood that the stamp may not have indentations on it. In other words, use of the stamp may create an uninterrupted "lawn" or "block" of ligands covalently bound to the surface of the polymer.

Devices that comprise polymer surfaces microstamped by the methods of the present invention are thus also an aspect of the invention. As will be apparent to those of ordinary skill in the art, the direct binding of biological and other ligands to polymers is important in many areas of biotechnology including, for example, production, storage and delivery of pharmaceutical proteins, purification of proteins by chromatography, design of biosensors and prosthetic devices, and production of supports for attached tissue culture. The present methods find use in creating devices for adhering cells and other biological molecules into specific and predetermined positions. Accordingly, one example of a device of the present invention is a tissue culture plate comprising at least one surface microstamped by the method of the present invention. Such a device could be used in a method for culturing cells on a surface or in a medium and also for performing cytometry. Furthermore, the device could be used in immobilization of cells at a surface and for controlling the shape of a cell. Such devices are useful in a wide array of cellular biology applications, including cell culturing, recombinant protein production, cytometry, toxicology, cell screening, microinjection, immobilization of cells, influencing the state of differentiation of a cell including promoting differentiation, arresting differentiation or causing dedifferentiation. Embodiments of the devices of the present invention can be used to promote ordered cell-cell contact or to bring cells close to one another, but prevent such contact. Other embodiments of the devices of the invention are useful in the creation of artificial tissues for research or in vivo purposes and in connection with creating artificial organs such as artificial liver devices. Still other embodiments of the devices may be useful in connection with generating surfaces for prosthetic or implantable devices.

The following Examples are provided to illustrate the present invention, and should not be construed as limiting thereof.

OVERVIEW OF EXAMPLES

In the following Examples, the present invention is illustrated by patterning biotin onto the polymer PET. The skilled artisan will appreciate that the present method is in no way limited to the use of biotin and PET. PET was chosen for illustrative purposes because it is a widely used biomaterial in synthetic vascular grafts and tissue culture. (Zdrahala, R. J. *J. Biomater. Appl.* 1996, 10, 309. Shakesheff, K.; Cannizzaro, S.; Langer, R. *J. Biomater. Sci., Polym. Ed.* 1998, 9, 507. Cima, L. G. *J. Cell. Biochem.* 1994, 56, 155. Massia, S. P.; Hubbell, J. A. *J. Biomed. Mater. Res.* 1991, 25, 223). Carboxylic acid groups are utilized as the illustrative active group on the polymer surface because they are a convenient functional group for conjugation to a wide variety of biomolecules. (Hermanson, G. T. Bioconjugate Techniques, Academic Press, $1^{st}$ Ed., San Diego, 1996). The choice of biotin as the biological ligand was dictated by the following reasons: (1) biotin is a prototypical small molecule biological ligand; (2) molecular recognition between biotin and streptavidin (or its homologue, avidin) is characterized by tight noncovalent interaction (equilibrium constant=$10^{13}$–$10^{15}$ $M^{-1}$), (Green, N. M. *Biochem. J.* 1966, 101, 774. Chilkoti, A.; Tan, P. H.; Stayton, P. S *Proc. Natl. Acad. Sci., USA* 1995, 92, 1754. Chilkoti, A.; Stayton, P. S. *J. Am. Chem. Soc.* 1995, 117, 10622. Wilchek, M.; Bayer, E.

Avidin-Biotin Technology, Methods in Enzymology, Vol. 184, Academic Press: San Diego, 1990; Vol. 184) and therefore permits facile patterning of streptavidin onto a biotin pattern; and (3) the homotetrameric structure of streptavidin displays 222 point symmetry, (Weber, P. C.; Ohlendorf, D. H.; Wendoloski, J. J.; Salemme. F. R. *Science* 1989, 243, 85. Hendrickson, W. A.; Pahler, A.; Smith, J. L.; Satow, Y.; Merritt, E. A.; Phizackerley. R. P. *Proc. Natl. Acad. Sci. (USA)* 1989, 86, 2190) which positions two pairs of biotin binding sites on opposite faces of the protein, and thereby enables other biotinylated biomolecules (e.g., peptides, DNA, or other proteins) to be specifically immobilized onto the streptavidin pattern in a subsequent incubation step.

PS, PMMA and PET were purchased from GoodFellow Corp.of Berwyn, Pa., and were washed with ethanol prior to use. A comb polymer was synthesized, as described previously by free radical polymerization of MMA, HPOEM ($M_n$~526 g/mol, corresponding to n~10 in FIG. 1) and MePOEM ($M_n$~475 g/mol, m 8.5). See e.g., D. J. Irvine, A. M. Mayes, L. G. Griffith, *Biomacromolecules* 2001, 2, 85. The comb polymer was carboxylated by succinic anhydride, as described elsewhere. The comb polymer was characterized by $^1$H NMR in $CDCl_3$; 4.12 ppm (—$OCH_3$), 3.6–3.65 ppm ($CH_2$—$CH_2$—O—), 0.5–2 ppm ($CH_2$—C—($CH_3$)—) and 3.39 ppm (—OH). The composition of the terpolymer was 61 wt % MMA, 21 wt % HPOEM, and 18 wt % MPOEM using the peaks at 4.12 ppm and 3.39 ppm for quantification. The number average molecular weight (MW) of the comb polymer ($M_n$) was ~25,000 Da with a polydispersity of ~2.7, as measured by gel permeation chromatography using PS calibration standards.

After synthesis, the hydroxyl-functionalized comb polymer was carboxylated by reaction with succinic anhydride in solution. Thin films of the poly(MMA/HPOEM/MPOEM) comb polymer were prepared by spin-coating 1% (w/v) water/methanol (20/80 v/v) solutions of the comb polymer on different surfaces at 2000 rpm and then drying the films at room temperature for 24 h. The spin-cast films were activated by immersion in an aqueous solution of 1-ethyl-3-(dimethylamino)propylcarbodiimide (EDAC, 0.1 M) and N-hydroxysuccinimide (NHS, 0.2 M) for 30 min. The samples were then rinsed with deionized water, dried under a stream of nitrogen, and used immediately thereafter.

The thickness of the comb polymer film, spincast onto a silicon wafer was measured on a home-built single wavelength ellipsometer. See e.g., Z-P. Yang, W. Frey, T. Oliver, A. Chilkoti, Langmuir 2000, 16, 1751. The sessile water contact angles of the comb polymer films on the different polymer surfaces were measured on a Ráme-Hart goniometer (100-00, Mountain Lakes, N.J.) using deionized, distilled water. X-ray photoelectron spectroscopy was performed on an SSX-100 instrument (Surface Science Labs, Mountain View, Calif.) at a take-off angle of 35°, as described elsewhere. See e.g., Z-P. Yang, A. Chilkoti, *Adv. Mater.* 2000, 12, 413 and Z-P. Yang, A. M. Belu, A. Liebmann-Vinson, H. Sugg, A. Chilkoti, *Langmuir* 2000, 16, 7482.

The fabrication of elastomeric stamps with micrometer-size relief features has been described previously, as has the use of MAPS to μCP EZ-Link™ biotin-PEO-LC-amine ((+)-biotinyl-3,6,9-trioxaundecanediamine) (biotin-amine) onto polymers. See e.g., Z-P. Yang, A. M. Belu, A. Liebmann-Vinson, H. Sugg, A. Chilkoti, *Langmuir* 2000, 16, 7482. After micropatterning biotin-amine, the micropatterned surfaces were incubated with 0.1 μM Alexa488-labeled streptavidin or with unlabeled streptavidin in HEPES buffered saline (HBS, pH 7.4) containing 0.02% (v/v) Tween 20 for 1 h. The streptavidin patterns were subsequently incubated with 0.1 μM biotin-LC-Gly-Arg-Gly-Asp-Ser-Pro-Lys (biotin-GRGDSPK) in the same buffer for 1 h or with biotin-GRGDSP(K-TMR).

NIH 3T3 cells were grown in DMEM (Gibco BRL) supplemented with 10% fetal bovine serum (FBS) (Gibco BRL), 100 units/ml penicillin, 100 mg/ml streptomycin, and 7.5 mM HEPES at 37° C. in 5% $CO_2$. Cells were plated on the peptide micropatterned slides or controls at a density of 1×10$^6$ cells/ml in DMEM supplemented with 10% serum. Cells were incubated at 37° C. for either 3 h or 24 h, gently rinsed with culture media to remove loosely adherent cells, and imaged under phase contrast optics.

Example 1

Materials and Methods: Surface Derivatization and Micropatterning

Poly(ethylene terephthalate) films (PET, Melinex® 442/300, Dupont) were cleaned in hexane and acetone and dried under nitrogen. The cleaned PET films were hydroxylated by immersion in 18.5% (v/v) formaldehyde/1 M acetic acid for 4 h. at room temperature. (Massia, S. P.; Hubbell, J. A. *Ann. N.Y. Acad. Sci.-Biomed. Engr.* 1990, 589, 261). Subsequently, the films were reacted with 1 M bromoacetic acid/2 M NaOH overnight, to convert the hydroxyl groups to carboxylic acid on the PET surface (PET-COOH). (Lofas, S.; Johnsson., B. *J. Chem. Soc., Chem. Commun.* 1990, 1526). The PET films were activated by immersion in an ethanol solution of 1-ethyl-3-(dimethylamino)propylcarbodiimide (EDAC, 0.1 M) and pentafluorophenol (PFP, 0.2 M) for 15 min. (Adamczyk, M.; Fishpaugh, J. R.; Mattingly, P. G. *Tetrahedron Lett.* 1995, 36, 8345. Kovacs, J.; Mayers, G. L.; Johnson, R. H.; Cover, R. E.; Ghatak, U. R. *J. Org. Chem.* 1970, 35, 1810).

The masters used to cast the poly(dimethylsiloxane) (PDMS) stamps were fabricated on polished Si wafers using AZ P4620 photoresist (Clariant, Inc.), which was spin coated to a thickness of ~5 microns and processed by contact photolithography. Elastomeric stamps were fabricated by casting PDMS against the photoresist on silicon masters with feature sizes of 10 μm or 40 μm squares, (Wilbur, J. L.; Kumar, A.; Kim, E.; Whitesides, G. M. *Adv. Mater.* 1994, 6, 600) and were subsequently oxidized in an air plasma (150 mtorr, 40 W, 1 min.) in a plasma reactor (Plasmod™, March Instruments Inc., Concord, Cailf.), prior to use.

The ligand (+)-biotinyl-3-6,9,-trioxaundecanediamine (Pierce, hereafter referred to as biotin-amine) was printed by contacting a plasma-oxidized PDMS stamp, inked with 10 mM biotin-amine in ethanol, with the activated PET-COOH surface for 10 min. Flat, plasma oxidized PDMS stamps were used to print biotin-amine for spectroscopic analysis by XPS and TOF-SIMS. Unreacted pentafluorophenyl esters were inactivated by reaction with 2-(2-aminoethoxy)ethanol (AEE, 10 mM, 0.1 M sodium bicarbonate, pH 8.3) for 20 min. The samples were cleaned with ethanol in an ultrasonic bath for 5 min., rinsed with distilled water, and dried, prior to spectroscopic analysis.

After printing biotin-amine on PET-COOH with a PDMS stamp, the surface was incubated with 0.1 µM Alexa™ 488-labeled streptavidin in HEPES buffered saline (HBS, pH 7.4) containing 0.1% (w/v) BSA and 0.02% (v/v) Tween 20 detergent for one hour.

Example 2

Summary of Methods of Analysis of Micropatterning

Because no single analytical technique is capable of elucidating the surface chemistry of micropatterned, derivatized polymers, we have interrogated each step in MAPS by a suite of complementary analytical techniques. The primary analytical technique that we used, time-of-flight secondary ion mass spectrometry (TOF-SIMS) is one of the few, currently available surface analysis techniques that enables spatially-resolved molecular characterization of micropatterned surfaces. This is because TOF-SIMS provides a mass spectrum of the top 10–30 Å with high mass resolution and submicron lateral resolution. (Van Vaeck, L.; Adriaens, A.; Gijbels, R. *Mass Spectrom. Rev.* 1999, 18, 1. Benninghoven, A., *Angew. Chem. Intl. Ed.* 1994, 33, 1023. Pacholski, M. L., Winograd, N. *Chem. Rev.,* 1999, 99, 2977. Briggs, D. In *Polymer Surface Characterization by XPS and SIMS. Characterization of Solid Polymers;* S. J. Spells, Ed. Chapman & Hall: London, 1994; p. 312).

In concert, spectroscopic studies of functionalized polymer surfaces by X-ray photoelectron spectroscopy (XPS) provides the elemental composition (Briggs, D. In *Polymer Surface Characterization by XPS and SIMS. Characterization of Solid Polymers;* S. J. Spells, Ed. Chapman & Hall: London, 1994; p. 312. Swingle II, R. S. *CRC Crit. Rev. Anal Chem.* 1975, 5, 267. Carlson, T. A. *Photoelectron and Auger Spectroscopy;* Plenum Press: New York, 1975. Andrade, J. D. In X-ray Photoelectron Spectroscopy (XPS). Surface and Interfacial Aspects of Biomedical Polymers. 1. Surface Chemistry and Physics J. D. Andrade, Ed.; Plenum Press: New York, 1985; p. 105. Briggs, D. and Seah, M. P. Practical Surface Analysis, John Wiley & Sons: Chichester, 1983) as well as the concentration of functional groups from high resolution core level spectra (Ratner, B. D.; Castner D. G. *Coll.Surf B: Biointerfaces,* 1994, 2, 333. Clark, D. T.; Harrison, A. J. *Poly. Sci., Polym. Chem. Ed.,* 1981, 19, 1945–1955. Clark, D. T.; Thomas H. R. *J. Poly. Sci.: Poly. Chem. Ed.,* 1978, 16, 791–820. Dilks, A. In *X-ray Photoelectron Spectroscopy for the Investigation of polymeric Materials. Electron Spectroscopy—Theory, Techniques and Applications.* Brundle, C. R Baker, A. D. Eds.; Academic Press: London, 1981, p. 277) and by complementary chemical derivatization methods. (Chilkoti, A.; Ratner, B. D. In *Surface Characterization of Advancedpolymers,* Sabbatini, L., Zambonin, P. G., Eds.; VCH: Weinheim, 1993; p. 221). We also used fluorescence microscopy because it enables optical imaging of fluorophore-labeled proteins on micropatterned polymers with good contrast and lateral resolution of a few microns. Accordingly, confocal fluorescence microscopy and TOF-SIMS imaging was used to examine the formation of streptavidin micropatterns on the polymer surface described in Example 1.

Example 3

Materials and Methods: X-ray Photoelectron Spectroscopy

XPS analysis was carried out on an SSX-100 spectrometer (Surface Science Incorporated, Mountain View, Calif.), equipped with a monochromatized $AlK_\alpha$ X-ray source, a hemispherical electron analyzer, and a low energy electron flood gun for charge compensation of insulators. Samples were typically introduced into a preparation chamber, which was maintained at a pressure of $10^{-4}$ torr, and then transferred into the analysis chamber, which was typically maintained at $10^{-8}$ torr. The samples were analyzed at either 15° or 55° take-off angle, defined as the angle between the sample plane and the hemispherical analyzer. The typical X-ray spot size was ~600 µm. Survey scan spectra were acquired from 0–1000 eV for elemental composition, and high-resolution spectra of the $C_{1s}$ core level were acquired from 278–300 eV.

Example 4

Materials and Methods: Time-of-flight Secondary Ion Mass Spectrometry

TOF-SIMS spectra and images were obtained on a TRIFT II TOF-SIMS instrument (Physical Electronics, Eden Prairie Minn.). A mass-filtered $^{69}Ga^+$ liquid-metal primary ion gun was used with a current of ~600 pA. For spectral acquisition, the gun was operated at 15 keV and a pulse width of 12 ns. For imaging, the gun was operated at 25 keV and a pulse width of 30 ns. Details of the spectrometer are described elsewhere. (Schueler, B. *Microsc. Microanal. Microstruct.* 1992, 3, 119–139). The data was acquired over a mass range of m/z 0–1500. The data was collected using an ion dose below the static SIMS limit of $10^{13}$ ions/cm$^2$. A low energy electron beam was used for charge compensation.

Example 5

Materials and Methods: Fluorescence Microscopy

Fluorescence microscopy of Alexa™ 488 labeled streptavidin patterns was performed on a BioRad MRC 1000 confocal microscope (BioRad Microscience Ltd., Hemel Hempstead, U.K.) with a 10× or 20× objective. The confocal microscope was operated at 10% power level and with a detector gain of 1500 V.

Example 6

Results and Discussion: Surface Derivatization of PET

Figure 2:
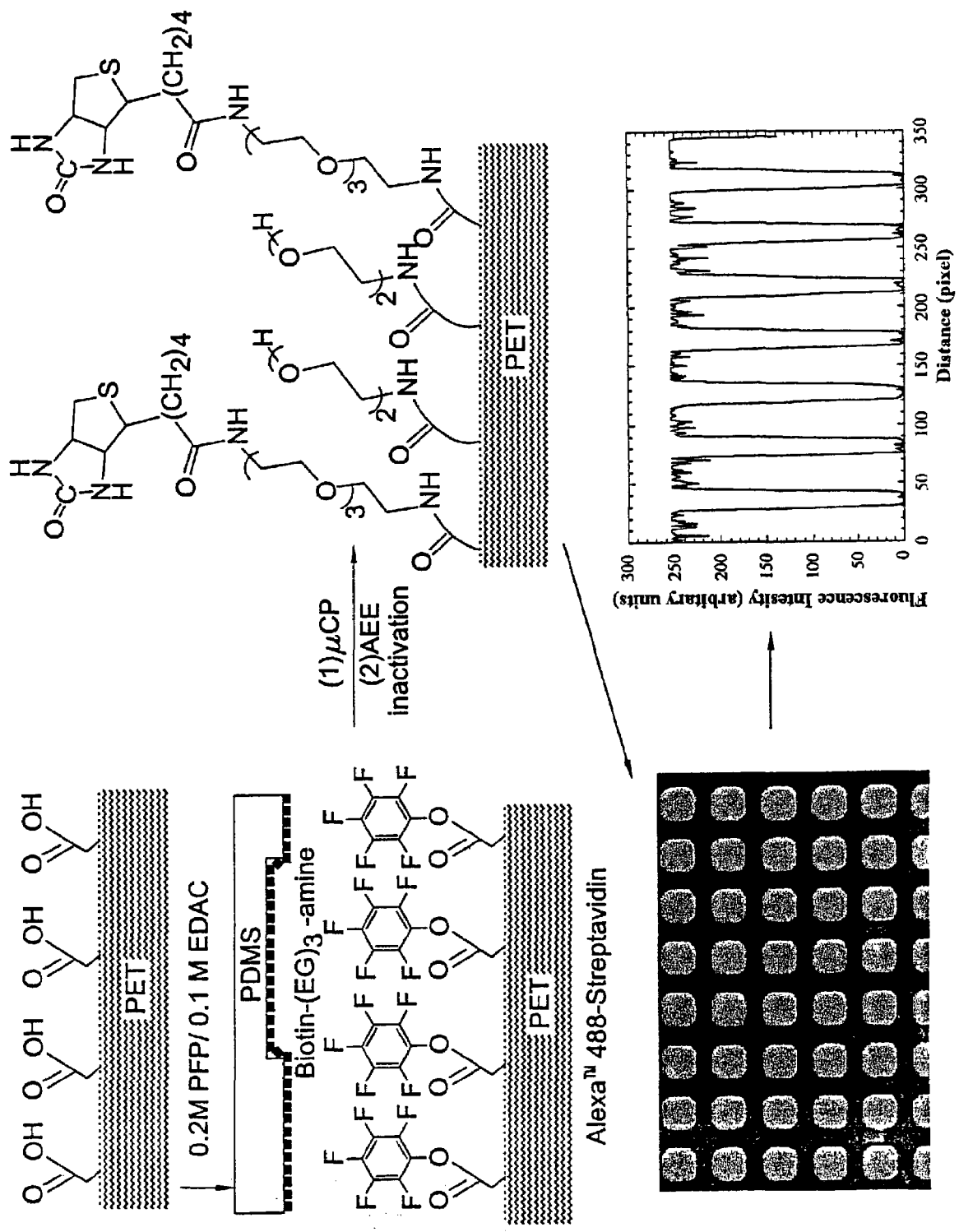
FIG. 2 is a schematic of the method of the present invention used to micropattern biotin-amine onto PET. The lower left panel is a 20× magnification confocal image of Alexa™ 488-labeled streptavidin (0.1 M in HBS, pH 7.4) bound to biotin-amine, which was patterned onto PET-COOH using techniques described herein. A line profile of fluorescence intensity of Alexa™ 488-labeled streptavidin bound to biotin-amine patterns created by MAPS on PET-COOH is shown on its right.

PET was derivatized in two steps to introduce carboxylic acid groups at the surface, as shown in FIG. 1. The first step, the hydroxymethylation of the aromatic ring in PET introduced a benzylic hydroxyl group within the PET repeat unit, (Massia, S. P.; Hubbell, J. A. *Ann. N.Y. Acad. Sci.-Biomed. Engr.* 1990, 589, 261) which was then converted to a carboxyl group by reaction with bromoacetic acid. (Lofas, S.; Johnsson., B. *J. Chem. Soc., Chem. Commun.* 1990, 1526). After the introduction of carboxylic acid groups on the surface of PET (the carboxyl derivatized PET surface is termed PET-COOH), the carboxylic acid groups were then activated by reaction with pentafluorophenyl (PFP) (FIG. 2). We chose PFP to activate the carboxylic acid groups in PET-COOH, because previous reports suggest that pentafluorephenyl esters are significantly more reactive than the more commonly used N-hydroxysuccinimide ester. (Adamczyk, M.; Fishpaugh, J. R.; Mattingly, P. G. *Tetrahedron Lett.* 1995, 36, 8345. Kovacs, J.; Mayers, G. L.; Johnson, R. H.; Cover, R. E.; Ghatak, U. R. *J. Org. Chem.* 1970, 35, 1810) The activated PET surface was then patterned with biotin-amine by spatially-resolved reagent transfer using a PDMS stamp inked with the ligand (FIG. 2). Unreacted esters were quenched by reaction with AEE.

Example 7

Results and Discussion: XPS Characterization

The carboxylation of PET was confirmed by XPS in combination with chemical derivatization with PFP. (Chilkoti, A.; Ratner, B. D. In *Surface Characterization of Advanced polymers,* Sabbatini, L., Zambonin, P. G., Eds.; VCH: Weinheim, 1993; p. 221). No fluorine was observed in unmodified PET after exposure to PFP/EDAC (Table 1). In contrast, 3–4 (atomic) %F was measured for PET-COOH derivatized with PFP. These results suggest that PET was successfully functionalized with COOH groups. The functionalization of PET with COOH groups proceeded homogeneously within the top 50 Å of the surface because XPS analyses at two different take off angles, 15° and 55° gave experimentally indistinguishable results. Furthermore, the measured F/C ratio for PFP-derivatized PET-COOH indicates that the carboxylic acid concentration in PET-COOH is ~21% of the theoretical maximum, which was calculated with the following assumptions: (1) 100% carboxylation of PET within the XPS sampling depth via the reaction scheme shown in FIG. 1, and (2) 100% derivatization of the carboxyl groups in PET-COOH by PFP/EDAC. With the above assumptions, the XPS results indicate that ~1 COOH group was introduced every 5 repeat units of PET.

ratio of 0.023 for PET-COOH derivatized with biotin-amine using a flat PDMS stamp compares favorably with the N/C ratio of 0.027, obtained for derivatization of PET-COOH with biotin-amine from solution. In contrast, no nitrogen was detected on the surface of unmodified PET. These atomic ratios are ~19% of the theoretical maximum of 0.12. Upon correcting for the experimentally determined concentration of available COOH groups, these results also suggest that reaction of the available COOH groups present in PET-COOH with biotin-amine, after activation with PFP/EDAC, proceeded to completion.

The XPS $C_{1s}$ spectra of biotin-derivatized PET-COOH and native PET also corroborate these results. The $C_{1s}$ spectra of PET, acquired at various stages of the multistep functionalization procedure, were fit with the following criteria: (1) all spectra were corrected for sample charging using the $CH_x$ component in the resolved spectra at 284.6 eV as reference. Additional peaks for the oxygen-containing functionalities (Clark, D. T.; Harrison, A. J. *Poly. Sci., Polym. Chem. Ed.,* 1981,19, 1945–1955. Clark, D. T.; Thomas H. R. *J. Poly. Sci.: Poly. Chem. Ed.,* 1978, 16, 791–820. Dilks, A. In *X-ray Photoelectron Spectroscopy for the Investigation of Polymeric Materials. Electron Spectroscopy—Theory, Techniques and Applications.* Brundle, C. R Baker, A. D. Eds.; Academic Press: London, 1981, p. 277) were incorporated in the peak fit: these include C—O—H/R (286.2 eV), COOR (288.6 eV) and a π→π* shakeup satellite at 291.6 ev.(Gardella, J. A.; Ferguson, S. A.; Chin, R. L. *Appl. Spectrosc.* 1986, 40, 224). Full widths at half maximum of the component peaks in the spectral envelope were constrained to 1.2–1.4 eV during curve fitting, which is consistent with the energy resolution of the SSX-100 spectrometer.

The $C_{1s}$ spectra of PET PET-OH, and PET COOH (Table II) were qualitatively very similar, which is due to the low level of functionalization of PET, and the high concentration of COOR groups that are present in native PET, which mask the incorporation of carboxyl groups in PET-COOH. The spectrum of native PET (and PET-OH and PET-COOH) were fit with four peaks, which were assigned to $CH_x$,

TABLE I

Measured and calculated atomic ratios of PFP-derivatized PET-COOH and biotin-derivatized PET-COOH.

| | | Measured | | | [1]Calculated | | |
|---|---|---|---|---|---|---|---|
| Sample | Derivatization | N/C | O/C | F/C | N/C | O/C | F/C |
| PET | — | 0 | 0.31 | 0 | 0 | 0.40 | 0 |
| PET | 0.1 M PFP/0.2 M EDAC | 0 | 0.32 | 0 | 0 | 0.40 | 0 |
| PET-COOH | 0.1 M PFP/0.2 M EDAC | 0 | 0.33 | 0.06 | 0 | 0.37 | 0.26 |
| PET-biotin (solution) | Biotin-amine | 0.023 | 0.33 | 0 | 0.13 | 0.36 | 0 |
| PET-biotin (flat stamp) | Biotin-amine | 0.027 | 0.34 | 0 | 0.13 | 0.36 | 0 |

[1]The calculated atomic ratios assume the following:
(1) the hydroxylation of PET proceeds specifically by hydroxymethylation of the aromatic ring in PET as shown in the reaction scheme in FIG. 1 with 100% yield;
(2) all subsequent derivatization reactions also proceed with 100% yield throughout the entire sampling depth of XPS.

XPS of PET-COOH, derivatized with biotin-amine using a flat, plasma-oxidized PDMS stamp inked with ligand, provided direct evidence for the reaction of COOH groups on the surface of PET-COOH with biotin-amine. The N/C C—O—R, COOR and a π→π* shakeup satellite. The peak area ratio of 3.3:1:0.9 for the $CH_x$:C—O—R:COOR species, determined by curve fitting of the $C_{1s}$ spectrum of PET is close to the stoichiometric 3:1:1 ratio of PET.

TABLE II

Resolved XPS high resolution $C_{1s}$ spectra. Details of the peak fit are in the text.

| Sample | % $CH_x$ (284.6 eV) | % C—N/C—S (285.4 eV) | % C—O—R (286.2 eV) | % COOR (288.6 eV) | %π -> π* (291.6 eV) |
|---|---|---|---|---|---|
| PET | 62.7 | — | 18.7 | 16.7 | 1.9 |
| PET-OH | 61.7 | | 18.8 | 16.5 | 2.0 |
| PET-COOH | 62 | | 18.9 | 16.5 | 2.5 |
| PET-biotin (flat stamp) | 48.6 | 12.6 | 18.6 | 16.4 | 1.9 |

The reaction of biotin-amine with PET-COOH clearly alters the $C_{1s}$ (Table II). Curve fitting of the spectrum of biotin-derivatized PET-COOH by the above criteria required the inclusion of a new peak, centered at 285.4 eV. This peak was assigned to the C—N and C—S species in biotin. (Beamson, G.; Briggs, D. *High resolution XPS of organic polymers,* John Wiley: Chichester, 1992). Assuming homogeneous functionalization within the XPS sampling depth, the (C—S+C—N):$CH_x$ ratio of 0.23 for PET-COOH derivatized with amine-terminated using a flat stamp inked with the ligand suggests that ~1 biotin molecule is introduced into every 5 repeat units in PET, which corroborate the results obtained from XPS elemental analysis.

Example 8

Results and Discussion: Fluorescence Microscopy

The spatial distribution of streptavidin on the micropatterned biotin on PET-COOH was examined by incubating the patterned surface with Alexa-488 labeled streptavidin. A 20× magnification confocal image of Alexa™ 488-labeled streptavidin (FIG. 2, lower left panel) shows that streptavidin is spatially-localized on the periodic, 40 μm×40 μm biotin micropattern printed by MAPS on PET-COOH. The average contrast ratio of the protein pattern in this image is 250:1 (FIG. 2, line intensity profile), and clearly demonstrates the successful localization of streptavidin on the biotin pattern, mediated by molecular recognition between the protein and immobilized ligand, as well as suppression of streptavidin adsorption on the unstamped regions, due to the presence of BSA and Tween 20™.

In contrast, the fluorescence intensity of unmodified PET, which was similarly stamped with a plasma-oxidized PDMS stamp inked with biotin-amine, followed by incubation with Alexa™ 488-labeled streptavidin showed an average contrast ratio between the patterned region and background of ~40:1 (results not shown). These results suggest that the covalent incorporation of biotin into PET-COOH provides a six fold higher concentration of immobilized streptavidin at the surface as compared to adsorption of biotin. There are at least two possible reasons for the low, albeit significant streptavidin adsorption on the control, unmodified PET stamped with biotin-amine: (1) streptavidin bound to adsorbed biotin, which was incompletely desorbed during the rinsing procedure that preceded incubation with Alexa™ 488-labeled streptavidin; (2) the different surface chemistry between stamped and unstamped regions, due to the presence of residual biotin and PDMS transferred from the stamp, resulted in greater adsorption of streptavidin to the regions that were in contact with the PDMS stamp as compared to the background.

Figure 3A:
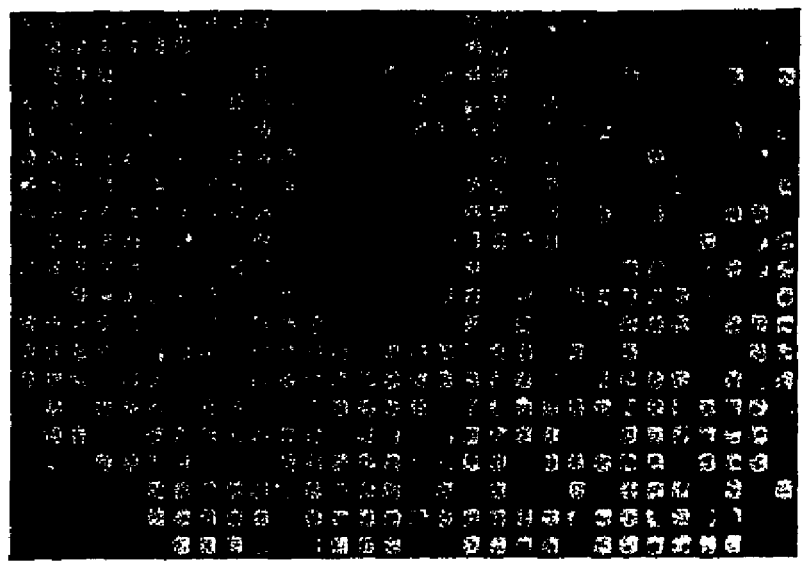
FIGS. 3A and 3B are fluorescence images of Alexa™ 488-strepatvidin bound to biotin micropatterns fabricated on PET using, as shown in FIG. 3A, an unoxidized PDMS stamp or, as shown in FIG. 3B, a PDMS stamp oxidized by a 1 min. air plasma treatment.
Figure 3B:
Figure 4B:
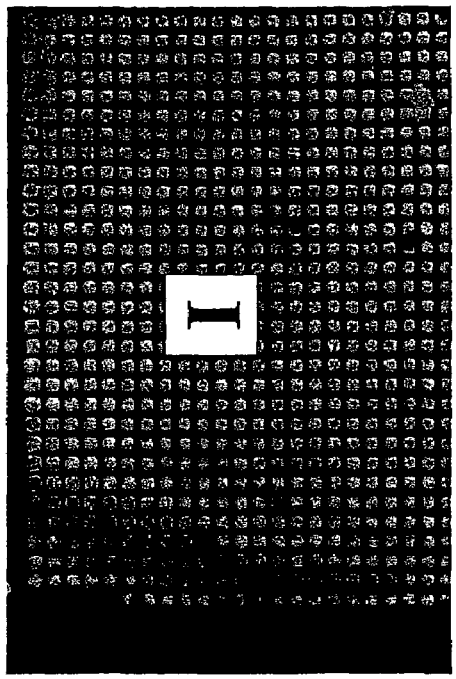
FIGS. 4A, 4B, 4C and 4D illustrate 10× magnification confocal images of Alexa™ 488 labeled streptavidin patterns from a 9 mm×9 mm area, patterned with biotin-amine on PET-COOH by MAPS. A PDMS stamp with 10 μm square feature and an interfeature spacing of 5 μm was used to generate these patterns.
Figure 4D:
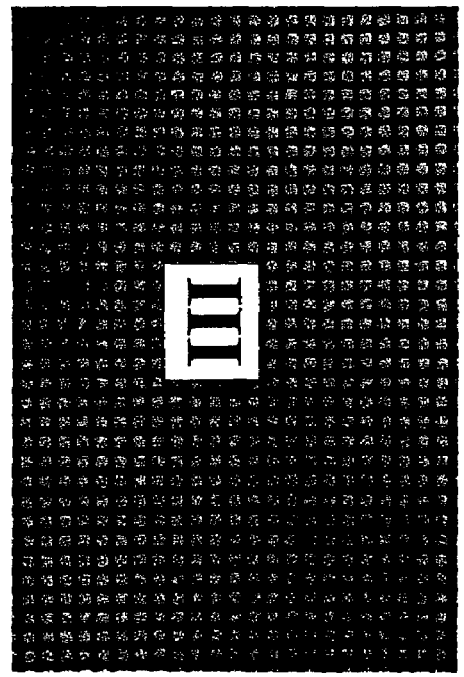
Figure 4A:
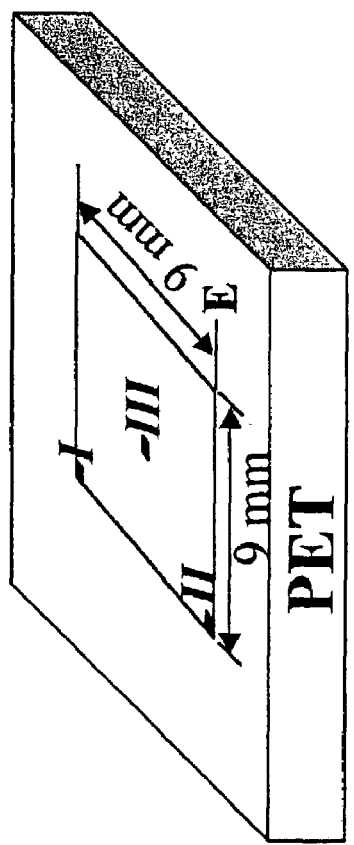
Figure 4C:
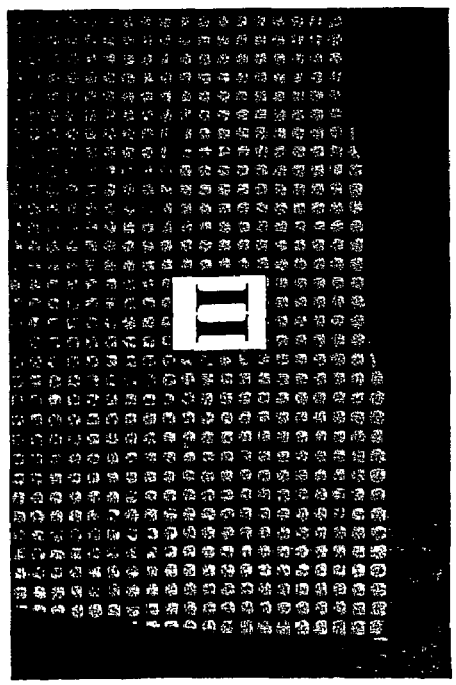

The quality of the biotin micropattern printed by MAPS was strongly affected by the surface energy of the PDMS stamp. Untreated PDMS stamps produced poor quality patterns, as shown by fluorescence microscopy of the binding of Alexa-labeled streptavidin (FIG. 3A). In contrast, a 1 min. air plasma treatment substantially improved the transfer of ligand to the surface (FIG. 3B), presumably because the increased hydrophilicity of the plasma-oxidized PDMS surface enabled complete wetting of the surface of the PDMS stamp by the ligand solution. This result is consistent with that of Lahiri et al.(supra) for reactive μCP of biotin on SAMs on gold.

We also examined the reproducibility of the biotin micropattern, by stamping a large (9 mm×9 mm) area of PET-COOH with biotin-amine using a stamp with 10 μm square features and an interfeature spacing of 5 μm. The patterns were incubated with Alexa 488-labeled streptavidin and visualized by fluorescence microscopy. FIG. 4, a composite 10× image, obtained from different regions of the surface, shows the uniformity of the pattern over the entire, stamped region. The loss of feature resolution and intensity, observed at the edge of the stamped regions, is probably caused by edge effects due to inhomogeneous distribution of the applied stress on the PDMS stamp and slight curvature of the surface. The stability of the streptavidin pattern was also examined; after fluorescence imaging, the sample was stored in HBS (pH 7.4) containing Alexa™ 488-labeled streptavidin (0.1 μM) for a week, and then examined again by fluorescence microscopy. No differences were observed either in the total intensity of the patterned regions with time or in the contrast between patterned regions and background (results not shown).

Example 9

Results and Discussion: TOF-SIMS Spectroscopy

Figure 5:
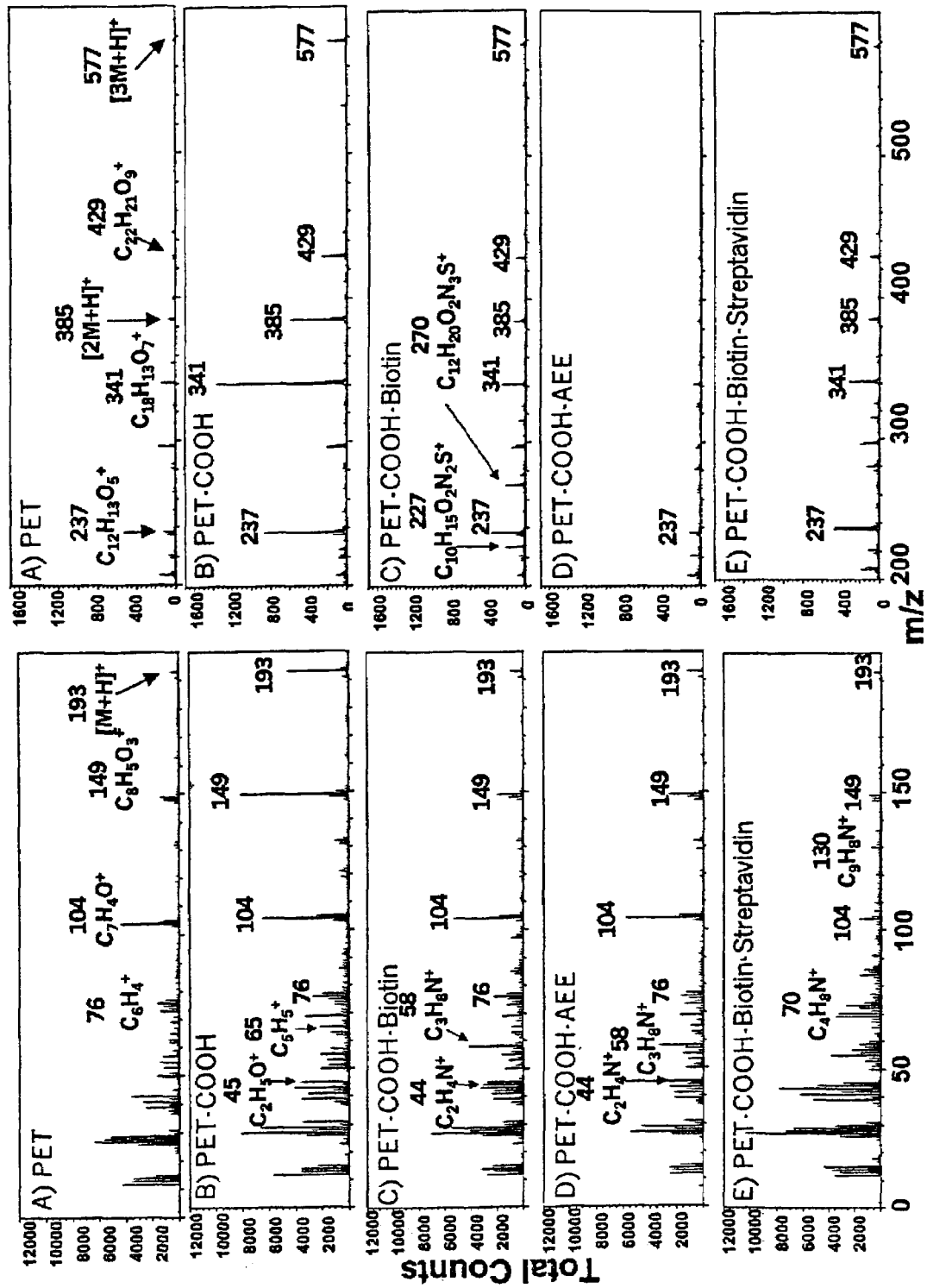
FIGS. 5A, 5B, 5C, 5D and FIG. 5E are (+) Time-of-Flight Secondary Ion Mass Spectrometry (TOF-SIMS) spectra of: PET (FIG. 5A); PET-COOH (FIG. 5B); PET-COOH derivatized with biotin-amine (FIG. 5C), PET-COOH derivatized with AEE (FIG. 5D), and PET-COOH derivatized with biotin-amine and incubated with streptavidin (FIG. 5E). Each modification step was confirmed by the presence of molecular ions unique for each molecule. P represents characteristic PET ions (M=repeat unit of PET). B represents characteristic biotin ions. A represents characteristic AEE ions. S represents characteristic streptavidin ions.

In order to monitor each step of the functionalization of PET by MAPS, it was necessary to first identify secondary ions that are unique to each step of the derivatization procedure. Samples were prepared for each derivatization step and analyzed by TOF-SIMS. The positive ion spectrum of native PET shows characteristic peaks for PET at m/z 76, 104, 149, 193 $[M+H]^+$ (M=repeat unit of PET), 237, 341, 385 $[2M+H]^+$, 429, 577 $[3M+H]^+$ and 769 $[4M+H]^+$ (FIG. 5A). (The Static SIMS Library, Version 2, SurfaceSpectra Limited, Manchester, UK, 1999). The positive ion spectrum of PET-COOH is qualitatively similar to that of PET (FIG. 5B); the series of molecular secondary cations, characteristic of PET are also observed in the TOF-SIMS spectrum of this sample. The peaks at m/z 45 ($C_2H_5O^+$) and m/z 65 ($C_5H_5^+$), however, display increased intensity relative to unmodified PET. Furthermore, the intensity of molecular ions derived from PET increased by between five- and ten-fold for PET-COOH compared to native PET. This increase in intensity was observed both in positive (FIG. 5B) and negative ion mode (results not shown), suggesting an increased concentration of PET oligomers on the surface of the modified polymers.(Briggs, D. *Surf. Interface Anal.* 1986, 8, 133–136). We believe that the low MW PET oligomers are created by hydrolytic chain cleavage of PET, which also creates hydroxyl and carboxylic acid functionalities at the new chain ends. Therefore, the scheme shown in FIG. 1 is only approximate, and it is likely that a substantial fraction of reactive groups arise from side reactions such as hydrolytic cleavage of the PET backbone.

PET-COOH surfaces were reacted with biotin-amine by conformal contact of a flat PDMS stamp, inked with the reagent, with the surface or by reaction from solution. TOF-SIMS provided evidence for the reaction of biotin with the COOH groups. FIG. 5C shows the TOF-SIMS positive ion spectrum PET-COOH reacted with biotin-amine from solution, where new peaks at m/z 44 ($C_2H_4N^+$) and 58 ($C_3H_8N^+$) are observed. Molecular ions of low intensity at m/z 227 ($C_{10}H_{15}O_2N_2S^+$) and 270 ($C_{12}H_{20}O_2N_3S^+$) are also observed. (The Static SIMS Library, Version 2, SurfaceSpectra Limited, Manchester, UK, 1999. Briggs, D. *Surf. Interface Anal.* 1986, 8, 133–136). These results strongly suggest the covalent reaction of biotin-amine with PET-COOH, because these peaks were not observed on native PET or PET-COOH, and biotin-amine was the only nitrogen containing species in this multi-step derivatization procedure. Further, the new peaks observed at m/z 26 ($CN^-$) and 42 ($CNO^-$) in the negative ion spectrum also indicate the introduction of a nitrogen-containing moiety (FIG. 6).

After derivatizing PET-COOH with biotin-amine using a patterned stamp in MAPS, the unpatterned regions were quenched with AEE. Therefore, it was necessary to analyze a control sample of AEE-modified PET-COOH to identify characteristic TOF-SIMS peaks for AEE. The positive ion spectrum is dominated by peaks that are characteristic of PET (FIG. 5D). Compared to the spectra of PET-COOH, the peaks at m/z 44 ($C_2H_4N^+$), 58 ($C_3H_8N^+$), 26 ($CN^-$) and 42 ($CNO^-$) (negative ions results are not shown) display significantly greater intensity. Unique peaks for AEE were not observed, compared to biotin-derivatized PET-COOH. The important distinction between the spectrum of PET-COOH derivatized with AEE compared to biotin-amine is the presence of the molecular biotin species (m/z $227^+$ and $270^+$) in the positive ion spectrum (FIG. 5C) and the greater intensity of m/z $26^-$ and $42^-$ in the negative ion spectrum of biotin-derivatized PET-COOH (FIG. 6).

Figure 6:
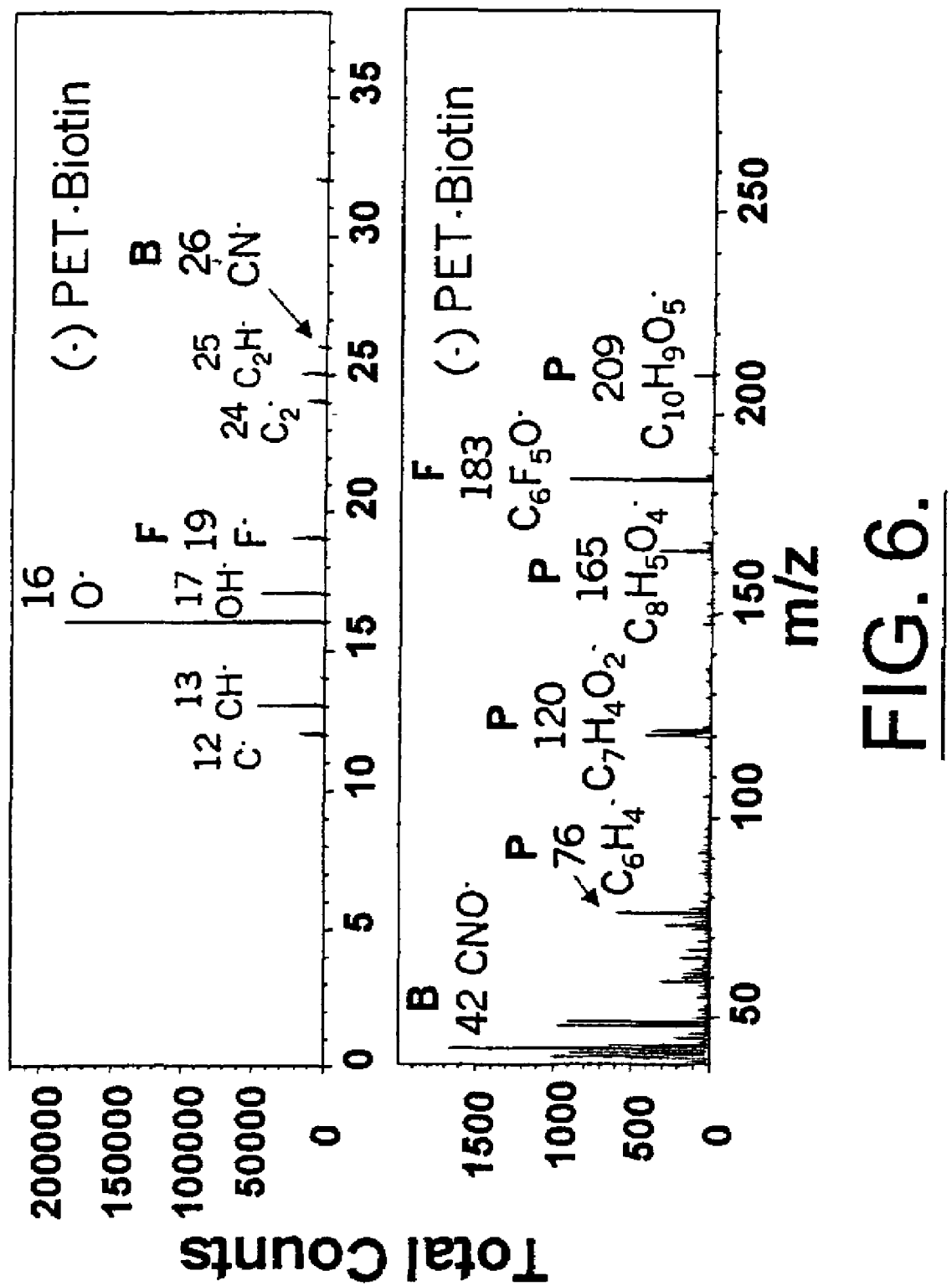
FIG. 6 is a (−) TOF-SIMS spectrum of PET-COOH reacted with biotin-amine. P represents characteristic PET ions. B represents characteristic biotin ions. F represents characteristic PFP ions. The presence of PFP species indicates the activating agent is not fully quenched in the derivatization reaction.

The negative ion TOF-SIMS spectrum of PET-COOH reacted with biotin-amine also shows evidence of PFP, which was used to convert carboxylic acid groups to reactive pentafluorophenyl esters (FIG. 6). The spectrum contains significant peaks at m/z 19 ($F^-$) and 183 ($C_6F_5O^-$), which is the intact parent ion of PFP. The presence of these ions suggest that the reaction of the pentafluorophenyl ester with AEE and subsequent hydrolysis of unreacted pentafluorophenyl ester in the unpatterned, background region only proceeded partially to completion.

In the final step of MAPS, the biotin-derivatized PET was incubated with Alexa488-labeled streptavidin to enable protein micropatterning via molecular recognition between biotin and streptavidin. The TOF-SIMS spectrum of this sample exhibited unique peaks for streptavidin at m/z=70 ($C_4H_8N^+$) and 130 ($C_9H_8N^+$) in the positive ion mode (FIG. 5E), and at m/z=46 ($NO_2^-$) and 62 ($NO_3^-$) in the negative ion mode (results not shown). Attribution of these ions to streptavidin was confirmed by TOF-SIMS of an adsorbed monolayer of Alexa 488 labeled streptavidin on PET (results not shown).

Example 10

Results and Discussion: TOF-SIMS Imaging

The imaging mode of TOF-SIMS was used to analyze the patterned samples and monitor the distribution of characteristic molecular species. Patterned biotin samples were rinsed in an ultrasonic bath of ethanol, prior to analysis, to reduce PDMS contamination to background level.

Figure 7A:
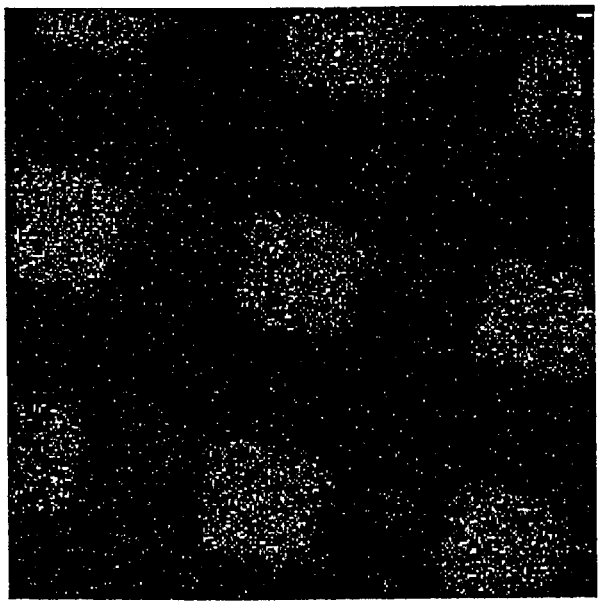
FIGS. 7A, 7B, 7C and 7D are TOF-SIMS images of a sample of biotin patterned onto activated PET using a 40 μm stamp. The map of the CN⁻ ion (26 Da) in FIG. 7A confirms the presence of biotin created by the stamp.

TOF-SIMS imaging of cleaned samples enabled spatial mapping of biotin-amine, patterned onto activated PET-COOH, using a PDMS stamp with 40 μm square features. The square regions of biotin were best observed by mapping the distribution of $CN^-$ in the negative ion mode. The image clearly indicates the biotin ligand is spatially localized in the 40 μm square contact regions (FIG. 7A). The $CN^-$ map displays significant intensity in the background, which arises from AEE, the reagent used to pentafluorophenyl ester groups not functionalized with biotin-amine. The visible contrast in the image is a consequence of the higher intensity of this peak from the biotinylated regions as compared to the background regions functionalized with AEE, and demonstrates that even the difference in peak intensity of an ion created from two different parent molecules on the surface is sufficient to spatially map the surface chemistry.

Figure 7C:
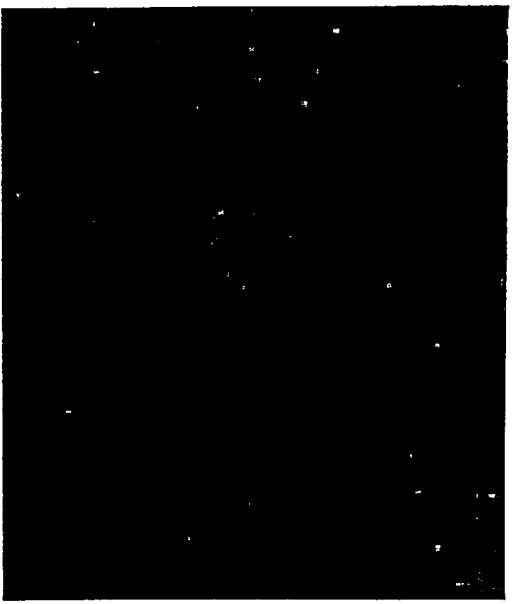

Although its intensity is very low, the peak at m/z $227^+$, the parent molecular peak of biotin, can also be used to unequivocally map the distribution of biotin. Because the surface is destroyed over time by collision of the primary ion beam with the surface in TOF-SIMS, it is likely that the biotin molecule most likely fragmented before significant signal-to-noise could be obtained in the imaging mode of TOF-SIMS. The image of m/z $227^+$, nevertheless, even with poor signal to noise, demonstrates that biotin is localized in the 40 μm square regions (FIG. 7C).

Figure 7B:
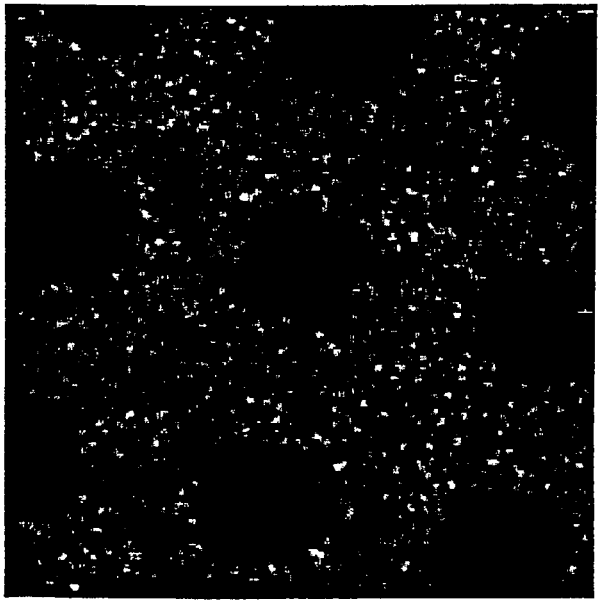

PFP was used to activate the entire PET-COOH surface before stamping with biotin-amine. FIG. 7B shows the image of the parent molecular anion of PFP (m/z $183^-$) after patterning PFP derivatized PET-COOH with biotin-amine and quenching with AEE. The peak at m/z 183 is localized solely to the regions where biotin is absent, which suggests that reaction of PFP with biotin and AEE, and subsequent hydrolysis in buffer proceeds to completion in the patterned regions but is incomplete in the background.

Figure 7D:
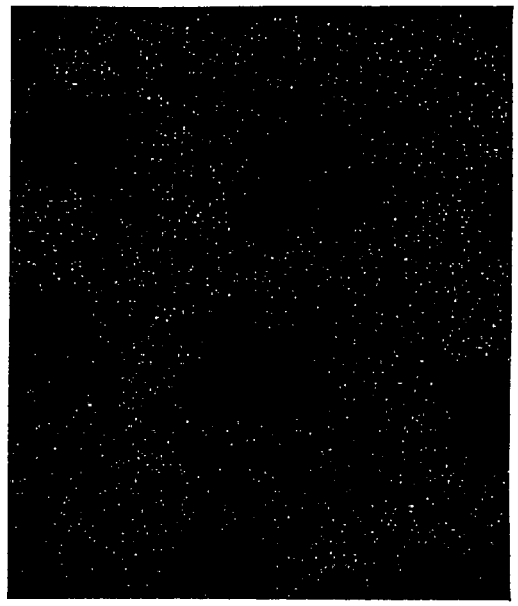

FIG. 7D shows the spatial distribution of m/z 104 ($C_7H_4O^+$), which is unique to PET, and shows that the intensity of this ion is highest in the regions that do not contain biotin. Because PET is the surface, it is believed that the observed contrast is a consequence of the shallow sampling depth of TOF-SIMS for molecular ions, so that biotin molecules in the patterned regions mask PET. In contrast, the PET signal is stronger from the background, because PFP and AEE are smaller molecules than biotin and may have a lower surface coverage.

Figure 8B:
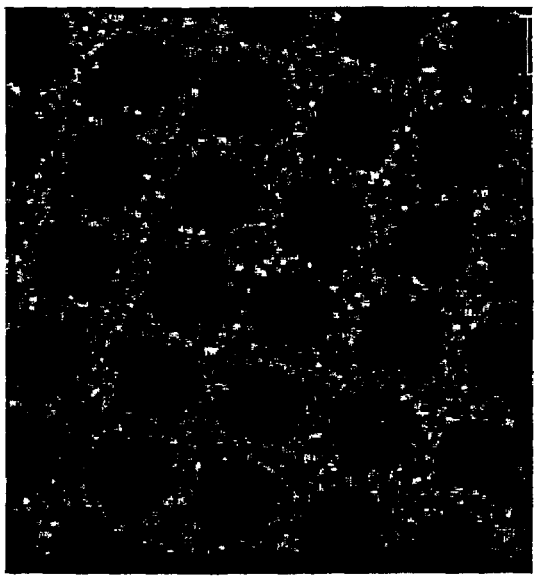
FIGS. 8A, 8B, and 8C are TOF-SIMS images of a streptavidin pattern. The PET-COOH surface was first patterned with biotin-amine using a 10 μm stamp and subsequently incubated with streptavidin in the presence of Tween20™.
Figure 8A:

The patterned biotin samples were also analyzed by imaging TOF-SIMS after incubation with streptavidin (FIG. 8). The image of m/z 70, which is unique to streptavidin, shows the spatial localization of streptavidin and reveals that the streptavidin binds selectively to the 10 μm square patterned biotin regions (FIG. 8B). In contrast, the image of m/z 104 for PET, shows higher intensity for regions of PET surface that were not in contact with the PDMS stamp (FIG. 8A). The two images show a contrast inversion and dem onstrate the successful patterning of PET with streptavidin.

Figure 8C:
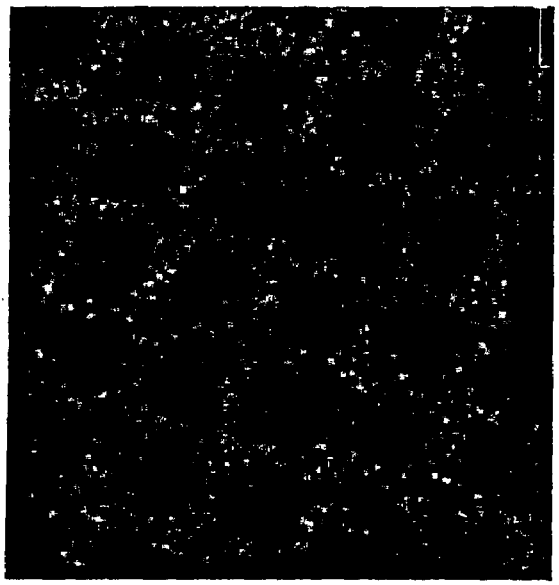
Figure 9B:
FIGS. 9A, 9B, 9C and 9D illustrate the effect of Tween 20™ blocking agent (BA) on binding of streptavidin to a biotin micropattern. TOF-SIMS images of micropatterned biotin on PET-COOH incubated with streptavidin were acquired with (FIGS. 9A and 9B) and without Tween 20™ (FIGS. 9C and 9D) in the protein solution.
Figure 9D:
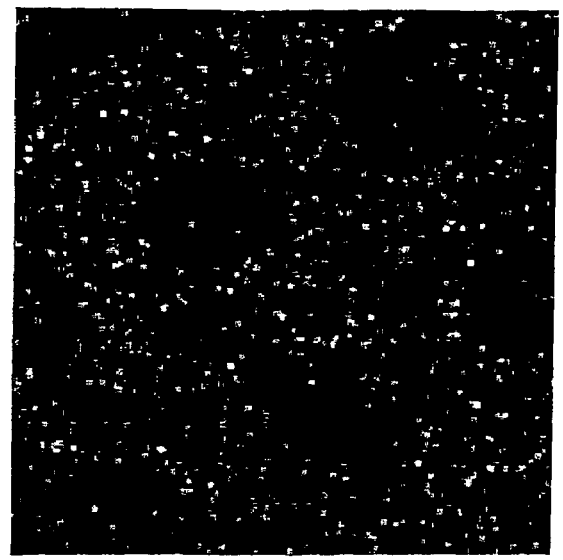
Figure 9A:
Figure 9C:
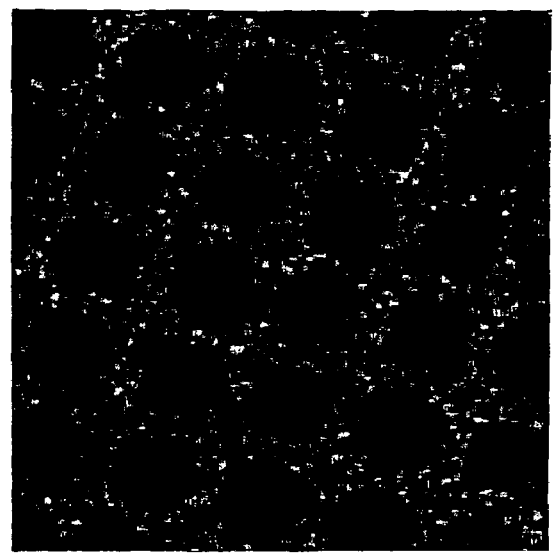

Streptavidin was incubated in the presence of Tween 20™, a blocking agent composed of polyoxyethylene sorbitan monostearate. TOF-SIMS clearly shows the presence of Tween 20™ by the characteristic peaks at m/z 227, 255 and 283 in the positive ion mode (FIG. 8C). These peaks represent the series of myristic, palmitic and stearic fatty acids, and are sidechains of the sorbitan molecule. (Beamson, G.; Briggs, D. *High resolution XPS of organic polymers*, John Wiley: Chichester, 1992). The TOF-SIMS image of this series of peaks shows that Tween 20™ is preferentially located in the background region. This localization of Tween 20™ also explains the high, 250:1 contrast observed for streptavidin in fluorescence microscopy. The high contrast of the fluorescence images can be attributed both to the selective binding of streptavidin to patterned biotin, as well as the preferential adsorption of the surfactant, Tween 20, to the background. In comparison, TOF-SIMS images of biotin-derivatized PET-COOH incubated with streptavidin without the addition of the Tween 20™, showed poor spatial resolution of protein-containing peaks. This is clearly seen upon comparing the m/z 26 map ($CN^-$) for a streptavidin pattern incubated with (FIG. 9B) and without Tween 20 (FIG. 9D). Similarly, the contrast inversion of representative secondary ions from the PET surface (m/z $104^+$) (FIG. 9A), which is a consequence of the preferential binding of streptavidin to the biotin micropattern and the ~1–2 nm sampling depth of TOF-SIMS, is also substantially reduced when the blocking agent is not included (FIG. 9C). These results clearly confirm that Tween 20 significantly reduces nonspecific adsorption of streptavidin to the background, unstamped regions.

Overall, the present MAPS invention finds advantage in that is applicable to a wide variety of polymers that are amenable to surface modification, and thus is useful for micron scale patterning of small molecule ligands, peptides, and protein onto polymer surfaces for biomaterial and biotechnological application. Micropatterning of reactive ligands on derivatized polymer surfaces with a spatial resolution of at least 5 μM, high contrast and good reproducibility. MAPS will find particular use in the spatially-resolved immobilization of biomolecules that are difficult to stably adsorb onto polymers, such as small biological ligands.

Example 11

Comb Polymer Synthesis

Figure 12:
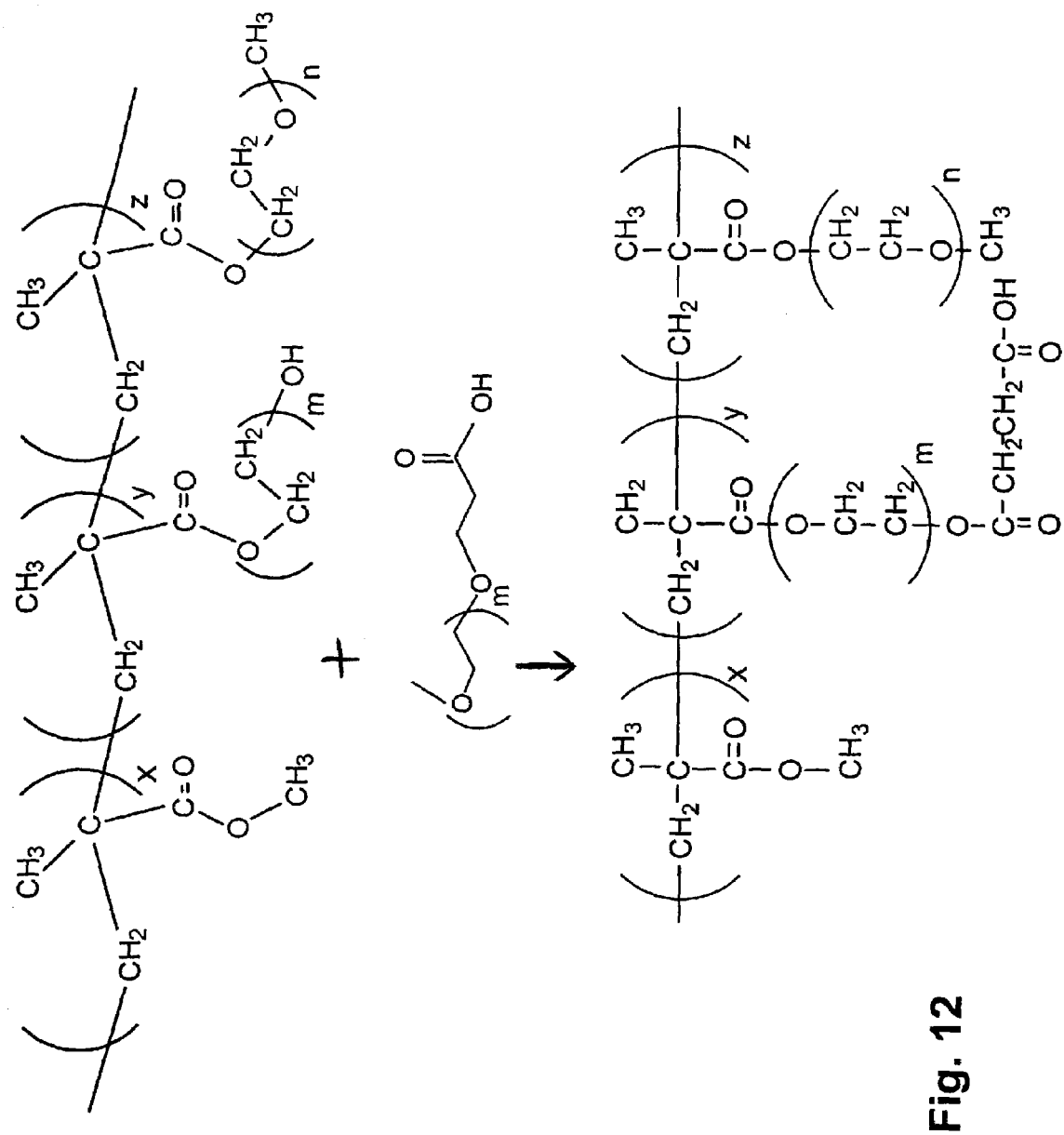
FIG. 12 illustrates the chemical structure of an amphiphilic poly(MMA/HPOEM/POEM) comb polymer.

An amphiphilic comb polymer was formed on a substrate surface according to the following procedure. In particular, a random poly(MMA/HPOEM/MePOEM) terpolymer is formed by free radical copolymerization of the three monomers. FIG. 12 illustrates the chemical structure of an amphiphilic poly(MMA/HPOEM/POEM) comb polymer. NMR showed that the comb polymer contained 61 weight percent MMA, 21 weight percent HPOEM and 18 weight percent MPEOM, corresponding to a molar ratio of 16:1:1. See e.g., D. J. Irvine, A. M. Mayes, L. G. Griffith, *Biomacromolecules* 2001, 2, 85. After derivatization of the terminal OH groups in HPOEM with succinic anhydride, a small fraction (i.e., less than 5%) of the terminal OH groups were converted to COOH groups as observed by the appearance of a new resonance at around 10 ppm. See e.g., R. F. Storey, T. P. Hickey, J. Polym. Sci., Part A: Polym. Chem. 1993, 31, 1825.

Example 12

Functionalized Surface Formation

The COOH-derivatized comb polymer was spincast onto a PS, tissue culture PS (TCPS), PMMA, and PET. Such polymers were selected as the candidate surface in this example, because they are often used as biomaterials and in tissue culture. See e.g., B. D. Ratner, in Biomaterials science: an introduction to materials in medicine; Academic Press, San Diego, Calif., 1996. It should be appreciated that surfaces formed from other materials can be employed in accordance with the teachings of the present invention.

Prior to micropatterning with MAPS, the spincast films were characterized by ellipsometry, atomic force microscopy (AFM), water contact angle measurements and X-ray photoelectron spectroscopy (XPS). The thickness of a spincast film from a 1 percent (w/v) solution of the polymer onto a silicon wafer was determined to be approximately 50 mn, and this thickness did not appreciably change upon prolonged exposure of the surface to water for about one month. The surfaces were uniformly covered with comb polymer, as observed by contact mode AFM. The root mean square roughness obtained by AFM was less than about 5 nm. The change in water contact angle after modification of PS and PMMA with the comb polymer was believed to be statistically significant (p less than 0.0001, unpaired t-test) (See Table 1). Spincasting the comb polymer onto PET did not significantly, if at all, change the water contact angle of the surface. Although not intending to be bound by theory, it is believed that this is due to the similar wettability of the two polymers.

The formation of a stable film of the comb polymer was confirmed by XPS. Upon spincasting the comb polymer on PS, the XPS O/C ratio changed from about zero to 0.41. The experimental O/C ratio compares favorably with the bulk O/C ratio of the comb polymer of 0.45, as determined by NMR. Again, not intending to be bound by theory, this suggests that the average surface composition of the comb polymer within the top 50 Å of the surface does not deviate substantially from the bulk composition. The $C_{1s}$ spectrum of PS showed new peaks at 286.5 eV (C—O—R), 288.5 (COOR), and the disappearance of the peak at 292 eV ($\pi \rightarrow \pi^*$ shakeup satellite) upon coating PS with the amphiphilic comb polymer.

For each surface, the water contact angle was also measured as a function of immersion time of the film in water. In this example, it was observed a decrease in the contact angle upon immersion of the comb polymer-modified surfaces for 24 h in water for all three surfaces (see Table III).

TABLE III

Surface characterization of spin-cast films of the poly (MMA/HPOEM/MePOEM) comb polymer on different polymer surfaces.

| Sample | Water Contact angle (°)[a] | | XPS Analysis | | |
|---|---|---|---|---|---|
| | t = 0 h | t = 24 h | At % C | At % O | O/C |
| PS | | 88 | 100 | 0 | 0 |
| PS-CP[b] | 80 | 69 | 71.1 | 28.9 | 0.41 |
| PET | | 72 | 71.0 | 27.1 | 0.38 |
| PET-CP | 74 | 70 | 73.2 | 26.8 | 0.37 |
| PMMA | | 75 | 75.3 | 24.7 | 0.33 |

TABLE III-continued

Surface characterization of spin-cast films of the poly
(MMA/HPOEM/MePOEM) comb polymer on different polymer surfaces.

| Sample | Water Contact angle (°)[a] | | XPS Analysis | | |
|---|---|---|---|---|---|
| | t = 0 h | t = 24 h | At % C | At % O | O/C |
| PMMA-CP | 75 | 67 | 72.6 | 27.4 | 0.38 |
| Comb Polymer[c] | | | 69.2 | 30.8 | 0.45 |

[a]Standard deviation was typically 3° (n ≥ 6).
[b]Spincast comb polymers were immersed in water for 24 h.
[c]Theoretical values for a comb polymer with a stoichiometry of 61 wt. % PMMA, 21 wt. % HPOEM, and 18 wt. % MePOEM.

A potentially important consequence of the reorientation of the surface of the comb polymer in water is that the PEG chains are believed to be optimally positioned at the interface to be capable of performing two important functions, namely confer protein resistance to the surface and favorably present cell-specific ligands that are covalently attached to the ends of the oligoethylene glycol chains during the micropatterning process.

Example 13

Protein Patterning Via MAPS

With reference to FIGS. 13A–C, a carboxylated comb polymer 210 described in Example 10 was first spin-cast onto PS, TCPS, PMMA and PET. After spin-casting the comb polymer 210 onto each surface, the COOH groups in the comb polymer 210 shown in FIG. 13A were converted to N-hydroxysuccinimide (NHS) esters to activate the surface as shown in FIG. 13B. An oxidized poly(dimethyl siloxane) (PDMS) stamp 200 presenting micrometer-sized relief features was inked with an amine-linked biotin derivative (biotin-amine) 250 and brought into conformal contact with the "activated" surface, resulting in the covalent attachment of the biotin derivative 250 in the regions of the surface that were in contact with the stamp 200. This procedure was used to create periodic 40 μm wide stripes of biotin on the surface as shown in FIG. 13C that were separated by the same distance. The surface was then washed with PBS, pH 8.6 to hydrolyze residual NHS esters that did not come into conformal contact with biotin-amine during stamping. Next, the surface was incubated with a solution of Alexa488-labeled streptavidin for fluorescence microscopy, or with unlabeled streptavidin for subsequent cell attachment studies.

Figure 14B:
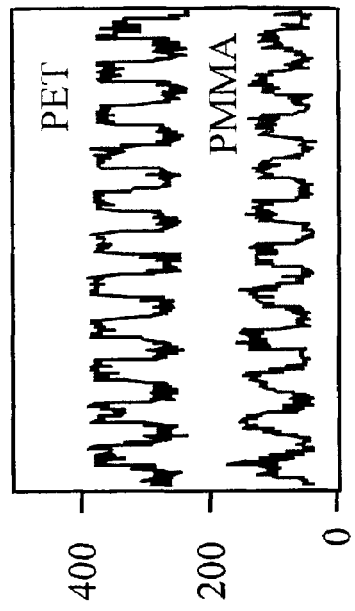
FIG. 14B and 15B show line profiles of fluorescence intensity of the patterns shown in FIGS. 14A and 15B, respectively.
Figure 14A:
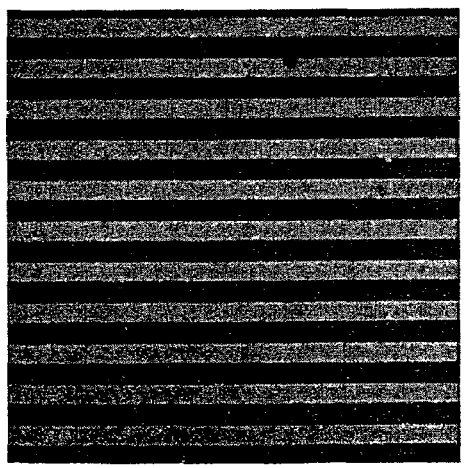
FIGS. 14A and 15A are fluorescent images of protein and peptide micropatterns on spin-cast thin films of the poly (MMA/HPOEM/POEM) comb polymer on different polymer surfaces.

FIG. 14A illustrates the formation of spatially resolved patterns of fluorescently-labeled streptavidin on a biotin micropattern fabricated on the PEG comb polymer-modified PET. Although the fluorescence intensity in the patterned regions was believed to be lower than previous results using MAPS on other polymers, the nonspecific adsorption of streptavidin in the unpatterned background regions of the comb polymer was believed to be low (see FIG. 14B) resulting in a signal-to-noise ratio (S/N) ranging from 4–6 for the different surfaces. See e.g., Z-P. Yang, A. Chilkoti, Adv. Mater. 2000, 12, 413 and Z-P. Yang, A. M. Belu, A. Liebmann-Vinson, H. Sugg, A. Chilkoti, Langmuir 2000, 16, 7482.

Example 14

Presentation of Cell-Adhesive RGD Peptide on Amphiphilic Comb Polymer

Figure 15B:
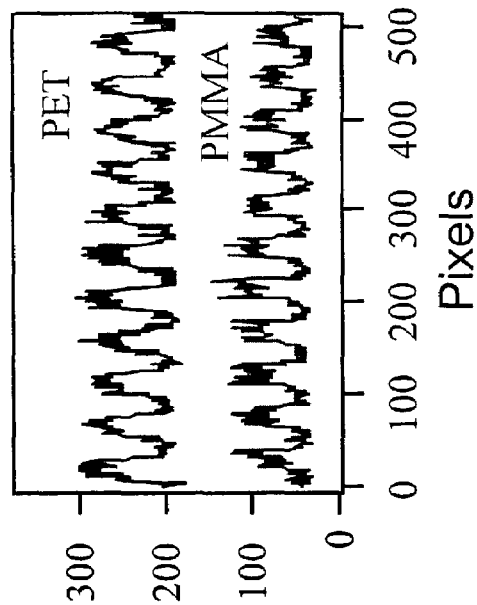
Figure 15A:
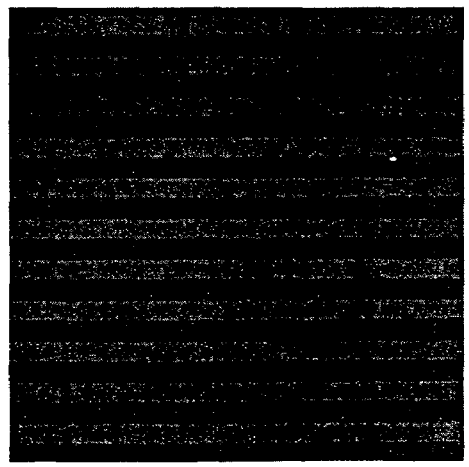

Streptavidin patterns were incubated with biotin-GRGD-SPK. FIG. 15A shows a peptide pattern created using a fluoresecent analog, biotin-GRGDSP(K-tetramethyl rhodamine) on PET. The signal to noise (S/N) of the peptide micropatterns ranged from about 5 to about 6 on the different surfaces (FIG. 15B)

Figure 16A:
FIGS. 16A and 16B illustrate phase contrast images of NIH 3T3 fibroblasts aligned along the micropatterned 40 μm wide lines of the peptide GRGDSPK fabricated on: TCPS (FIG. 16A), and PET (FIG. 16B).
Figure 16B:
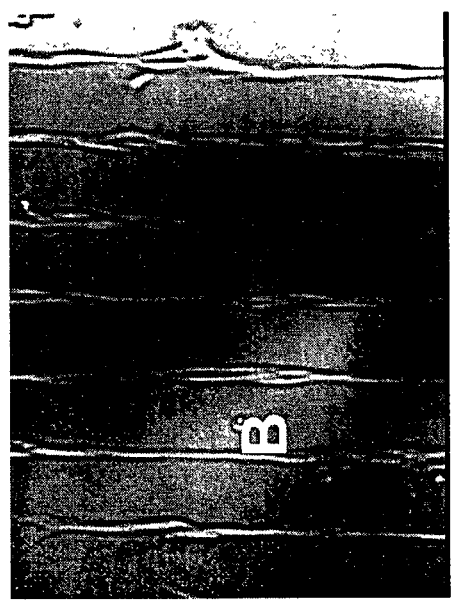
Figure 16C:
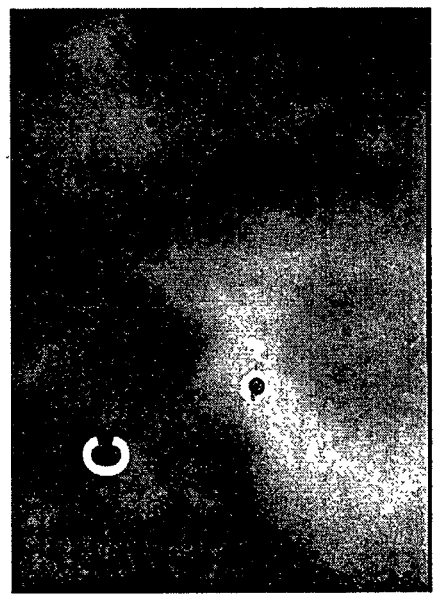
FIG. 16C illustrates a spin cast comb polymer film on TCPS without a peptide micropattern is illustrated in FIG. 16C.

The peptide micropatterns were seeded with NIH 3T3 fibroblasts from 10% serum, and the attachment and spreading of cells on the micropatterned surfaces and controls was assessed by optical microscopy as a function of time. By 24 h, spatially well-resolved patterns of the fibroblasts were observed on polymer surfaces (TCPS and PET) that were micropatterned with the cell adhesive GRGDSPK peptide (FIGS. 16A and 16B). In contrast, when cells were seeded onto the comb polymer film that had not been micropatterned with the cell-adhesive peptide, by 3 h, the cells had detached from the surface (FIG. 16C), clearly demonstrating the lack of cell-surface attachment. Micropatterns of a control, GRGESP peptide on the comb polymer did not enable the formation of cellular patterns, though some cells attached to the surface, but exhibited a round morphology, indicating their inability to spread on the surface (results not shown). These results clearly demonstrate that the presentation of a cell-adhesive RGD peptide on the amphiphilic comb polymer enables cells to be patterned in the presence of ECM proteins on the surfaces of different polymeric biomaterials, mediated by the spatially-resolved presentation of the biochemical ligand.

Example 15

Cell Micropatterning Using an Amphiphilic Comb Polymer

FIGS. 17 and 18A–C show various embodiments to create highly resolved micropatterns of comb polymer on various surfaces. As shown in FIG. 17, a biological ligand such as fibronectin (FN) 220 can be absorbed on the polymer surface 100. A PDMS stamp 200 can be used to microcontact-print comb polymer 210 on the surface 200. Alternatively, as shown in FIGS. 18A–C, micropatterning of comb polymer 1310 on the surface 1315 may be performed using a PDMS stamp 1300. After the comb polymer 1310 has been deposited on surface 1315 as shown in FIG. 18B, FN can be incubated on the remaining exposed surface 1315 to form an exposed bioligand 1340 that can comprise FN. Such methods were highly reliable and reproducible over the entire patterning areas. Subsequently, the comb micropatterns 1310 were incubated with cells to observe the preferential attachment of cells on the FN surface (bioligand 1340).

In Example 15, a comb polymer to be micropatterned was synthesized by free radical polymerization of methyl methacrylate, poly(ethylene glycol) methacrylate ($M_n$~526 g/mol) and methyl ether methacrylate ($M_n$~475 g/mol). See Banerjee, P., Irvine, D. J., Mayes, A. M., Griffith, L. G. Polymer latexes for cell-resistant and cell-interactive surfaces. *J. Biomed. Mater. Res.* 50, 331–339 (2000); Irvine, D. J., Mayes, A. M., Griffith, L. G. Nanoscale clustering of RGD peptides at surfaces using comb polymers. Synthesis and characterization of comb thin films. *Biomacromolecules* 2, 85–94 (2001). The comb polymer was carboxylated by succinic anhydride. The comb polymer was characterized by ¹H NMR in CDCl₃; 4.12 ppm (—OCH₃), 3.6–3.65 ppm (CH₂—CH₂—O—), 0.5–2 ppm (CH₂—C—(CH₃)—) and 3.39 ppm (—OH). The composition of the terpolymer was 61 wt % MMA, 21 wt % HPOEM, and 18 wt % POEM using the peaks at 4.12 ppm and 3.39 ppm for quantification. The number average molecular weight (MW) of the comb polymer ($M_n$) was ~25,000 Da with a polydispersity of ~2.7, as measured by gel permeation chromatography using polystyrene (PS) calibration standards.

Polymethamethylacrylate (PMMA), poly(ethylene terethphtalate) (PET) and PS were purchased from GoodFellow Corp., and were washed with ethanol prior to use. For the surfaces coated with fibronectin (FN), the surfaces were incubated with 20 µg/ml FN solution in PBS for 1 h. Conformal Micropatterning of comb polymer was performed using an oxidized poly(dimethyl siloxane) (PDMS) stamp presenting micrometer-sized negative features. The stamp was inked with a 1% (w/v) comb polymer solution in 50/50 (v/v) H₂O/ethanol mixture and brought into conformal contact with either unmodified surfaces or FN-adsorbed surfaces, resulting in the adsorption of the comb polymer in the regions of the surface that were in contact with the stamp according to the steps shown in FIGS. 17 and 18A–C. Thus, periodic 20 or 40 µm wide stripes, squares and circles of micropatterns were formed on the surface that were separated by 20 or 40 µm. The comb micropatterns on the untreated surfaces were incubated with 20 µg/ml FN solution, and then washed with PBS solution. Atomic force microscpoy (AFM) and x-ray photoelectron spectroscopy (XPS) were performed to measure the thickness or to confirm the stability of a comb polymer layer stored in water for a month.

Time-of-Flight Secondary Ion Mass Spectrometry (TOF-SIMS) spectra and ion images were obtained on a TOF-SIMS instrument (TOF-SIMS IV, ION-TOF, Münster, Germany). A 25-keV monoisotopic $^{69}$Ga⁺ primary ion beam generated by a Ga⁺ gun were used. "Bunched mode" was used to achieve highest mass resolution (m/Δm≈10,000) in the mass spectra. The typical target current of the primary Ga⁺ beam in the bunched mode for TOF-SIMS was 3 pA with a pre-bunched pulse width of 20 ns. The raster area of the Ga⁺ ion gun was 384×384 µm² and the raster resolution was 128×128 pixels, in order to attempt to match the pixel size with the Ga⁺ ion beam spot size (i.e. the Ga⁺ ion beam spot size was approximately 384÷128≈3 µm), thereby optimizing both spatial resolution and data rates for these gun conditions. All primary Ga⁺ ion fluences were below the damage threshold of 1×10¹³ ions cm⁻² for static SIMS.

NIH 3T3 cells were grown in RPMI1640 (Gibco BRL) supplemented with 10% fetal bovine serum (FBS) (Gibco BRL), 100 units/ml penicillin, 100 mg/ml streptomycin, and 7.5 mM HEPES at 37° C. in 5% CO₂. Cells were plated on the comb polymer micropatterned samples or controls at a density of 1×10⁵ cells/ml in RMPI1640 supplemented with 10% serum. Cells were incubated at 37° C. for 24 h, gently rinsed with culture media to remove loosely adherent cells, and imaged under phase contrast optics for a month.

Figure 19D:
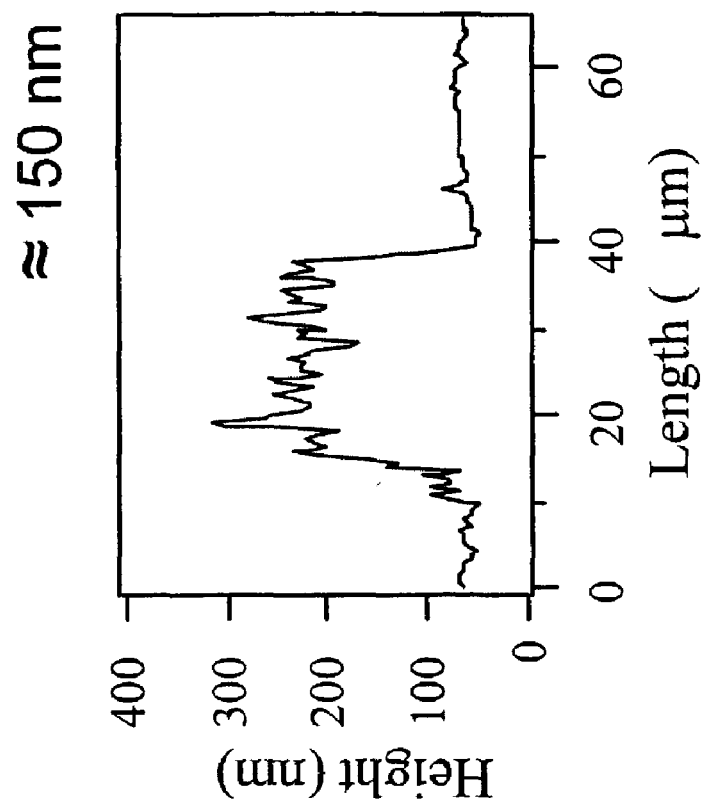
FIG. 19D is a line profile of the stripe shown in FIG. 19C.
Figure 19C:
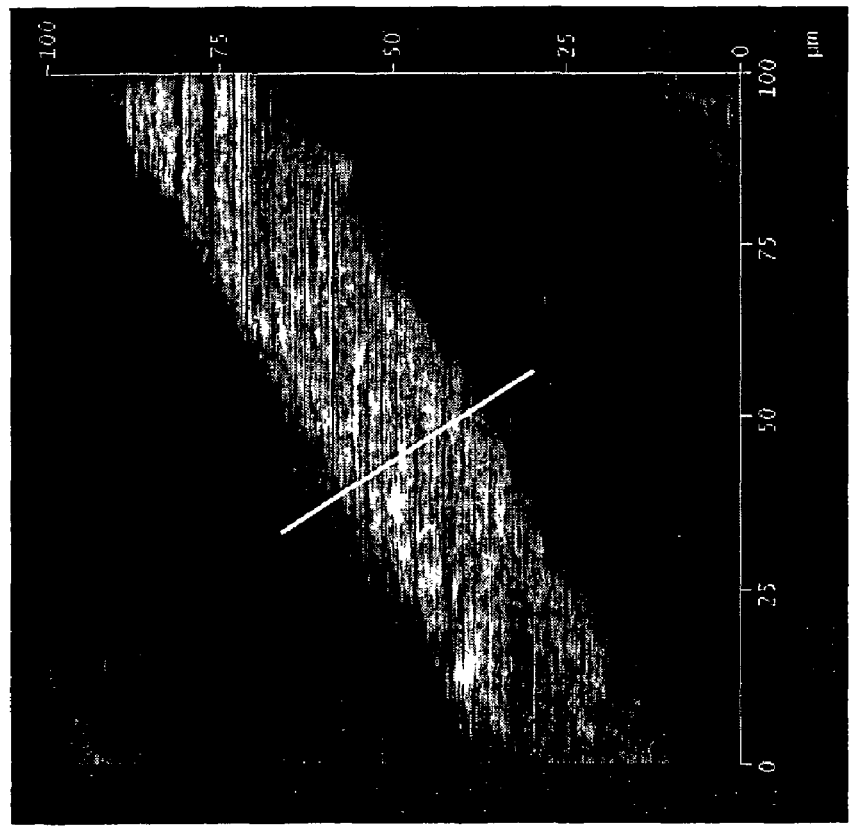
FIGS. 19C is an atomic force microscopic image of a comb polymer stripe pattern having a 20 μm stripe.

Referring to the comb polymer regions depicted in FIGS. 19A–B, the reflection image of the silicon surface micropatterned with comb polymer was taken visualized by optical microscopy. The resolution of the patterned comb polymer in FIGS. 19A–B was comparable to microcontact printing of thiols or biological molecules such as biotin and streptavidin. See Yang, Z-P., Chilkoti, A. Microstamping of a biological ligand onto an activated polymer surface. *Adv. Mater.* 12, 413–417 (2000). The bright area in the image is the silicon surface that has not contacted the PDMS surface. The dark area of the image is the comb polymer surface transferred onto the silicon surface from the PDMS stamp inked with a solution of the comb polymer. (FIGS. 19A–B) The AFM height image of the comb stripe pattern from FIG. 19B is shown in FIG. 19C. The surface profile of the comb stripe pattern from FIG. 19B is shown in FIG. 19D. The thickness of the comb polymer layer was about 150 nm as measured by atomic force microscopy (AFM). The stability of the comb layer in water was investigated with AFM and water contact angle measurement. The comb layer was stable at least for about a month without any deformation or desorption in aqueous solution. X-ray photoelectron spectroscopy (XPS) also confirmed the existence of a thin comb layer after prolonged storage in water.

FN was selected for the selective attachment of cells because the RGD (arg-gly-asp) sequence of FN is a ligand for the integrin superfamily of cell-surface receptors present on a number of different mammalian cells, and has been implicated in the adhesion and spreading of these cells on the extracellular matrix (ECM). See Pierschbacher, M. D., Ruoslahti, E. Cell attachment activity of fibronectin can be duplicated by small synthetic fragments of the molecule. *Nature* 309, 30–33 (1984). FN was either adsorbed on the surfaces prior to microcontact-printing of a comb polymer on it or incubated with surfaces that had been microcontact-printed with a comb polymer as shown in FIGS. 17 and 18A–C. The selective adsorption of FN on the surface was proved using time of flight-secondary ion mass spectroscopy (TOF-SIMS). TOF-SIMS was selected because it is a surface analytical technique with attributes that are useful in analysis of the subtle chemical changes on the surface. TOF-SIMS can provide high-resolution (m/Δm~10,000) mass spectra of the surface with extremely high detection sensitivity. Because the secondary ions are formed within the top 1 to 2 monolayers of the solid surface, TOF-SIMS can be surface sensitive, which may be useful for analyzing the adsorption of ligands on the surface. TOF-SIMS ion imaging can also provide spatial distributions of mass-resolved secondary ions emitted from the surface with submicron lateral resolution.

Positive and negative TOF-SIMS spectra and images were obtained with the surfaces patterned with comb polymer. In order to characterize the surface, TOF-SIMS measurements were performed on polystyrene samples. The main contributions to the positive spectrum of PS arise from unsaturated hydrocarbon peaks. Among those, peaks at m/z=77 ($C_6H_5^+$) and m/z=91 ($C_7H_7^+$) correspond to aromatic ions and are highly characteristic of the presence of styrene rings. (results not shown) At the same time, the presence of the comb polymer was followed by TOF-SIMS. The positive peaks at m/z=31, 44 and the negative peaks at m/z=12, 31 were attributed respectively to $CH_3O^+$, $C_2H_4O^+$ and $O^-$, $CH_3O^-$ and are unique to the comb polymer. From the positive reference spectrum of FN on PS, TOF-SIMS detected nitrogen-containing peaks at m/z=18 ($NH_4^+$), m/z=30 ($CH_4N^+$), and m/z=44 ($C_2H_6N^+$) that are characteristic of FN. In the negative spectrum of FN, the most characteristic peaks in the considered mass range were at m/z=16 ($O^-$), m/z=26 ($CN^-$), m/z=32 ($S^-$) and m/z=42 ($CNO^-$).

The imaging mode of TOF-SIMS was used to analyze the patterned samples and monitor the spatial distribution of characteristic molecular species. FIGS. 20A–C and 21A–C show TOF-SIMS images of the comb polymer patterns combined with FN. $CH_3O^+$ and $CH_3O^-$ ions were selected for imaging the patterns of comb polymer containing oligo (ethyl glycol) molecules. Each feature is approximately 40

μm, and the spacing between features is the same. Nitrogen-containing ions are characteristic of the presence of FN as described above. In case of FN-adsorbed polystyrene, CNO⁻ ion from FN showed a high contrast image because of the existence of a comb polymer layer covering FN. In addition, the CN⁻ ion image from a FN-coated PS showed a high contrast while the same ion image of FN-incubated comb polymer patterns showed a lower contrast. The contrast image also appeared with the ion of $C_2H_6N^+$. It resulted from the nonspecific adsorption of FN on comb polymer patterns during incubation, however, the adsorption was minimized by antifouling effect of EG chains in comb polymer.

From control experiments, it was determined that the comb polymer surface is antifouling, and the methods can be a route for the cell attachment on various surfaces. To verify this, several polymer materials were selected which are widely used as a biomaterial; tissue culture polystyrene (TCPS), poly(ethylene terephthalate) (PET), polymethylmethacrylate (PMMA) and polystyrene (PS). See Ratner, B. D. *Biomaterials science: an introduction to materials in medicine;* Academic Press: San Diego, Calif., 1996. The comb polymer spincast on TCPS was antifouling to cells (FIG. 22A). Even after the adsorption of FN on the comb polymer surface, just a few cells attached on the surface due to the strong antifouling effect of flexible oligo(ethylene glycol) chains. (FIG. 22B) Compared with the results described above, comb micropatterns on the FN-adsorbed PS created well-aligned cell micropattern indicating the affinity of FN to cells. (FIGS. 22C–E)

Without wishing to be bound by a single theory, the preferential attachment of cells on the space between comb polymer patterns may be caused by two reasons: 1) FN adsorbed on the region of a comb polymer may have a low surface density. That is, the nonfouling effect of a comb polymer minimizes the adsorption of FN on the surface and keeps the surface density of ligands lower on the comb polymer than is needed for anchoring cells on the surface. 2) The comb polymer may directly repel cells. The possible attachment of cells due to the low concentration of FN on the comb polymer region can be obviated by first coating the surface with the ligand, e.g. by adsorbing FN on the surface followed by the formation of micropatterns of a comb polymer that are microcontact printed or deposited from microwells on the FN-coated surface (FIGS. 22F–H).

Cell patterning using an amphiphilic comb polymer showed that reliable and reproducible cell patterns can be created even after long-term incubation of the surfaces in serum without any significant cell spreading outside the patterned areas of FN. (FIGS. 23A–H) The time dependence of cell patterns was investigated for a month by optical microscopy under phase contrast optics. For the square patterns, the cell patterns were stable at least for two weeks, and a few connections of cells between adjacent features were observed after that time. (FIG. 23A) However, some cell patterns kept their shape even after a month. For the stripe patterns, the cell patterns were still reasonably well defined after a month. (FIGS. 23B) The results in FIGS. 23A–H may be compared with bovine serum albumin (BSA), with which the cell patterns could be kept their original dimension for 1 h and no more patterns after 4 h incubation, and ethylene glycol thiols, whose application was limited on gold. Ostuni, E., Kane, R., Chen, C. S., Ingber, D. E., Whitesides, G. M. Patterning mammalian cells using elastomeric membranes. *Langmuir* 16, 7811–7819 (2000). Chen, C. S.; Mrksich, M.; Huang, S.; Whitesides, G. M.; Ingber, D. E. *Geometric control of cell life and death. Science* 1997, 276, 1425–1428. Chen, C. S.; Mrksich, M.; Huang, S.; Whitesides, G. M.; Ingber, D. E. *Micropatterned surfaces for control of cell shape, position, and function. Biotechnol. Prog.* 1998, 14, 356–363. Mrksich, M.; Dike, L. E.; Tien, J.; Ingber, D. E.; Whitesides, G. M. *Exp. Cell Res.* 1997, 235, 305–313. Therefore, a comb polymer can be as a physico-chemical barrier to cell spreading in Micropatterning on various surfaces.

Example 16

Microwell Patterning on a Substrate Surface

With reference to FIGS. 24A–G, elastomeric microwell reservoirs were used to pattern a biolmoecule of interest on a substrate surface. As shown in FIG. 24A, poly(dimethylsiloxane) (PDMS) stamp 300 with positive relief features was cast from a silicon master 310 with negative relief features resulting in a microwell 320 (FIGS. 24B and 24C). *Siloxane Polymers;* Clarson, S. J., Semlyen, J. A., Eds; Prentice Hall: Englewood, N.J., 1993. As shown in FIGS. 24B and 24C, the microwells 320 were molded from the elastomeric PDMS stamp 300. Xu, B.; Arias, F.; Brittain, S. T.; Zhao, X. M.; Grybowski, B.; Torquato, S.; Whitesides, G. M. *Adv. Mater.* 1999, 11, 1186–1189. Alternatively, the microwells 320 can be directly fabricated by casting PDMS against a silicon or photoresist master with positive relief features. (not shown) This process is more laborious than directly casting from a microfabricated silicon master. However, the use of the silicon master is reduced, which may reduce the cost. As shown in FIG. 24D, the microwell 320 can then be filled with a solution 330. The solution 330 can contain a ligand.

Figure 25B:
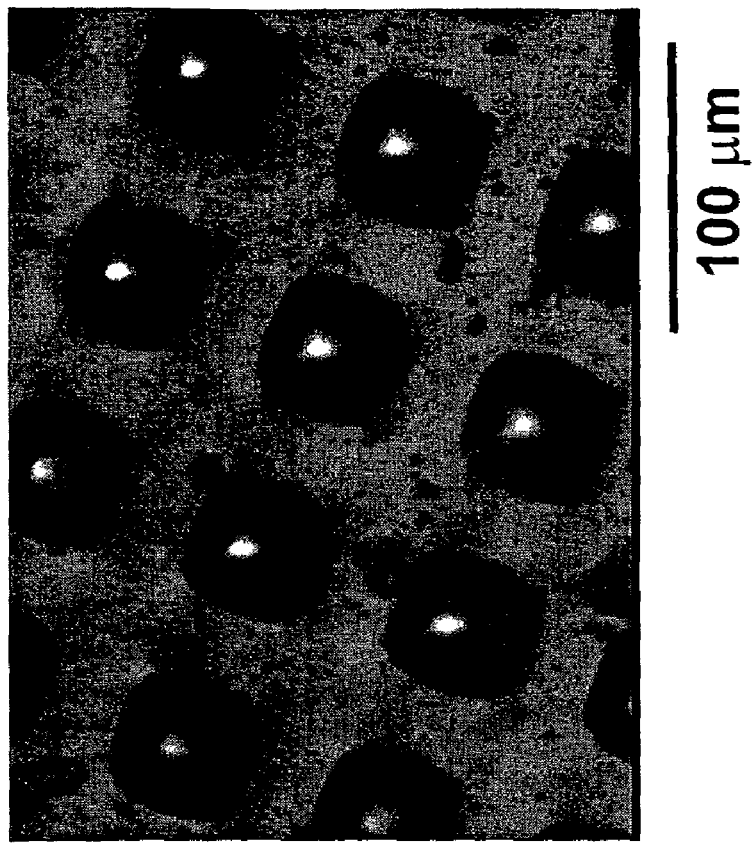
FIGS. 25A and 25B are optical micrographs of PDMS molds filled with an aqueous solution.
Figure 25A:
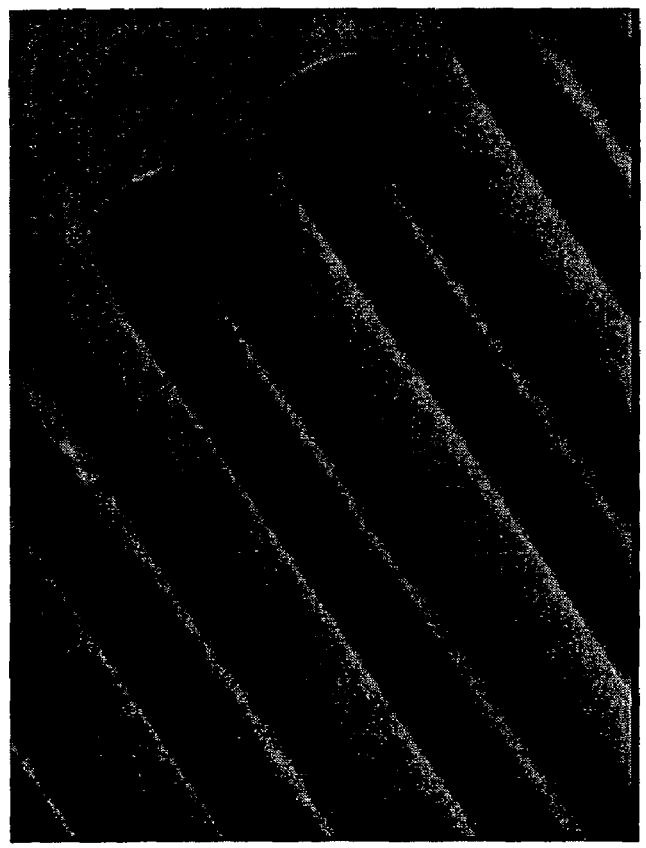

As shown in FIGS. 25A–B, several shapes of microwells and channels may be molded from elastomeric PDMS masters. Each mold may provide high-resolution microstructures with feature sizes as small as 30 μm. FIG. 25A is an optical micrograph of a PDMS mold with square microwells filled with aqueous solution, and FIG. 25B is an optical micrograph depicting microchannels.

A PDMS mold was oxidized with an air plasma (80 W, 1 min, Plasmod, March Instruments) to make the surface uniformly hydrophilic (not shown). The top surface of the microwell was contact-printed with hexadecanethiol (HDT) using a flat, oxidized PDMS stamp (not shown) and allowed to dry, which selectively rendered the area between the wells hydrophobic. HDT was selected because it is believed to oxidize PDMS, but it does not dissolve in contact with aqueous solution. It is believed that other reagents may be substituted. The difference in wettability between the wells, which are hydrophilic, and the region between the wells, which are hydrophobic, can enable easy filling and confinement of a aqueous solution containing a biomolecule of interest to the microwells during a filling step. As shown in FIG. 24D, the microwell 320 can then be filled with a solution 330.

Specifically, a poly(ethylene terephthalate) (PET) film (obtained from Dupont, Inc.) was chemically derivatized to introduce COOH groups. Yang, Z. P.; Chilkoti, A. *Adv. Mater,* 2000, 12, 413. The surface COOH groups were then reacted with N-hydroxysuccinimide (NHS) (0.2 M) and 1-ethyl-3-(dimethyl-amino)propyl carbodiimide (EDAC) (0.1 M) in distilled water. The NHS-ester-functionalized surface was dried under nitrogen and used immediately for micropatterning biomolecules.

A cell-adhesive peptide was covalently patterned using microwell techniques. Massia, S. P.; Hubbell, J. A. *J.*

Biomed. Mater. Res. 1991, 25, 223.; Rezania, A.; Thomas, C. H.; Branger, A. B.; Waters, C. M.; Healy, K. W. *J. Biomed. Mater. Res.* 1997, 37, 9. In certain embodiments, biotin can be patterned on a surface and then a steptavidin-biotin system can be used subsequently to pattern a biotinylated peptide. Wilchek, M.; Bayer, E. A. *Avidin-Bioltin Technology;* Methods in Enzymology, Vol. 184; Academic Press: Sandiego, Calif., 1990; Green, N. M. *Biochem J.* 1966, 101, 774. In other embodiments, direct, covalent patterning of the peptide can be performed onto a derivatized PET surface. Both biotin-GRGDSP(K-TMR)-NH$_2$ were synthesized by (lower case) Anaspec, Inc. (San Jose, Calif.) and were of over 90% purity. Tetramethyl rhodamine (TMR) was covalently attached to the amine moiety in the lys (K) residue during solid-phase synthesis of each peptide.

In separate experiments, 100 µL of a 10 mM solution of EZ-Link biotin-PEO-LC-amine, which is a long-chain (LC) derivative of biotin with a poly-(ethylene oxide) (PEOP) spacer (22.0 Å spacer length), ((+)-biotinyl-3,6,9-trioxaundecanediamine, Pierce) (biotin-NH$_2$) in phosphate buffer or gly-arg-gly-asp-ser-pro-lys)tetramethylrhodamine)NH$_2$ in phosphate buffer (GRGDSP(K-TMR)NH$_2$) were pipetted onto the PDMS microwells 320, and the droplets that remained on the hydrophobic surface between the microwells were blown away with a stream of nitrogen gas. The derivatized polymer surface 340 was then brought into physical contact with the PDMS microwells 320 as shown in FIG. 24E–F. The elastomeric nature of PDMS can provide a substantially leak-proof seal between the microwell 320 and the surface 340. The entire assembly was then inverted, as shown in FIG. 24F in order to bring the solution 330 in contact with the surface 340. The reaction between biotin-NH$_2$ (or GRGDSP(K-TMR)-NH$_2$) and the NHS esters on the surface of PET was allowed to proceed for 30 minutes at room temperature. Subsequently, the surface 340 was lifted away from the microwell 320 and extensively washed in ethanol, leaving the ligand 350 on the the surface 340.

Figure 26B:
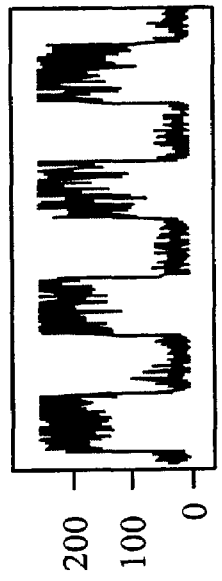
FIGS. 26B, 27B, and 28B are line profiles of the micropatterns in FIGS. 26A, 27A, and 28A, respectively.
Figure 26A:
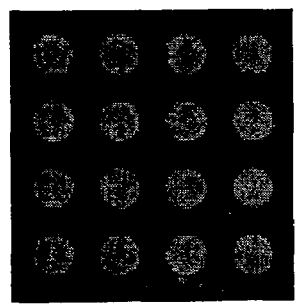
FIGS. 26A, 27A, and 28A are micropatterns fabricated using an elastomeric microwell reservoir with biotin-$NH_2$/Alexa488-streptavidin (FIG. 27A), biotin-$NH_2$/streptavidin/biotin—GRGDSP(K-TMR) (FIG. 28A), and covalent patterning of GRGDSP(K-TMR)-$NH_2$.

After patterning biotin-NH$_2$ on PET using the process described herein, the surface was incubated with 0.1 µM unlabeled streptavidin or Alexa488-labeled streptavidin in 10 mM HEPES, 0.02%(v/v) Tween 20 detergent for 30 minutes at room temperature. The samples were washed exhaustively in buffer, and confocal fluorescence microscopy was used to examine each stage of the patterning of the biotinylated peptide. Spatially well-resolved patterns of streptavidin were observed (FIG. 26A) with a signal-to-noise ration (S/N) in the patterns (pattern intensity/background intensity) of 10±0.9 (FIG. 26B), which is greater than the S/N of about 5 that is typically obtained by reactive µCP on PET. A control experiment was performed by incubating a biotin micropattern with Alexa488-labeled streptavidin that had been presaturated with free biotin. No patterns were observed by fluorescence microscopy. Without intending to be bound by theory, it is believed that the formation of streptavidin patterns was caused by molecular recognition between the protein and micropatterned biotin on the surface. It is also believed that a higher contrast of streptavidin patterns obtained by the microwell patterns compared to µCP of biotin-NH$_2$ on PET (see Yang, Z. P.; Chilkoti, A. *Adv. Mater.* 2000, 12, 413. and Yang, Z. P.; Belu A. M.; Liebmann-Vinson, A.; Sugg, H.; Chilkoti, A. *Langmuir* 2000, 16, 7482.) may result from the longer contact time of the surface with biotin-NH$_2$ than is typically possible with µCP, thereby providing a higher surface density of immobilized biotin.

Figure 27B:
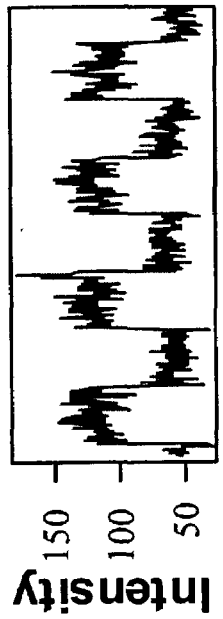
Figure 28B:
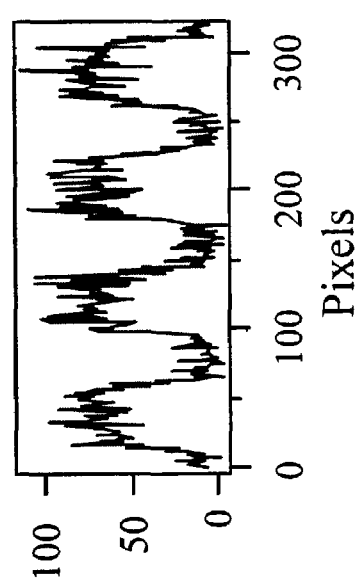
Figure 27A:
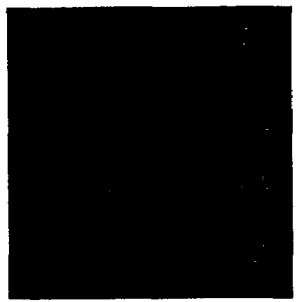
Figure 28A:
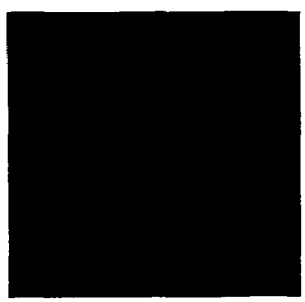

Next, an unlabled streptavidin pattern was incubated with 0.1 µM biotin-GRGDSP(K-TMR) (10 mM HEPES, 0.02% (v/v) Tween 20 detergent) resulting in the formation of a peptide micropattern (FIG. 27A). The S/N in the pattern was 7±0.5 (FIG. 27B). The feasibility of direct micro patterning of a GRGDSPK(TMR)-NH$_2$ peptide was also investigated by reaction between the NH$_2$ moiety and the NHS ester on the surface (FIG. 28A). Patterning was successful, and a S/N of the peptide patterns created by such covalent coupling was 5±0.8 (FIG. 28B). It is noted that the S/N of the peptide patterns created by covalent coupling (FIG. 28B) was lower than the S/N of 7±0.5 (FIG. 27B) (P<0.001, unpaired t-test) obtained for its biotin-conjugate patterned using the streptavidin-biotin system. Without wishing to be bound by theory, it is believed that the lower S/N obtained by covalent patterning is due to the limited reactivity of the amine moiety which is caused by steric hindrance from the adjacent dye molecule.

The processes described in FIGS. 24A–G and the accompanying discuss may be performed on a variety of surface materials, including polymers, SAMs on gold or glass. The concentration of the biomolecule in the aqueous solution and its contact time with the surface can be varied over a wide range. Low-molecular weight PDMS is generally not left behind in the patterned regions as has been observed with µCP methods. Isolated structures such as circles, squares, stripes and other patterns can be fabricated. Microwell patterning methods can be interfaced with piezoelectric or inkjet dispensers to simultaneously create patterns of many different biomolecules. Thus, spatial resolution may be dictated by the size of the microwells, which can be controlled, and not by droplet spreading.

The foregoing is illustrative of the present invention and is not to be construed as limiting thereof The invention is defined by the following claims, with equivalents of the claims to be included therein.

That which is claimed is:

1. A method of attaching a ligand to a surface, comprising:
   contacting a surface with a substrate containing an amphiphilic comb polymer wherein the substrate is configured to provide a pattern of the amphiphilic comb polymer on a selected region of the surface;
   separating the substrate from the surface, thereby leaving the amphiphilic comb polymer on the selected region of the surface to provide a selected region of the surface having amphiphilic comb polymer thereon; and then
   depositing a ligand on the surface such that the selected region of the surface having the amphiphilic comb polymer thereon is substantially free of the ligand.

2. The method of claim 1, wherein the surface is a polymer surface.

3. The method of claim 1, wherein the ligand is a biological ligand.

4. The method of claim 1, wherein the substrate comprises a stamp, and wherein the amphiphilic comb polymer is attached to a surface of the stamp.

5. The method of claim 1, wherein the substrate comprises at least one well and wherein an aqueous solution is present in the at least one well, the aqueous solution comprising the amphiphilic comb polymer.

6. The method of claim 1, wherein the ligand is deposited by adsorption from a solution.

7. The method of claim 1, wherein the ligand is deposited by chemical conjugation from a solution.

8. The method of claim 1, wherein the amphiphilic comb polymer comprises a backbone formed of a hydrophobic water-insoluble polymer and at least one side chain formed of a hydrophilic polymer.

9. The method of claim 8, wherein the hydrophobic water-insoluble polymer comprises a biodegradable polymer.

10. The method of claim 9, wherein the biodegradable polymer is selected from the group consisting of poly(amino acids), poly(anhydrides), poly(orthoesters), poly(phosphoesters), polylactones, poly(sebacate), poly(hydroxy acids), copolymers thereof, and mixtures thereof.

11. The method of claim 8, wherein the hydrophobic water-insoluble polymer comprises a non-biodegradable polymer.

12. The method of claim 11, wherein the non-biodegradable polymer is selected from the group consisting of polyalkylenes, polyvinyl ethers, polyvinyl esters, polysiloxanes, polystyrene, polyurethanes, polyacrylates, polyacrylamides, copolymers thereof, and mixtures thereof.

13. The method of claim 8, wherein the hydrophilic polymer is formed from polymeric blocks selected from the group consisting of poly(ethylene glycol), poly(ethylene oxide), poly(propylene glycol), poly(propylene oxide), partially or fully hydrolyzed poly(vinyl alcohol), poly(vinylpyrrolidone), dextran, and mixtures thereof.

14. The method of claim 1, wherein the ligand is selected from the group consisting of small biological molecules, proteins, peptides, nucleic acids, lipids, saccharides, oligosaccharides, carbohydrates, lipopolysaccharide, lipoprotein, peptide nucleic acids (PNA), ribozymes, DNA or PNA aptamer.

15. The method of claim 1, wherein the ligand is a small biological molecule.

16. The method of claim 1, wherein the ligand is a peptide.

17. The method of claim 1, wherein the ligand is a protein.

18. The method of claim 1, wherein the ligand is biotin.

19. The method of claim 1, wherein the ligand is a synthetic polymer.

20. The method of claim 1, wherein the ligand is a biological polymer.

21. The method of claim 1, wherein the surface is the surface of a polymer selected from the group consisting of poly(ethylene terephthalate) (PET), polystyrene (PS), polycarbonate (PC), poly(epsilon-caprolactone) (PECL or PCL), poly(methyl methacrylate) (PMMA), poly(lactic acid) (PLA), polydimethylsiloxane (PDMS), polybutadiene (PB), polyvinylalcohol (PVA), fluorinated polyacrylate (PFOA), poly(ethylene-butylene) (PEB), poly(tetrafluoroethylene), and poly(styrene-acrylonitrile) (SAN).

22. The method of claim 1, wherein the surface is configured as a flat surface.

23. The method of claim 1, wherein the surface is configured as a curved surface.

24. The method of claim 4, wherein the stamp is an elastomeric stamp.

25. The method of claim 4, wherein the stamp is a poly(dimethylsiloxane) (PDMS) stamp.

26. The method of claim 4, wherein the stamp is plasma-oxidized prior to the contacting step.

27. The method of claim 4, wherein the stamp is chemically oxidized prior to the contacting step.

28. The method of claim 1, wherein the ligand is cytophilic.

29. The method of claim 1, further comprising binding another ligand to the at least one ligand on the surface after the separating step.

30. The method of claim 29, wherein the other ligand is streptavidin, and the ligand covalently bound to the surface after the separating step is biotin.

* * * * *